US011227686B2

(12) United States Patent
Makrinich et al.

(10) Patent No.: US 11,227,686 B2
(45) Date of Patent: Jan. 18, 2022

(54) SYSTEMS AND METHODS FOR PROCESSING INTEGRATED SURGICAL VIDEO COLLECTIONS TO IDENTIFY RELATIONSHIPS USING ARTIFICIAL INTELLIGENCE

(71) Applicant: Theator Inc., Palo Alto, CA (US)

(72) Inventors: Evgeny Makrinich, Tel Aviv (IL);
Tamir Wolf, Palo Alto, CA (US);
Dotan Asselmann, Holon (IL)

(73) Assignee: THEATOR INC., Palo Alto, CA (US)

( * ) Notice: Subject to any disclaimer, the term of this patent is extended or adjusted under 35 U.S.C. 154(b) by 0 days.

(21) Appl. No.: 17/224,724

(22) Filed: Apr. 7, 2021

(65) Prior Publication Data

US 2021/0313052 A1  Oct. 7, 2021

Related U.S. Application Data

(63) Continuation of application No. PCT/US2021/025522, filed on Apr. 2, 2021.
(Continued)

(51) Int. Cl.
*G16H 40/20* (2018.01)
*G16H 50/70* (2018.01)
(Continued)

(52) U.S. Cl.
CPC ......... *G16H 40/20* (2018.01); *G06K 9/00718* (2013.01); *G06K 9/00744* (2013.01);
(Continued)

(58) Field of Classification Search
CPC ........ G16H 40/20; G16H 10/60; G16H 15/00; G16H 30/20; G16H 50/70; G16H 30/40;
(Continued)

(56) References Cited

U.S. PATENT DOCUMENTS 9,836,654 B1  12/2017  Alvi et al.
10,387,720 B2  8/2019  Johnson et al.
(Continued)

FOREIGN PATENT DOCUMENTS

CA  2575759 A1  2/2006
CA  3049148 A1  8/2018
(Continued)

OTHER PUBLICATIONS

"Video Analysis: An Approach for Use in Health Care"; Mackenzie et al., Handbook of Human Factors and Ergonomics in Health Care and Patient Safety, Second Edition; CRC Press, Aug. 3, 2011; pp. 523-541.
(Continued)

*Primary Examiner* — Michael Tomaszewski
*Assistant Examiner* — Jay M. Patel
(74) *Attorney, Agent, or Firm* — Finnegan, Henderson, Farabow, Garrett & Dunner, LLP

(57) ABSTRACT

Systems, methods, and computer readable media related to statistical analysis across surgical videos are disclosed. The methods may include receiving video frames across multiple surgical videos, each surgical video comprising multiple surgical procedures performed by a specific medical professional across differing patients. A set of surgical event-related categories may be accessed and video frames of each surgical video may be analyzed to identify surgical events defined by a subgroup of frames. Each subgroup of frames may be assigned to one of the surgical event-related categories to thereby interrelate subgroups of frames from differing surgical procedures to a common surgical event-related category. Statistics may be derived for each surgical event-related category and then aggregated within each category and displayed with the surgical event-related categories for selection. Upon receiving a selection, at least part of the
(Continued)

frames assigned to the particular surgical event-related category may be presented.

20 Claims, 25 Drawing Sheets

Related U.S. Application Data

(60) Provisional application No. 63/149,565, filed on Feb. 15, 2021, provisional application No. 63/133,579, filed on Jan. 4, 2021, provisional application No. 63/079,326, filed on Sep. 16, 2020, provisional application No. 63/048,894, filed on Jul. 7, 2020, provisional application No. 63/041,976, filed on Jun. 21, 2020, provisional application No. 63/036,210, filed on Jun. 8, 2020, provisional application No. 63/029,985, filed on May 26, 2020, provisional application No. 63/005,348, filed on Apr. 5, 2020.

(51) Int. Cl.
*G16H 30/20* (2018.01)
*G16H 30/40* (2018.01)
*G16H 15/00* (2018.01)
*G06K 9/00* (2006.01)
*G06Q 10/06* (2012.01)
*G16H 10/60* (2018.01)
*G16H 70/20* (2018.01)
*G16H 50/20* (2018.01)
*G06F 3/0482* (2013.01)

(52) U.S. Cl.
CPC ..... *G06K 9/00758* (2013.01); *G06K 9/00765* (2013.01); *G06Q 10/06398* (2013.01); *G16H 10/60* (2018.01); *G16H 15/00* (2018.01); *G16H 30/20* (2018.01); *G16H 30/40* (2018.01); *G16H 50/70* (2018.01); *G16H 70/20* (2018.01); *G06F 3/0482* (2013.01); *G06K 2009/00738* (2013.01); *G06K 2209/05* (2013.01); *G16H 50/20* (2018.01)

(58) Field of Classification Search
CPC .. G16H 70/20; G16H 50/20; G06G 10/06398; G06F 3/0482
See application file for complete search history.

(56) References Cited

U.S. PATENT DOCUMENTS

| | | | |
|---|---|---|---|
| 10,646,156 | B1 | 5/2020 | Schnorr |
| 10,791,301 | B1 | 9/2020 | Garcia Kilroy et al. |
| 10,878,966 | B2 | 12/2020 | Wolf et al. |
| 2002/0172498 | A1 | 11/2002 | Esenyan et al. |
| 2004/0062381 | A1 | 4/2004 | Shambaugh et al. |
| 2004/0078236 | A1 | 4/2004 | Stoodley et al. |
| 2004/0125121 | A1 | 7/2004 | Pea et al. |
| 2005/0149361 | A1 | 7/2005 | Saus et al. |
| 2006/0159325 | A1 | 7/2006 | Zeineh et al. |
| 2007/0156344 | A1 | 7/2007 | Sender et al. |
| 2008/0243064 | A1 | 10/2008 | Stahler et al. |
| 2009/0192823 | A1 | 7/2009 | Hawkins et al. |
| 2009/0300507 | A1 | 12/2009 | Raghavan et al. |
| 2010/0001149 | A1 | 1/2010 | Song et al. |
| 2010/0036676 | A1 | 2/2010 | Safdi et al. |
| 2010/0134609 | A1 | 6/2010 | Johnson |
| 2011/0046476 | A1 | 2/2011 | Cinquin et al. |
| 2011/0225000 | A1 | 9/2011 | Selim |
| 2011/0264528 | A1 | 10/2011 | Whale et al. |
| 2011/0276340 | A1 | 11/2011 | DeBoer et al. |
| 2011/0306985 | A1 | 12/2011 | Inoue et al. |
| 2012/0035963 | A1* | 2/2012 | Qian ............ G16H 30/20 705/3 |
| 2012/0177256 | A1 | 7/2012 | Keefe et al. |
| 2013/0297343 | A1 | 11/2013 | Hirose et al. |
| 2014/0081659 | A1 | 3/2014 | Nawana et al. |
| 2014/0226888 | A1* | 8/2014 | Skidmore ........ G06T 7/0014 382/131 |
| 2014/0270711 | A1 | 9/2014 | Maser et al. |
| 2014/0276940 | A1 | 9/2014 | Seo |
| 2014/0286533 | A1 | 9/2014 | Luo et al. |
| 2014/0297301 | A1 | 10/2014 | Rock |
| 2015/0190208 | A1 | 7/2015 | Silviera |
| 2016/0067007 | A1 | 3/2016 | Piron et al. |
| 2016/0191887 | A1 | 6/2016 | Casas |
| 2016/0259888 | A1* | 9/2016 | Liu ............ G16H 70/20 |
| 2017/0053543 | A1 | 2/2017 | Argawal et al. |
| 2017/0071679 | A1 | 3/2017 | Weir et al. |
| 2017/0119258 | A1 | 5/2017 | Kotanko et al. |
| 2017/0132785 | A1 | 5/2017 | Wshah et al. |
| 2017/0177806 | A1 | 6/2017 | Fabian |
| 2017/0312031 | A1 | 11/2017 | Amanatullah et al. |
| 2018/0110398 | A1 | 4/2018 | Schwartz et al. |
| 2018/0122506 | A1 | 5/2018 | Grantcharov et al. |
| 2018/0174311 | A1 | 6/2018 | Kluckner et al. |
| 2018/0174616 | A1 | 6/2018 | Aguilar et al. |
| 2018/0197624 | A1 | 7/2018 | Robaina et al. |
| 2018/0247024 | A1* | 8/2018 | Divine ............ G06T 11/60 |
| 2018/0303552 | A1 | 10/2018 | Ryan et al. |
| 2018/0322949 | A1* | 11/2018 | Mohr ............ G06F 16/71 |
| 2019/0005848 | A1 | 1/2019 | Garcia Kilroy et al. |
| 2019/0006047 | A1 | 1/2019 | Gorek et al. |
| 2019/0060893 | A1 | 2/2019 | Evans et al. |
| 2019/0090969 | A1 | 3/2019 | Jarc et al. |
| 2019/0125361 | A1 | 5/2019 | Shelton, IV et al. |
| 2019/0201136 | A1 | 7/2019 | Shelton, IV et al. |
| 2019/0201141 | A1 | 7/2019 | Shelton, IV et al. |
| 2019/0206565 | A1* | 7/2019 | Shelton, IV ......... A61B 34/74 |
| 2019/0223961 | A1 | 7/2019 | Barral et al. |
| 2019/0272917 | A1 | 9/2019 | Couture et al. |
| 2019/0279765 | A1 | 9/2019 | Giataganas et al. |
| 2019/0347557 | A1 | 11/2019 | Khan et al. |
| 2019/0362834 | A1 | 11/2019 | Venkataraman et al. |
| 2019/0365252 | A1 | 12/2019 | Fernald et al. |
| 2019/0380792 | A1 | 12/2019 | Poltaretskyi et al. |
| 2020/0030044 | A1 | 1/2020 | Wang et al. |
| 2020/0168334 | A1 | 5/2020 | Mowery |
| 2020/0194111 | A1 | 6/2020 | Venkataraman et al. |
| 2020/0226751 | A1 | 7/2020 | Jin et al. |
| 2020/0237452 | A1 | 7/2020 | Wolf et al. |
| 2020/0258616 | A1 | 8/2020 | Likosky et al. |
| 2020/0268457 | A1 | 8/2020 | Wolf et al. |
| 2020/0268469 | A1 | 8/2020 | Wolf et al. |
| 2020/0268472 | A1 | 8/2020 | Wolf et al. |
| 2020/0272660 | A1 | 8/2020 | Wolf et al. |
| 2020/0273548 | A1 | 8/2020 | Wolf et al. |
| 2020/0273552 | A1 | 8/2020 | Wolf et al. |
| 2020/0273557 | A1 | 8/2020 | Wolf et al. |
| 2020/0273560 | A1 | 8/2020 | Wolf et al. |
| 2020/0273561 | A1 | 8/2020 | Wolf et al. |
| 2020/0273563 | A1 | 8/2020 | Wolf et al. |
| 2020/0273575 | A1 | 8/2020 | Wolf et al. |
| 2020/0273577 | A1 | 8/2020 | Wolf et al. |
| 2020/0273581 | A1 | 8/2020 | Wolf et al. |
| 2020/0337648 | A1 | 10/2020 | Saripalli et al. |
| 2021/0012868 | A1 | 1/2021 | Wolf et al. |

FOREIGN PATENT DOCUMENTS

| | | | |
|---|---|---|---|
| WO | WO2015066565 | A1 | 5/2015 |
| WO | WO-2017031175 | A1 | 2/2017 |
| WO | WO-2018089816 | A2 | 5/2018 |
| WO | WO-2019040705 | A1 | 2/2019 |

(56) References Cited

FOREIGN PATENT DOCUMENTS

WO WO 2019/079430 A1 4/2019
WO WO2019226182 A1 11/2019

OTHER PUBLICATIONS

International Search Report, issued from the European Patent Office in International Application No. PCT/US2020/019050, dated Jul. 6, 2020 (8 pages).

Bernd Münzer et al, "EndoXplore: A Web-Based Video Explorer for Endoscopic Videos", 2017 IEEE International Symposium on Multimedia (ISM), Dec. 11, 2017, pp. 366-367.

Written Opinion of the International Searching Authority for International Application No. PCT/US2020/019050, dated Jul. 6, 2020 (16 pages).

Niitsu H, Hirabayashi N, Yoshimitsu M, etal. Using the Objective Structured Assessment of Technical Skills (OSATS) global rating scale to evaluate the skills of surgical trainees in the operating room. Surg Today. 2013;43(3):271-275. doi: 10.1007/s00595-012-OS 13-7 (Year: 2013).

Bernd Munzer et al, "Domain-Specific Video Compression for Long-term Archiving of Endoscopic Surgery Videos", 2016 IEEE International Symposium on Computer-Based Medical Systems, Jun. 20, 2016, pp. 312-317.

Stefan Petscharnig et al "Learning Laparoscopic Video Shot Classification for Gynecological Surgery", Multimed. Tools Appl., vol. 77, pp. 8061-8097 (2018).

A. Jin et al., "Tool Detection and Operative Skill Assessment in Surgical Videos Using Region-Based Convolutional Neural Networks," 2018 IEEE Winter Conference on Applications of Computer Vision (WACV), 2018, pp. 691-699, doi: 10.1109/WACV.

Hassan, A., Ghafoor, M., Tariq, S.A et al. High Efficiency Video Coding (HEVC)-Based Surgical Telementoring System Using Shallow Convolutional Neural Network. J Digit Imaging 31, 1027-1043 (2019). https://doi.org/10.1007/s10278-019-00206-2 (Year: 2019).

International Search Report and Written Opinion of the International Search Authority in PCT/IB2021/025522, dated Sep. 6, 2021.

\* cited by examiner

501

| Record Number | Procedure | Age | Gender | Medical Considerations | Time | Other Data |
|---|---|---|---|---|---|---|
| 1 | Bypass Surgery | 65 | M | Renal Disease | 4 hours | 512A 512B 512C 512D |
| 2 | Bypass Surgery | 78 | F | None | 3 hours | |

511

| Record Number | Procedure | Surgeon Name |
|---|---|---|
| 1 | Bypass Surgery | Dr. Mac |
| 2 | Bypass Surgery | Dr. Doe |

| Video Footage | Footage Location | Phase Tag | Event Location | Event Tag | Event Characteristic |
|---|---|---|---|---|---|
| LaparoscopicCholecysectomy_11_24_2019.mp4 | 0:39:02 – 1:04:36 | Calot's triangle dissection | 0:43:09 | Incision | Skill level: 8 |
| LaparoscopicCholecysectomy_11_24_2019.mp4 | 1:04:36 – 1:23:15 | Cutting of cystic duct | 1:08:39 | Incision | Skill level: 7 |
| CataractSurgery_03_11_2019.mp4 | 0:12:32 – 0:39:59 | Corneal incision | 0:22:56 | Incision | Skill level: 9 |
| ... | | | | | |

Fig. 6

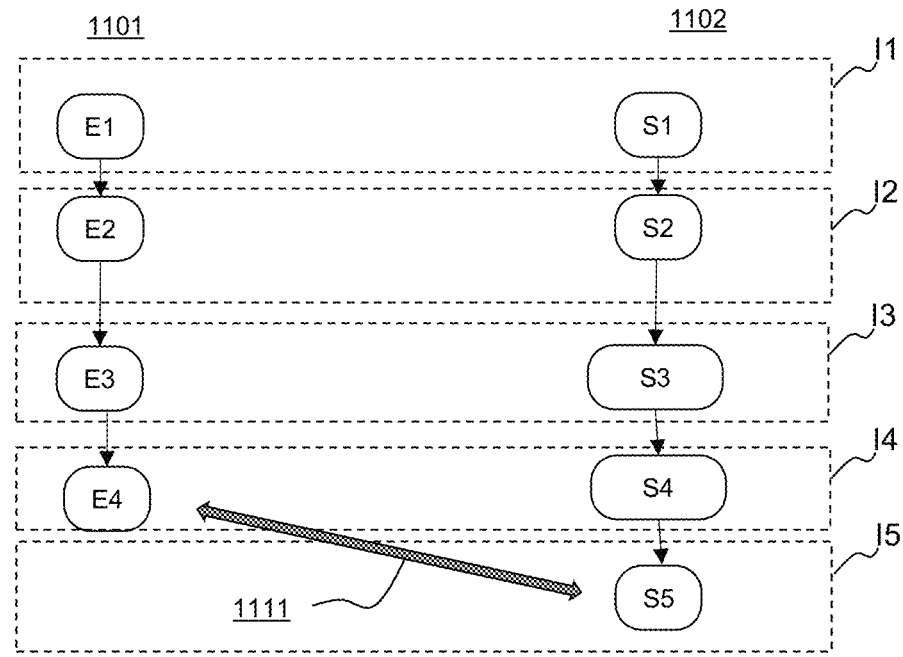
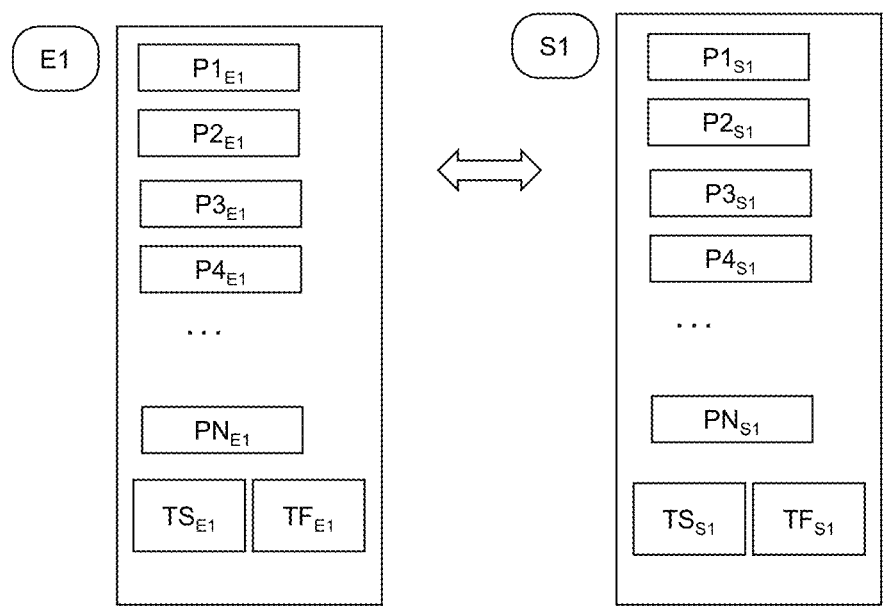
Fig. 11

1900

```
┌─────────────────────────────────────────────────────────────┐
│ RECEIVING A PLURALITY OF VIDEO FRAMES ASSOCIATED WITH AT LEAST│
│                    ONE SURGICAL PROCEDURE                    │
│                             1910                             │
└─────────────────────────────────────────────────────────────┘
                              ↓
┌─────────────────────────────────────────────────────────────┐
│        ACCESSING STORED DATA BASED ON PRIOR SURGICAL PROCEDURES│
│                             1920                             │
└─────────────────────────────────────────────────────────────┘
                              ↓
┌─────────────────────────────────────────────────────────────┐
│  PROCESSING, USING THE STORED DATA, THE PLURALITY OF VIDEO   │
│ FRAMES TO ASSESS AT LEAST ONE OF TISSUE HANDLING, ECONOMY OF │
│  MOTION, DEPTH PERCEPTION AND SURGICAL PROCEDURE FLOW IN THE │
│                   PLURALITY OF VIDEO FRAMES                  │
│                             1930                             │
└─────────────────────────────────────────────────────────────┘
                              ↓
┌─────────────────────────────────────────────────────────────┐
│  BASED ON THE ASSESSMENT OF AT LEAST ONE OF TISSUE HANDLING, │
│ ECONOMY OF MOTION, DEPTH PERCEPTION AND SURGICAL PROCEDURE   │
│  FLOW, GENERATING A COMPETENCY-RELATED SCORE FOR A SUBJECT   │
│                             1940                             │
└─────────────────────────────────────────────────────────────┘
                              ↓
┌─────────────────────────────────────────────────────────────┐
│ SELECTING, FROM THE PLURALITY OF VIDEO FRAMES, AT LEAST ONE  │
│  VIDEO CLIP FROM WHICH THE COMPETENCY SCORE WAS DERIVED      │
│                             1950                             │
└─────────────────────────────────────────────────────────────┘
                              ↓
┌─────────────────────────────────────────────────────────────┐
│                  OUTPUTTING AT LEAST ONE SCORE               │
│                             1960                             │
└─────────────────────────────────────────────────────────────┘
                              ↓
┌─────────────────────────────────────────────────────────────┐
│ PRESENTING IN ASSOCIATION WITH THE AT LEAST ONE SCORE, A LINK TO│
│                  THE AT LEAST ONE VIDEO CLIP                 │
│                             1970                             │
└─────────────────────────────────────────────────────────────┘
```

Fig. 19

SYSTEMS AND METHODS FOR PROCESSING INTEGRATED SURGICAL VIDEO COLLECTIONS TO IDENTIFY RELATIONSHIPS USING ARTIFICIAL INTELLIGENCE

CROSS-REFERENCES TO RELATED APPLICATIONS

This application is a continuation of PCT International Application No. PCT/US2021/025522, filed Apr. 2, 2021, which is based on and claims benefit of priority of U.S. Provisional Patent Application No. 63/005,348, filed Apr. 5, 2020; U.S. Provisional Patent Application No. 63/029,985, filed May 26, 2020; U.S. Provisional Patent Application No. 63/036,210 filed Jun. 8, 2020; U.S. Provisional Patent Application No. 63/041,976 filed Jun. 21, 2020; U.S. Provisional Patent Application No. 63/048,894 filed Jul. 7, 2020; U.S. Provisional Patent Application No. 63/079,326 filed Sep. 16, 2020; U.S. Provisional Patent Application No. 63/133,579 filed Jan. 4, 2021; and U.S. Provisional Patent Application No. 63/149,565 filed Feb. 15, 2021. The contents of the foregoing application are incorporated herein by reference in their entireties.

BACKGROUND

Technical Field

The disclosed embodiments generally relate to systems and methods for analysis of videos of surgical procedures.

Background Information

When performing a surgical procedure, it may be beneficial to automatically identify surgical planes or review video of previous steps or expected future steps for a surgeon to review during an ongoing surgical procedure. Furthermore, there is a need to analyze videos to automatically populate a post-operative report, or to view statistical data with links to surgical videos that substantiate the statistic. In addition, there is a need to identify patient data derived from surgical equipment location data and to assign surgical teams to prospective surgeries.

Therefore, there is a need for unconventional approaches that efficiently and effectively analyze surgical videos to enable a medical professional to receive support during an ongoing surgical procedure, view performance related statistics and data, and to facilitate scheduling and patient-data collection.

SUMMARY

Systems, methods, and computer readable media related to statistical analysis across surgical videos are disclosed. The methods may include receiving a plurality of video frames from a plurality of surgical videos of a plurality of surgical procedures performed by a specific medical professional, wherein each surgical video is associated with a differing patient. The methods may further disclose accessing a set of surgical event-related categories, wherein each surgical event-related category is denoted by a differing category indicator and analyzing the received plurality of video frames of each surgical video to identify a plurality of surgical events in each of the plurality of surgical videos, and wherein each of the identified plurality of surgical events in each of the plurality of surgical videos is defined by a differing subgroup of frames.

The method may further include assigning each differing subgroup of frames to one of the surgical event-related categories to thereby interrelate subgroups of frames from differing surgical procedures under an associated common surgical event-related category. The subgroup of frames may be associated with each surgical event-related category to derive at least one statistic associated with each subgroup of frames. Statistics may then be aggregated within each category of surgical events and displayed together with the surgical event-related categories for selection. Finally, upon receiving a selection of a particular surgical event-related category at least part of the frames assigned to the particular surgical event-related category are presented.

Systems, methods, and computer readable media related to video detection of surgical instrument deviations from a surgical plane are disclosed. Some disclosed embodiments may include receiving a plurality of video frames from a surgical video feed and analyzing at least some of the plurality of video frames to identify a surgical instrument therein. The embodiments may further involve evaluating the plurality of video frames with the identified surgical instrument therein to ascertain an interface area corresponding to a location of an interaction between the identified surgical instrument and tissue and accessing stored data characterizing a surgical plane corresponding to the location of the interaction.

The stored data may be used to determine whether the interface area is outside of the surgical plane and outputting an out-of-surgical plane signal indicating a deviation from the surgical plane by the surgical instrument.

Systems, methods, and computer readable media related to providing intraoperative video review are disclosed. They may involve receiving a plurality of video frames from a surgical video of an ongoing surgical procedure and accessing stored data based on prior surgical procedures. They may also involve predicting based on the plurality of video frames and the stored data relating to prior surgical procedures, at least one expected future event in the ongoing surgical procedure. Disclosed embodiments may also involve generating for intra-surgical presentation, at least one option to review at least one surgical video clip associated with the expected future event in the surgical procedure.

In addition, disclosed embodiments may involve accessing a data structure containing the at least one surgical video clip and outputting for intra-surgical presentation, the at least one surgical video clip associated with the expected future event.

Consistent with disclosed embodiments, systems, methods, computer readable media, and apparatus related to analyzing surgical procedures and assessing surgical competency of subjects are disclosed. Disclosed embodiments may include receiving a plurality of video frames associated with at least one surgical procedure and accessing stored data based on prior surgical procedures. Disclosed embodiments may further include processing, using the stored data, the plurality of video frames to assess at least one of tissue handling, economy of motion, depth perception and surgical procedure flow in the plurality of video frames. Based on the assessment of at least one of tissue handling, economy of motion, depth perception and surgical procedure flow, a competency-related score for a subject may be generated. Disclosed embodiments may also include selecting, from the plurality of video frames, at least one video clip from which the competency score was derived and outputting the score, and presenting in association with the at least one score, a link to the at least one video clip.

Disclosed systems, methods, and computer readable media may relate to aggregating and analyzing equipment, time, and space data to update medical records. They may involve receiving a plurality of video frames from a surgical video of an ongoing surgical procedure and accessing stored data based on prior surgical procedures. They may also involve predicting based on the plurality of video frames and the stored data relating to prior surgical procedures, at least one expected future event in the ongoing surgical procedure. Disclosed embodiments may also involve generating for intra-surgical presentation, at least one option to review at least one surgical video clip associated with the expected future event in the surgical procedure.

In addition, disclosed embodiments may involve accessing a data structure containing the at least one surgical video clip and outputting for intra-surgical presentation, the at least one surgical video clip associated with the expected future event.

Systems, methods, and computer readable media related to assigning surgical teams to prospective surgeries are disclosed. They may involve analyzing a plurality of video frames of prior surgical procedures performed by a particular surgeon to ascertain a skill level of the particular surgeon and accessing a data structure containing patient characteristics associated with the prior surgical procedures. They may also involve accessing a surgical schedule including a plurality of prospective surgical procedures overlapping in time and obtaining patient characteristics associated with the prospective surgical procedures. Disclosed embodiments may also involve analyzing the plurality of video frames of prior surgical procedures to ascertain an expected amount of time for the particular surgeon to perform at least one particular prospective surgical procedure from among the plurality of prospective surgical procedures.

In addition, disclosed embodiments may involve determining requirements for the at least one particular prospective surgical procedure, the requirements including a required skill level of a participating surgeon based on the patient characteristics associated with the at least one particular prospective surgical procedure and an expected amount of time to perform the at least one particular prospective surgical procedure. They may also involve determining whether the particular surgeon meets the requirements of the at least one particular prospective surgical procedure based on the skill level of the particular surgeon and the expected amount of time for the particular surgeon to perform the at least one particular prospective surgical procedure. Disclosed embodiments may involve outputting an indicator that the particular surgeon meets the requirements of the at least one particular prospective surgical procedure.

BRIEF DESCRIPTION OF THE DRAWINGS

FIG. 5 is a table view of an exemplary data structure consistent with disclosed embodiments.

FIG. 6 is a table view of an exemplary data structure consistent with the disclosed embodiments.

FIG. 11 shows an exemplary comparison of a sequence of events, consistent with disclosed embodiments.

FIG. 19 is a flowchart illustrating an exemplary process for analyzing a surgical procedure and assessing surgical competency of a subject, consistent with disclosed embodiments.

DETAILED DESCRIPTION

Figure 1:
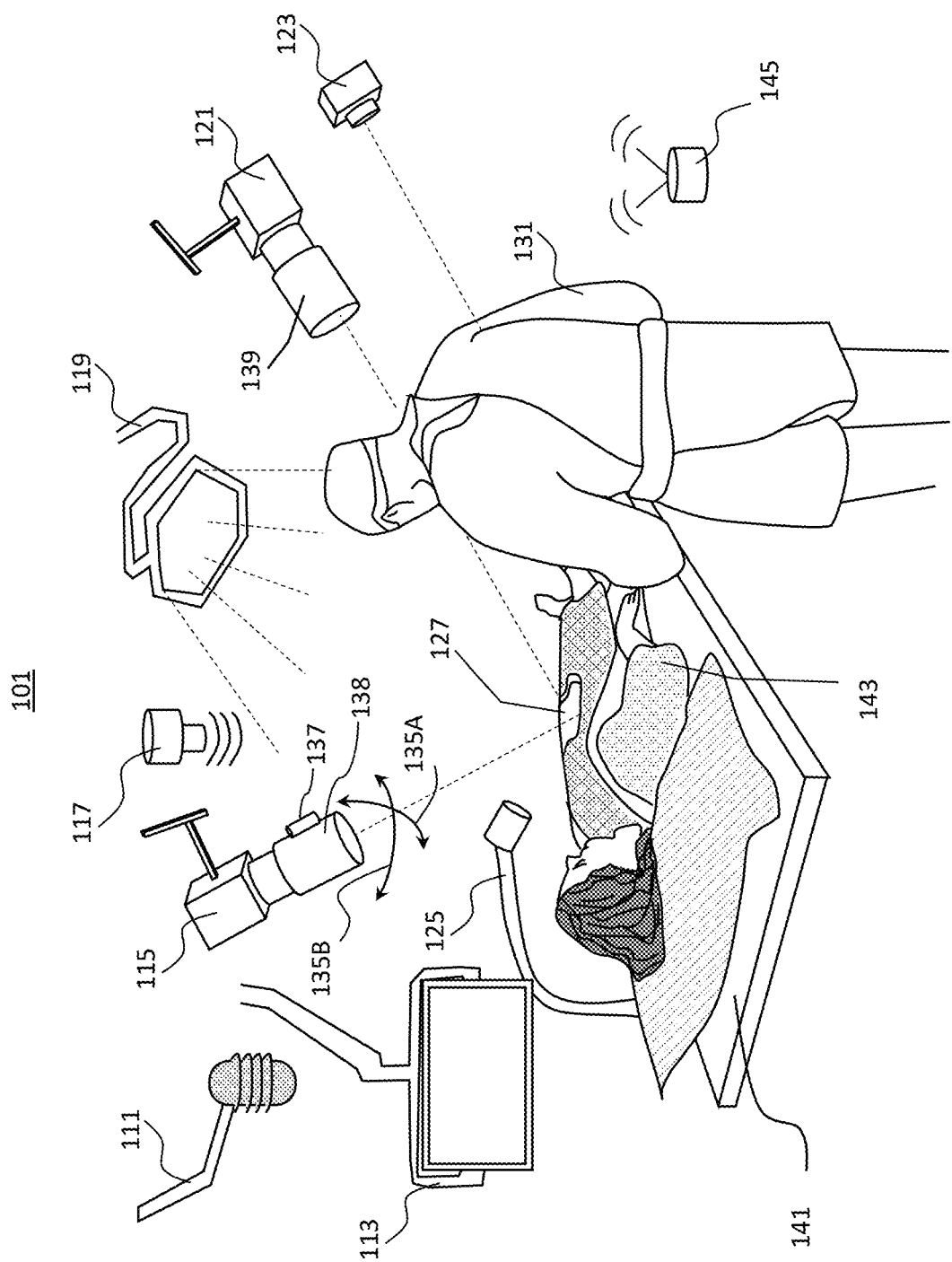
FIG. 1 is a perspective view of an example operating room, consistent with disclosed embodiments.

Unless specifically stated otherwise, as apparent from the following description, throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include actions and/or processes of a computer that manipulate and/or transform data into other data, the data represented as physical quantities, for example such as electronic quantities, and/or the data representing physical objects. The terms "computer", "processor", "controller", "processing unit", "computing unit", and "processing module" should be expansively construed to cover any kind of electronic device, component or unit with data processing capabilities, including, by way of non-limiting example, a personal computer, a wearable computer, smart glasses, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to features of "embodiments" "one case", "some cases", "other cases" or variants thereof means that a particular feature, structure or characteristic described may be included in at least one embodiment of the presently disclosed subject matter. Thus, the appearance of such terms does not necessarily refer to the same embodiment(s). As used herein, the term "and/or" includes any and all combinations of one or more of the associated listed items.

Features of the presently disclosed subject matter, are, for brevity, described in the context of particular embodiments. However, it is to be understood that features described in connection with one embodiment are also applicable to other embodiments. Likewise, features described in the context of a specific combination may be considered separate embodiments, either alone or in a context other than the specific combination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

Examples of the presently disclosed subject matter are not limited in application to the details of construction and the arrangement of the components set forth in the following description or illustrated in the drawings. The subject matter may be practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

Consistent with disclosed embodiments, "at least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Disclosed embodiments may include and/or access a data structure. A data structure consistent with the present disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Analyzing the received video frames to identify surgical events may involve any form of electronic analysis using a computing device. In some embodiments, computer image analysis may include using one or more image recognition algorithms to identify features of one or more frames of the video footage. Computer image analysis may be performed on individual frames, or may be performed across multiple frames, for example, to detect motion or other changes between frames. In some embodiments, computer image analysis may include object detection algorithms, such as Viola-Jones object detection, scale-invariant feature transform (SIFT), histogram of oriented gradients (HOG) features, convolutional neural networks (CNN), or any other forms of object detection algorithms. Other example algorithms may include video tracking algorithms, motion detection algorithms, feature detection algorithms, color-based detection algorithms, texture-based detection algorithms, shape based detection algorithms, boosting based detection algorithms, face detection algorithms, biometric recognition algorithms, or any other suitable algorithm for analyzing video frames.

In some embodiments, the computer image analysis may include using a neural network model trained using example video frames including previously identified surgical events to thereby identify a similar surgical event in a set of frames. In other words, frames of one or more videos that are known to be associated with a particular surgical event may be used to train a neural network model. The trained neural network model may therefore be used to identify whether one or more video frames are also associated with the surgical event. In some embodiments, the disclosed methods may further include updating the trained neural network model based on at least one of the analyzed frames. Accordingly, by identifying surgical events in the plurality of surgical videos using computer image analysis, disclosed embodiments create efficiencies in data processing and video classification, reduces costs through automation, and improves accuracy in data classification.

Machine learning algorithms (also referred to artificial intelligence) may be employed for the purposes of analyzing the video to identify surgical events. Such algorithms be trained using training examples, such as described below. Some non-limiting examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters may be set manually by a person or automatically by a process external to the machine learning algorithm (such as a hyper parameter search algorithm), and the parameters of the machine learning algorithm may be set by the machine learning algorithm according to the training examples. In some implementations, the hyper-parameters may be set according to the training examples and the validation examples, and the parameters may be set according to the training examples and the selected hyper-parameters.

In some embodiments, trained machine learning algorithms (e.g., artificial intelligence algorithms) may be used to analyze inputs and generate outputs, for example in the cases described below. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image. In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs. Some non-limiting examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

In some embodiments, analyzing image data (as described herein) may include analyzing the image data to obtain a preprocessed image data, and subsequently analyzing the image data and/or the preprocessed image data to obtain the desired outcome. Some non-limiting examples of such image data may include one or more images, videos, frames, footages, 2D image data, 3D image data, and so forth. One of ordinary skill in the art will recognize that the followings are examples, and that the image data may be preprocessed using other kinds of preprocessing methods. In some examples, the image data may be preprocessed by transforming the image data using a transformation function to obtain a transformed image data, and the preprocessed image data may include the transformed image data. For example, the transformed image data may include one or more convolutions of the image data. For example, the transformation function may comprise one or more image filters, such as low-pass filters, high-pass filters, band-pass filters, all-pass filters, and so forth. In some examples, the transformation function may include a nonlinear function. In some examples, the image data may be preprocessed by smoothing at least parts of the image data, for example using Gaussian convolution, using a median filter, and so forth. In some examples, the image data may be preprocessed to obtain a different representation of the image data. For example, the preprocessed image data may include: a representation of at least part of the image data in a frequency domain; a Discrete Fourier Transform of at least part of the image data; a Discrete Wavelet Transform of at least part of the image data; a time/frequency representation of at least part of the image data; a representation of at least part of the image data in a lower dimension; a lossy representation of at least part of the image data; a lossless representation of at least part of the image data; a time ordered series of any of the above; any combination of the above; and so forth. In some examples, the image data may be preprocessed to extract edges, and the preprocessed image data may include information based on and/or related to the extracted edges. In some examples, the image data may be preprocessed to extract image features from the image data. Some non-limiting examples of such image features may comprise information based on and/or related to: edges; corners; blobs; ridges; Scale Invariant Feature Transform (SIFT) features; temporal features; and so forth.

In some embodiments, analyzing image data (for example, by the methods, steps and processor function described herein) may include analyzing the image data and/or the preprocessed image data using one or more rules, functions, procedures, artificial neural networks, object detection algorithms, anatomical detection algorithms, visual event detection algorithms, action detection algorithms, motion detection algorithms, background subtraction algorithms, inference models, and so forth. Some non-limiting examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth.

In some embodiments, analyzing image data (for example, by the methods, steps and processor function described herein) may include analyzing pixels, voxels, point cloud, range data, etc. included in the image data.

Aspects of this disclosure may relate to surgical procedures performed in operating rooms. FIG. 1 shows an example operating room 101, consistent with disclosed embodiments. A patient 143 is illustrated on an operating table 141. Room 101 may include audio sensors, video/image sensors, chemical sensors, and other sensors, as well as various light sources (e.g., light source 119 is shown in FIG. 1) for facilitating the capture of video and audio data, as well as data from other sensors, during the surgical procedure. For example, room 101 may include one or more microphones (e.g., audio sensor 111, as shown in FIG. 1), several cameras (e.g., overhead cameras 115, 121, and 123, and a tableside camera 125) for capturing video/image data during surgery. While some of the cameras (e.g., cameras 115, 123 and 125) may capture video/image data of operating table 141 (e.g., the cameras may capture the video/image data at a location 127 of a body of patient 143 on which a surgical procedure is performed), camera 121 may capture video/image data of other parts of operating room 101. For instance, camera 121 may capture video/image data of a surgeon 131 performing the surgery. In some cases, cameras may capture video/image data associated with surgical team personnel, such as an anesthesiologist, nurses, surgical tech and the like located in operating room 101. Additionally, operating room cameras may capture video/image data associated with medical equipment located in the room.

In various embodiments, one or more of cameras 115, 121, 123 and 125 may be movable. For example, as shown in FIG. 1, camera 115 may be rotated as indicated by arrows 135A showing a pitch direction, and arrows 135B showing a yaw direction for camera 115. In various embodiments, pitch and yaw angles of cameras (e.g., camera 115) may be electronically controlled such that camera 115 points at a region-of-interest (ROI), of which video/image data needs to be captured. For example, camera 115 may be configured to track a surgical instrument (also referred to as a surgical tool) within location 127, an anatomical structure, a hand of surgeon 131, an incision, a movement of anatomical structure, and the like. In various embodiments, camera 115 may be equipped with a laser 137 (e.g., an infrared laser) for precision tracking. In some cases, camera 115 may be tracked automatically via a computer-based camera control application that uses an image recognition algorithm for positioning the camera to capture video/image data of a ROI. For example, the camera control application may identify an anatomical structure, identify a surgical tool, hand of a surgeon, bleeding, motion, and the like at a particular location within the anatomical structure, and track that location with camera 115 by rotating camera 115 by appropriate yaw and pitch angles. In some embodiments, the camera control application may control positions (i.e., yaw and pitch angles) of various cameras 115, 121, 123 and 125 to capture video/image date from different ROIs during a surgical procedure. Additionally or alternatively, a human operator may control the position of various cameras 115, 121, 123 and 125, and/or the human operator may supervise the camera control application in controlling the position of the cameras.

Cameras 115, 121, 123 and 125 may further include zoom lenses for focusing in on and magnifying one or more ROIs. In an example embodiment, camera 115 may include a zoom lens 138 for zooming closely to a ROI (e.g., a surgical tool in the proximity of an anatomical structure). Camera 121 may include a zoom lens 139 for capturing video/image data from a larger area around the ROI. For example, camera 121 may capture video/image data for the entire location 127. In some embodiments, video/image data obtained from camera 121 may be analyzed to identify a ROI during the surgical procedure, and the camera control application may be configured to cause camera 115 to zoom towards the ROI identified by camera 121.

In various embodiments, the camera control application may be configured to coordinate the position, focus, and magnification of various cameras during a surgical procedure. For example, the camera control application may direct camera 115 to track an anatomical structure and may direct camera 121 and 125 to track a surgical instrument. Cameras 121 and 125 may track the same ROI (e.g., a surgical instrument) from different view angles. For example, video/image data obtained from different view angles may be used to determine the position of the surgical instrument relative to a surface of the anatomical structure, to determine a condition of an anatomical structure, to determine pressure applied to an anatomical structure, or to determine any other information where multiple viewing angles may be beneficial. By way of another example, bleeding may be detected by one camera, and one or more other cameras may be used to identify the source of the bleeding.

In various embodiments, control of position, orientation, settings, and/or zoom of cameras 115, 121, 123 and 125 may be rule-based and follow an algorithm developed for a given surgical procedure. For example, the camera control application may be configured to direct camera 115 to track a surgical instrument, to direct camera 121 to location 127, to direct camera 123 to track the motion of the surgeon's hands, and to direct camera 125 to an anatomical structure. The algorithm may include any suitable logical statements determining position, orientation, settings and/or zoom for cameras 115, 121, 123 and 125 depending on various events during the surgical procedure. For example, the algorithm may direct at least one camera to a region of an anatomical structure that develops bleeding during the procedure. Some non-limiting examples of settings of cameras 115, 121, 123 and 125 that may be controlled (for example by the camera control application) may include image pixel resolution, frame rate, image and/or color correction and/or enhancement algorithms, zoom, position, orientation, aspect ratio, shutter speed, aperture, focus, and so forth.

In various cases, when a camera (e.g., camera 115) tracks a moving or deforming object (e.g., when camera 115 tracks a moving surgical instrument, or a moving/pulsating anatomical structure), a camera control application may determine a maximum allowable zoom for camera 115, such that the moving or deforming object does not escape a field of view of the camera. In an example embodiment, the camera control application may initially select the first zoom for camera 115, evaluate whether the moving or deforming object escapes the field of view of the camera, and adjust the zoom of the camera as necessary to prevent the moving or deforming object from escaping the field of view of the camera. In various embodiments, the camera zoom may be readjusted based on a direction and a speed of the moving or deforming object.

Figure 2:
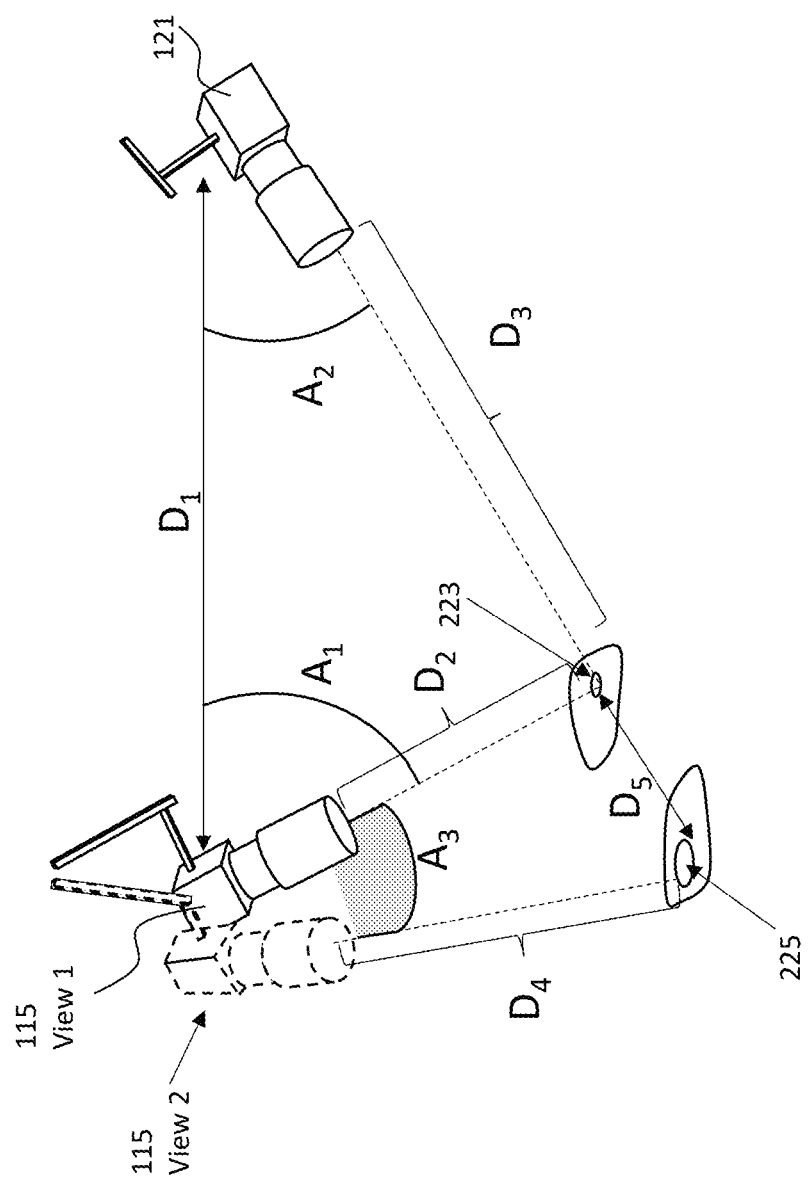
FIG. 2 is a perspective view of an exemplary camera arrangement, consistent with disclosed embodiments.

In various embodiments, one or more image sensors may include moving cameras 115, 121, 123 and 125. Cameras 115, 121, 123 and 125 may be used for determining sizes of anatomical structures and determining distances between different ROIs, for example using triangulation. For example, FIG. 2 shows exemplary cameras 115 (115 View 1, as shown in FIG. 2) and 121 supported by movable elements such that the distance between the two cameras is D1, as shown in FIG. 2. Both cameras point at ROI 223. By knowing the positions of cameras 115 and 121 and the direction of an object relative to the cameras (e.g., by knowing angles A1 and A2, as shown in FIG. 2, for example based on correspondences between pixels depicting the same object or the same real-world point in the images captured by 115 and 121), distances D2 and D3 may be calculated using, for example, the law of sines and the known distance between the two cameras D1. In an example embodiment, when camera 115 (115, View 2) rotates by a small angle A3 (measured in radians), to point at ROI 225, the distance between ROI 223 and ROI 225 may be approximated (for small angles A3) by A3D2. More accuracy may be obtained using another triangulation process. Knowing distances between ROI 223 and 225 allows determining a length scale for an anatomical structure. Further, distances between various points of the anatomical structure, and distances from the various points to one or more cameras may be measured to determine a point-cloud representing a surface of the anatomical structure. Such a point-cloud may be used to reconstruct a three-dimensional model of the anatomical structure. Further, distances between one or more surgical instruments and different points of the anatomical structure may be measured to determine proper locations of the one or more surgical instruments in the proximity of the anatomical structure. In some other examples, one or more of cameras 115, 121, 123 and 125 may include a 3D camera (such as a stereo camera, an active stereo camera, a Time of Flight camera, a Light Detector and Ranging camera, etc.), and actual and/or relative locations and/or sizes of objects within operating room 101, and/or actual distances between objects, may be determined based on the 3D information captured by the 3D camera.

Returning to FIG. 1, light sources (e.g., light source 119) may also be movable to track one or more ROIs. In an example embodiment, light source 119 may be rotated by yaw and pitch angles, and in some cases, may extend towards to or away from a ROI (e.g., location 127). In some cases, light source 119 may include one or more optical elements (e.g., lenses, flat or curved mirrors, and the like) to focus light on the ROI. In some cases, light source 119 may be configured to control the color of the light (e.g., the color of the light may include different types of white light, a light with a selected spectrum, and the like). In an example embodiment, light 119 may be configured such that the spectrum and intensity of the light may vary over a surface of an anatomic structure illuminated by the light. For example, in some cases, light 119 may include infrared wavelengths which may result in warming of at least some portions of the surface of the anatomic structure.

In some embodiments, the operating room may include sensors embedded in various components depicted or not depicted in FIG. 1. Examples of such sensors may include: audio sensors; image sensors; motion sensors; positioning sensors; chemical sensors; temperature sensors; barometers; pressure sensors; proximity sensors; electrical impedance sensors; electrical voltage sensors; electrical current sensors; or any other detector capable of providing feedback on the environment or a surgical procedure, including, for example, any kind of medical or physiological sensor configured to monitor patient 143.

In some embodiments, the operating room may include a wireless transmitter 145, capable of transmitting a location identifier, as illustrated in FIG. 1. The wireless transmitter may communicate with other elements in the operating room through wireless signals, such as radio communication including Bluetooth or Wireless USB, Wi-Fi, LPWAN, RFID, or other suitable wireless communication methods. In some embodiments, wireless transmitter 145 may be a receiver or transceiver. Accordingly, wireless transmitter 145 may be configured to receive signals for the purpose of determining a location of elements in the operating room. Although FIG. 1 depicts only one wireless transmitter 145, embodiments may include additional wireless transmitters. For example, a wireless transmitter may be associated with a particular patient, a particular doctor, an operating room, a piece of equipment, or any other object, place, or person. Wireless transmitter 145 may be attached to equipment, a room, or a person. For example, wireless transmitter 145 may be a wearable device or a component of a wearable device. In some embodiments, wireless transmitter 145 may be mounted to a wall or a ceiling. Generally, wireless transmitter 145 may be a standalone device or may be a component of device. For example, wireless transmitter 145 may be a component of a piece of medical equipment, a camera, a personal mobile device, or another system associated with a surgery. Additionally or alternatively, wireless transmitter 145 may be an active or a passive wireless tag, a wireless location beacon, and so forth.

In some embodiments, audio sensor 111 may include one or more audio sensors configured to capture audio by converting sounds to digital information (e.g., audio sensors 121).

In various embodiments, temperature sensors may include infrared cameras (e.g., an infrared camera 117 is shown in FIG. 1) for thermal imaging. Infrared camera 117 may allow measurements of the surface temperature of an anatomic structure at different points of the structure. Similar to visible cameras D115, 121, 123 and 125, infrared camera 117 may be rotated using yaw or pitch angles. Additionally or alternatively, camera 117 may include an image sensor configured to capture image from any light spectrum, include infrared image sensor, hyper-spectral image sensors, and so forth.

FIG. 1 includes a display screen 113 that may show views from different cameras 115, 121, 123 and 125, as well as other information. For example, display screen 113 may show a zoomed-in image of a tip of a surgical instrument and a surrounding tissue of an anatomical structure in proximity to the surgical instrument.

Figure 3:
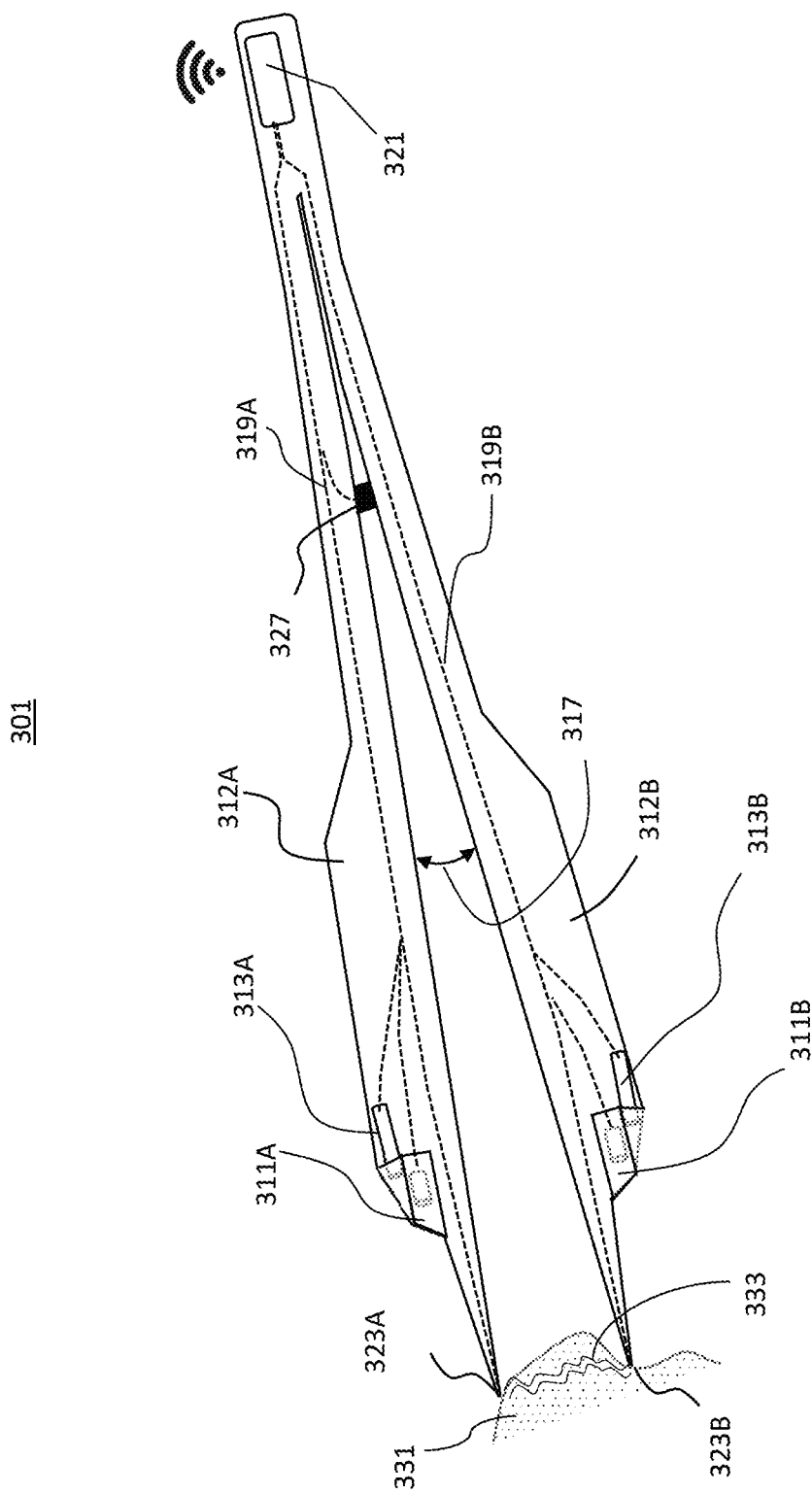
FIG. 3 is a perspective view of an example of a surgical instrument, that may be used in connection with disclosed embodiments.

FIG. 3 shows an example embodiment of a surgical instrument 301 that may include multiple sensors and light-emitting sources. Consistent with the present embodiments, a surgical instrument may refer to a medical device, a medical instrument, an electrical or mechanical tool, a surgical tool, a diagnostic tool, and/or any other instrumentality that may be used during a surgery. As shown, instrument 301 may include cameras 311A and 311B, light sources 313A and 313B as well as tips 323A and 323B for contacting tissue 331. Cameras 311A and 311B may be connected via data connection 319A and 319B to a data transmitting device 321. In an example embodiment, device 321 may transmit data to a data-receiving device using a wireless communication or using a wired communication. In an example embodiment, device 321 may use WiFi, Bluetooth, NFC communication, inductive communication, or any other suitable wireless communication for transmitting data to a data-receiving device. The data-receiving device may include any form of receiver capable of receiving data transmissions. Additionally or alternatively, device 321 may use optical signals to transmit data to the data-receiving device (e.g., device 321 may use optical signals transmitted through the air or via optical fiber). In some embodiments, device 301 may include local memory for storing at least some of the data received from sensors 311A and 311B. Additionally, device 301 may include a processor for compressing video/image data before transmitting the data to the data-receiving device.

In various embodiments, for example when device 301 is wireless, it may include an internal power source (e.g., a battery, a rechargeable battery, and the like) and/or a port for recharging the battery, an indicator for indicating the amount of power remaining for the power source, and one or more input controls (e.g., buttons) for controlling the operation of device 301. In some embodiments, control of device 301 may be accomplished using an external device (e.g., a smartphone, tablet, smart glasses) communicating with device 301 via any suitable connection (e.g., WiFi, Bluetooth, and the like). In an example embodiment, input controls for device 301 may be used to control various parameters of sensors or light sources. For example, input controls may be used to dim/brighten light sources 313A and 313B, move the light sources for cases when the light sources may be moved (e.g., the light sources may be rotated using yaw and pitch angles), control the color of the light sources, control the focusing of the light sources, control the motion of cameras 311A and 311B for cases when the cameras may be moved (e.g., the cameras may be rotated using yaw and pitch angles), control the zoom and/or capturing parameters for cameras 311A and 311B, or change any other suitable parameters of cameras 311A-311B and light sources 313A-313B. It should be noted camera 311A may have a first set of parameters and camera 311B may have a second set of parameters that is different from the first set of parameters, and these parameters may be selected using appropriate input controls. Similarly, light source 313A may have a first set of parameters and light source 313B may have a second set of parameters that is different from the first set of parameters, and these parameters may be selected using appropriate input controls.

Additionally, instrument 301 may be configured to measure data related to various properties of tissue 331 via tips 323A and 323B and transmit the measured data to device 321. For example, tips 323A and 323B may be used to measure the electrical resistance and/or impedance of tissue 331, the temperature of tissue 331, mechanical properties of tissue 331 and the like. To determine elastic properties of tissue 331, for example, tips 323A and 323B may be first separated by an angle 317 and applied to tissue 331. The tips may be configured to move such as to reduce angle 317, and the motion of tips may result in pressure on tissue 331. Such pressure may be measured (e.g., via a piezoelectric element 327 that may be located between a first branch 312A and a second branch 312B of instrument 301), and based on the change in angle 317 (i.e., strain) and the measured pressure (i.e., stress), the elastic properties of tissue 331 may be measured. Furthermore, based on angle 317 distance between tips 323A and 323B may be measured, and this distance may be transmitted to device 321. Such distance measurements may be used as a length scale for various video/image data that may be captured by various cameras 115, 121, 123 and 125, as shown in FIG. 1.

Instrument 301 is only one example of possible surgical instrument, and other surgical instruments such as scalpels, graspers (e.g., forceps), clamps and occluders, needles, retractors, cutters, dilators, suction tips, and tubes, sealing devices, irrigation and injection needles, scopes and probes, and the like, may include any suitable sensors and light-emitting sources. In various cases, the type of sensors and light-emitting sources may depend on a type of surgical instrument used for a surgical procedure. In various cases, these other surgical instruments may include a device similar to device 301, as shown in FIG. 3, for collecting and transmitting data to any suitable data-receiving device.

Aspects of the present disclosure may involve medical professionals performing surgical procedures. A medical professional may include, for example, a surgeon, a surgical technician, a resident, a nurse, a physician's assistant, an anesthesiologist, a doctor, a veterinarian surgeon, and so forth. A surgical procedure may include any set of medical actions associated with or involving manual or operative activity on a patient's body. Surgical procedures may include one or more of surgeries, repairs, ablations, replacements, implantations, implantations, extractions, treatments, restrictions, re-routing, and blockage removal, or may include veterinarian surgeries. Such procedures may involve cutting, abrading, suturing, extracting, lancing or any other technique that involves physically changing body tissues and/or organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally Invasive surgery for intracerebral hemorrhage evacuation, or any other medical procedure involving some form of incision. While the present disclosure is described in reference to surgical procedures, it is to be understood that it may also apply to other forms of medical procedures, or procedures generally.

Aspects of the present disclosure relate to systems and methods for selecting and processing video collections using artificial intelligence to identify relationships. Disclosed systems and methods may involve using artificial intelligence to automatically detect events by analyzing frames of surgical procedures assigning categories to thereby interrelate subgroups of frames from differing surgical procedures under an associated common surgical event-related category.

In analysis of surgical videos, identifying surgical events and generating and aggregating statistics associated with those events can be a daunting task due to the volume of video information and statistical data available. For example, thousands of statistics can be generated across thousands of surgical videos leading to an unorganized, inefficiently managed, and unsearchable data set. Humans may be unable to efficiently detect and organize all of this information due to limitations in perception or availability of labor hours. Furthermore, presentation of statistical data alone without a link to supporting video evidence of the statistic can lead to confusion.

Therefore, there is a need for unconventional approaches that enable users to receive a presentation of video frames associated with various surgical statistics, the statistics identified, aggregated, and assigned to the video frames through machine learning enabled video processing techniques to provide solutions for detecting events otherwise undetectable by a human and to create new data structures which are indexable, searchable, efficiently organized, and presented across a wide variety of platforms and multiple devices.

Aspects of this disclosure may relate to using machine learning to solve problems in the field of video processing. For example, aspects of this disclosure provide solutions for detecting events otherwise undetectable by a human and create new data structures which may be indexable, searchable, and efficiently organized across a wide variety of platforms and multiple devices.

Aspects of this disclosure may relate to statistical analysis operations. Statistical analysis operations may include collecting, organizing, analyzing, interpreting, or presenting data. Statistical analysis may include data analysis or data processing.

For ease of discussion, a method is described below with the understanding that aspects of the method apply equally to systems, devices, and computer readable media. For example, some aspects of such a method may occur electronically over a network that may be either wired, wireless, or both. Other aspects of such a method may occur using non-electronic means. In a broadest sense, the method is not limited to particular physical and/or electronic instrumentalities, but rather may be accomplished using many differing instrumentalities.

Disclosed embodiments may involve performing statistical analysis operations across a plurality of videos. A plurality of videos may include a number of portions of one or more surgical procedures captured in motion picture. The portions may represent an entire surgical procedure, a subset of frames from a single surgical procedure, or subsets of frames from differing surgical procedures. The plurality of videos may be located in and accessed from a repository of a plurality of sets of surgical video footage. As used herein, a repository may refer to any data storage location or set of storage locations where video footage may be stored for retrieval. For example, the repository may include a memory device, such as one or more servers, a hard drive and/or flash drive or any other mechanism for storing data. In some embodiments, the repository may be a network location such as a networked server, a cloud storage location, a shared network drive, or any other form of storage accessible over a network. The repository may include a database of surgical video footage captured at various times and/or locations. In some embodiments, the repository may store additional data in addition to the surgical video footage.

Disclosed embodiments may involve receiving a plurality of video frames from a plurality of surgical videos. Surgical videos may refer to any video, group of video frames, or video footage including representations of a surgical procedure. For example, the surgical video may include one or more video frames captured during a surgical operation. In another example, the surgical video may include one or more video frames captured from within a surgical cavity, for example using a camera positioned the body of the patient. A plurality of video frames may refer to a grouping of frames from one or more surgical videos or surgical video clips. The video frames may be stored in a common location or may be stored in a plurality of differing storage locations. Although not necessarily so, video frames within a received group may be related in some way. For example, video frames within a set may include frames, recorded by the same capture device, recorded at the same facility, recorded at the same time or within the same timeframe, depicting surgical procedures performed on the same patient or group of patients, depicting the same or similar surgical procedures, or sharing any other properties or characteristics. Alternatively, one or more video frames may be captured at different times from surgical procedures performed on differing patients.

The plurality of sets of surgical video footage may reflect a plurality of surgical procedures performed by a specific medical professional. A specific medical professional may include, for example, a specific surgeon, a specific surgical technician, a specific resident, a specific nurse, a specific physician's assistant, a specific anesthesiologist, a specific doctor, a specific veterinarian surgeon, and so forth. A surgical procedure may include any set of medical actions associated with or involving manual or operative activity on a patient's body. Surgical procedures may include one or more of surgeries, repairs, ablations, replacements, implantations, implantations, extractions, treatments, restrictions, re-routing, and blockage removal. Such procedures may involve cutting, abrading, suturing, extracting, lancing or any other technique that involves physically changing body tissues and/or organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally Invasive surgery for intracerebral hemorrhage evacuation, or any other medical procedure involving some form of incision. While the present disclosure is described in reference to surgical procedures, it is to be understood that it may also apply to other forms of medical procedures, or procedures generally.

A surgical procedure may be performed by a specific medical professional, such as a surgeon, a surgical technician, a resident, a nurse, a physician's assistant, an anesthesiologist, a doctor, a veterinarian surgeon, or any other healthcare professional. It is often desirable to track performance of a specific medical professional over a wide range of time periods or procedures, but such analysis may be difficult because often no record exists of performance, and even when video is captured, meaningful analysis over time is typically not humanly possible. This is due to the fact that surgical procedures tend to be extended in time, with portions of interest from an analytical perspective being buried within high volumes of extraneous frames. It would be unworkable for a human to review hours of video, identifying and isolating similar frames from differing surgical procedures, let alone performing meaningful comparative analysis. Accordingly, disclosed embodiments enable analysis of surgical events or surgical outcomes related to specific medical professionals. A medical professional may have one or more of a number of characteristics, such as an age, a sex, an experience level, a skill level, or any other measurable characteristic. The specific medical professional may be identified automatically using computer image analysis, such as facial recognition or other biometric recognition methods. Alternatively or additionally, the specific medical professional may be identified using metadata, tags, labels, or other classification information associated with videos or contained in an associated electronic medical record. In some embodiments, the specific medical professional may be identified based on user input and/or a database containing identification information related to medical professionals.

The plurality of surgical video frames may be associated with differing patients. For example, a number of different patients who underwent the same or similar surgical procedure, or who underwent surgical procedures where a similar technique was employed may be included within a common set or a plurality of sets. Alternatively or in addition, one or more sets may include surgical footage captured from a single patient but at different times or from different image capture devices. The plurality of surgical procedures may be of the same type, for example, all including appendectomies, or may be of different types. In some embodiments, the plurality of surgical procedures may share common characteristics, such as the same or similar phases or intraoperative events. As referred to in this paragraph, each video of the plurality of surgical videos may be associated with a differing patient. That is, if the plurality may include only two videos, each video may be from a differing patient. If the plurality of videos includes more than two videos, it is sufficient that videos reflect surgical procedures performed on at least two differing patients.

Some aspects of the present disclosure may involve accessing a set of surgical event-related categories, wherein each surgical event-related category may be denoted by a differing category indicator. A surgical event-related category may include any classification or label associated with the surgical event. Some non-limiting examples of such categories may include a procedure step, a safety milestone, a point of decision, an intraoperative event, an operative milestone or an intraoperative decision. A surgical event-related category indicator may include any sign, pointer, tag, or code identifying a surgical event-related category. In one sense, the category indicator may be the full name of, or an abbreviation of the category. In other embodiments, the category indicator may be a code or tag mapped to the surgical event or an occurrence within the surgical event. Surgical event-related category indicators may be stored in a database or data structure. By storing or using surgical event-related category indicators, disclosed embodiments solve problems in the field of statistical analysis by creating standardized uniform classification labels for data points, allowing data to be structured and stored in systematic and organized ways to improve efficiency and accuracy in data analysis.

In some embodiments, analyzing the received video frames of each surgical video may include identifying surgical events in each of a plurality of surgical videos. Identification of a plurality of surgical events in each of the plurality of surgical videos may include performing computer image analysis on frames of the video footage to identify at least one surgical event, such as a procedure step, a safety milestone, a point of decision, an intraoperative event, an operative milestone, or an intraoperative decision. For example, analyzing the received plurality of video frames may include identifying an incision, a fluid leak, excessive bleeding, or any other surgical event. Identified surgical events in surgical videos may defined by differing subgroup of frames. Alternatively or additionally, the identified plurality of surgical events may include overlapping subgroups of frames (e.g., two subgroups may share at least one common frame). For example, a subgroup of frames may relate to a surgical action, such as an incision procedure, and an overlapping subgroup of frames to an adverse event such as a fluid leakage event. Analyzing the received video frames to identify surgical events may involve any form of electronic analysis using a computing device including computer image analysis and artificial intelligence.

In some embodiments, analyzing the plurality of video frames may include analyzing the plurality of video frames to determine an average skill of a category of physicians. Analyzing may be performed using the methodology described previously. For example, various statistics can be derived though analysis of a set of frames associated with a category of physician. In one example, one or more convolutions of at least part of the plurality of video frames may be calculated, and the average skill of the category of physicians may be determined based on the calculated one or more convolutions. For instance, frames associated with multiple surgeons can be analyzed to identify properties or events, such as hand-eye coordination, excessive bleeding amount, incision techniques, stitching techniques, appropriate incision placement, dissection, hemostasis, tissue handling skills, or a length of time to complete a surgical event. An average skill can be determined for a category of physicians through analysis of the presence or absence of certain surgical events, through the length of time associated with the performance of a surgical event, or through detection of techniques used and comparison with skill criteria derived through a learning model trained on prior videos. In this way, an average skill may be determined by the system. The average skill may be based on any one or more of the criteria discussed above.

Further embodiments may include presenting an interface enabling the specific physician to self-compare with the average skill. The interface may be a graphical user interface, e.g., user interface 700, such as on a display of a computing device. Presenting an interface may include outputting code from at least one processor, wherein the code may be configured to cause the interface to be presented. Consistent with the disclosure above, a skill score or other measure may be calculated for the specific physician and may be displayed alongside an average score or measure for the category of physicians. For example, a specific score may be calculated for a surgeon's skill in hiatal repair, wrap creation, fundus mobilization, esophageal mobilization, or other type of surgical procedure. The specific physician score in one or more surgical categories may be displayed alongside the average score for the category of physicians. In some embodiments, the specific physician score and the average score may be displayed via alphanumeric text. In other embodiments, the specific physician score and the average score may be displayed graphically. One or more scores may be displayed simultaneously either through alphanumeric text or graphically.

In some embodiments, the operations may further include receiving a selection via a user interface of a category of physicians for comparison. Receiving a selection may occur through any data input mechanism, such as, for example, a graphical user interface, such as on a display of a computing device, a keyboard, a computer mouse, a trackpad, and so forth. In another example, the selection may occur through a touch screen. In an additional example, the selection may occur through voice input, and the voice input may be processed using a speech recognition algorithm. In yet another example, the selection may occur through gestures (such as hand gestures), and the gestures may be analyzed using gesture recognition algorithms. The selection of a category of physicians may be a selection of one or more characteristic of any group of physicians. Such selections may include experience level, years practicing, industry rating, place of employment, number of procedures performed, or any other metric depending on system design choice. In some embodiments a physician or an administrator may select multiple criteria (e.g., Y years practicing in a particular hospital and having performed N procedures.) In some embodiments, the user interface may be configured to permit selection from a group consisting of at least two of a division, a department, a hospital, a demographic, and literature. For example, a user may select all orthopedic surgeons in a particular hospital. In other example, a class of residents in the same academic year may be selected. It will be appreciated that multiple selection combinations are apparent and are not limited to these examples.

Some aspects of the present disclosure may include assigning each differing subgroup of frames to one of the surgical event-related categories to thereby interrelate subgroups of frames from differing surgical procedures under an associated common surgical event-related category. Any suitable means may be used to assign the subgroup of frames to one of the surgical event-related categories. Assignment of a subgroup of frames to one of the surgical event-related categories may occur through manual user input or through computer image analysis trained using a neural network model or other trained machine learning algorithm.

In some examples, subgroups of frames from differing surgical procedures may be assigned to common surgical event-related categories through computer image analysis trained with a machine learning algorithm. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image (such as an estimated property of the item, such as size, volume, age of a person depicted in the image, cost of a product depicted in the image, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

Assignment of a subgroup of frames may generate tags or labels associated with the frames. For example, tags may correspond to differing surgical event-related categories, such as a procedure step, a safety milestone, a point of decision, an intraoperative event, an operative milestone, or an intraoperative decision. Tags may include a timestamp, time range, frame number, or other means for associating the surgical event-related category to the subgroup of frames. In other embodiments, the tag may be associated with the subgroup of frames in a database. For example, the database may include information linking the surgical event-related category to the video frames and to the particular video footage location. The database may include a data structure, as described in further detail herein.

Some embodiments may include evaluating each subgroup of frames associated with each surgical event-related category to derive at least one statistic associated with each subgroup of frames. Evaluating may involve the computer analysis/artificial intelligence described above. When performed, the evaluating may derive any number of statistics or statistical data from a subgroup of frames. Statistical data may include average values, data trends, standard deviations, variances, correlations, causal relations, test statistics (including t statistics, chi-squared statistics, f statistics, or other forms of test statistics), order statistics (including sample maximum and minimum), graphical representations (e.g., charts, graphs, plots, or other visual or graphical representations), or similar data. Evaluating subgroups of frames associated with surgical event-related categories may include performing computer image analysis on the video footage to derive at least one statistic associated with a subgroup of frames. For example, computer image analysis may indicate a quantity of intraoperative events, such as an incision or a fluid leak, or it may indicate a length of time associated with an aspect of a procedure. Using computer image analysis to derive statistics from the subgroup of frames creates efficiencies, improves accuracy, and reduces labor costs through automation of the deriving of the statistic. In addition, computer image analysis may detect and derive statistics that are undetectable through ordinary surgical observations due to improved efficiencies.

For example, the statistical information may describe relationships between or within aspects of a surgical-event related category. Statistical information may refer to any information that may be useful to analyze multiple surgical procedures together. Statistical information may include, but is not limited to, average values, data trends, standard deviations, variances, correlations, causal relations, test statistics (including t statistics, chi-squared statistics, f statistics, or other forms of test statistics), order statistics (including sample maximum and minimum), graphical representations (e.g., charts, graphs, plots, or other visual or graphical representations), or similar descriptive data. For example, the statistical information may be received from a user, may be read from memory, may be received from an external device, may be generated using computer image analysis (for example as described herein), and so forth. In some examples, the statistical information may be provided to a user, for example through a visual user interface, audibly, and so forth. As an illustrative example, in embodiments where the user selects a surgical event-related category including the identity of a particular surgeon, the statistical information may include the average duration in which the surgeon performs the surgical event, the rate of adverse or other outcomes the surgeon, the average skill level at which the surgeon performs an intraoperative event, or similar statistical information. Statistical data may be derived from frames associated with the specific medical professional, or they may be derived from frames associated with other medical professionals as described herein.

Some embodiments may include aggregating each statistic within each category of surgical events. Aggregating a statistic may refer to collecting data and combining it from multiple sources. The aggregated statistics may be compiled from multiple surgical events having some relation to a particular surgical event. A surgical event may be considered similar to the particular surgical event if it includes the same or similar procedure steps, safety milestones, points of decisions, intraoperative events, operative milestones, or intraoperative decisions. For example, statistics quantifying an intraoperative event, such as a fluid leak, may be derived from multiple surgical videos associated with differing patients. The derived statistics may be aggregated into a composite statistic. The creation of aggregate statistics may solve problems in the medical field by linking disparate data points into a summary aggregated statistic which improves analysis of a medical professional's performance across multiple surgeries and patients.

Some aspects of the present disclosure may involve displaying the surgical event-related categories for selection together with the aggregated statistic for each surgical event-related category. Displaying the surgical event-related categories for selection together with the aggregated statistic may be performed for example through a visual user interface, e.g., user interface 700, audibly, or through any other mechanism for providing information to a user. By way of example, a surgical event-related category such as an intraoperative event may be displayed alongside a statistic associated with that event. For instance, an intraoperative event such as gallbladder bile leak may be displayed alongside a statistic representing a quantity of such gallbladder bile leaks performed by that medical professional. Other non-exclusive examples include displaying statistical quantities adjacent to an intraoperative event, such as a number of pus spillages, a number of cystic duct 'mud' spillage. Other non-limiting examples may include displaying a decision point along with a quantity representing a number of correct or incorrect decisions made by the medical professional.

In some embodiments, displaying the surgical event-related categories for selection together with the aggregate statistic for each surgical event-related category may include displaying in a juxtaposed manner, statistics of the specific medical professional and statistics of at least one of the other medical professionals. A juxtaposed manner may include displaying information from two medical professionals in a side-by-side fashion, in a table, in a graph, or in another visual arrangement that compares data between the professionals. This display allows a medical professional to compare his or her statistics against statistics of other medical professionals. For example, the display may depict a quantity of fluid leaks associated with a particular surgeon alongside a quantity of fluid leaks associated with a different surgeon. Comparisons can be made for any surgical-event related category. Other medical professionals may be associated with a particular location, hospital, department, specialty, or residency class. In some embodiments, an interface for permitting comparison of video frames captured from the specific medical professional and the at least one other medical professional may be provided. The interface may be a graphical user interface such as on a display of a computing device, e.g., user interface 700, or may include any other mechanism for providing the user with information.

Aspects of the present disclosure may include receiving a selection of a particular surgical event-related category. In some examples, an indication may be received from the user of a particular surgical event-related category from a plurality of surgical event-related categories, for example, through a user interface, through an input device (such as a mouse, a keyboard, a touchscreen, a camera, a microphone, etc.), through a gesture using a gesture recognition algorithm, through speech commands using speech recognition algorithms, and so forth. The selection may be received from a medical professional using an interface, such as described above.

In some aspects of the present disclosure graphic characterizing aspects within a category may be displayed, enabling selection of a particular aspect within a category. For example, a surgical event-related category may be broken down into various aspects governing portions of a procedure step, a safety milestone, a point of decision, an intraoperative event, an operative milestone, or an intraoperative decision. In other examples, aspects within a category may be displayed based on statistical information as described above. Selection of the aspects within a category may be made through any user input device or user interface as described above.

In some aspects of the disclosed embodiments, upon receipt of the selection of a particular surgical event-related category, a presentation of at least part of the frames assigned to the particular surgical event-related category may be displayed. The presentation may enable the user to view surgical footage of at least one surgical event sharing the selected surgical event category, while omitting playback of video footage lacking the selected surgical event category. Surgical footage may refer to any video or video footage, as described in greater detail herein, capturing a surgical procedure. In some embodiments, causing the matching subset of stored video footage to be displayed may include executing instructions for playing the video. For example, a processing device performing the methods described herein may access the matching subset of video footage and may be configured to present the stored video footage to the user on a screen or other display. In some embodiments, causing the matching subset of stored video footage to be displayed to the user may include transmitting the stored video footage for display. For example, the matching subset of video footage may be transmitted through a network to a computing device associated with the user, such as a desktop computer, a laptop computer, a mobile phone, a tablet, smart glasses, head-up display, a training device, or any other device capable of displaying video footage. Frames may be presented based on selection of a surgical event related category, or they may be identified and selected based upon selection of a particular aspect within a category as described above.

In some embodiments, the presentation of at least part of the frames assigned to the particular surgical event-related category includes a grouping of video frames from different surgical videos. The video frames may be complied into a common file for presentation or may be extracted at the time of playback from differing files. The video footage may be stored in the same location or may be selected from a plurality of storage locations. Although not necessarily so, videos within a set may be related in some way. For example, video footage within a set may include videos, recorded by the same capture device, recorded at the same facility, recorded at the same time or within the same timeframe, depicting surgical procedures performed on the same patient or group of patients, depicting the same or similar surgical procedures, depicting surgical procedures sharing a common characteristic (such as similar complexity level, including similar events, including usages of similar techniques, including usages of similar medical instruments, etc.), or sharing any other properties or characteristics. For example, frames from many different patients may be associated with a surgical-event related category. The grouping of video frames may include sequential sets of video frames of surgical procedures on differing patients, and presenting may include a video playback of sequential excerpts from the surgical procedures on differing patients. Video playback may be displayed on desktop computer, a laptop computer, a mobile phone, a tablet, smart glasses, head-up display, a training device, or any other device capable of displaying video footage. The graphical user interface may display the sequential excerpts in a window alongside statistical information and/or surgical-event categories. For example, the interface may present video playback of frames interrelated to the surgical-event category "misidentification of cystic structures" alongside statistical data showing a quantity of such events and alongside a label indicating the particular medical professional.

In some aspects of the disclosed embodiments, patient-related personal information may be received, and during a time when the grouping of video frames is presented, patient-related personal information may be displayed. Patient-related personal information may include information about the patient, such as age, gender, ethnicity, socio-economic status, marital status, geographic location, preexisting medical conditions, prior medical treatments, historic test results, information based on an analysis of electronic medical record of the patient, and so forth. In some cases, two or more fields of patient-related information may be displayed when the grouping of video frames is presented. Thus, for example, during playback of frames of video associated with a particular patient, that patient's personal information may be presented in association with the video frames currently being played back. As frames are played back from various patients, the personal information on the display may change to reflect the change in patients.

In some embodiments, video playback of a particular subgroup of frames associated with the selection corresponds to at least one associated surgical event. The associated surgical event may include a selected surgical event. For example, a surgeon may input a selection of a specific intraoperative event and receive a playback of that specific intraoperative event from a plurality of patients or a plurality of surgical procedures. In one example, the at least one associated surgical event may be selected automatically, for example based on the selection of the particular surgical event-related category, based on past behavior of a user, based on analysis of the one or more of the frames, based on a convolution of at least a portion of the frames, and so forth. In some embodiments, playback of a subgroup of frames of an associated surgical event may appear to the surgeon or another user as a continuous video. In other embodiments playback may stop or pause between the discrete sets of video footage. In such instances, the surgeon or other user may manually start the next set of video footage in the sequence.

In other embodiments, the playback of a particular subgroup of frames includes frames from a plurality of differing surgical procedures. For example, common intraoperative events from differing surgical procedures may be displayed. For example, if a similar dissection occurs in multiple videos even when the surgical procedure differs, the frames associated with that dissection in each video may be displayed. Surgical procedures may be associated with patients with similar characteristics, or they may be associated with patients with differing characteristics.

Aspects of this disclosure may include receiving a plurality of additional surgical videos from a plurality of surgical procedures performed by other medical professionals. For example, rather than display only videos of surgical procedures performed by a particular medical professional or group of medical professionals, the system my retrieve for display, frames from other professionals. Retrieval criteria may include selection of other medical professionals who share with a particular medical professional one or more characteristics, such as an age, a sex, an experience level, a skill level, or any other measurable characteristic. In some cases, the specific medical professional and the other medical professional may share no common characteristics, or a selection may occur to present video demonstrating best practices or improved techniques.

Aspects of the present disclosure may include presenting a statistical comparison of the specific medical professional with the other medical professionals. For example, displaying the surgical event-related categories for selection together with the aggregated statistic may additionally include displaying the statistics of other medical professionals. A statistic as used in this context may include any measure of performance or any characterization of an outcome, a skill level, or any other indicator relating to the medical professional, the patient, and/or the procedure. Display of the statistics may occur through a visual user interface, e.g., user interface 700, audibly, and/or any other mechanism of presentation. The display may be done via alphanumeric characters or through graphical displays, such as bar graphs, line graphs, or any other plotted vectors.

Figure 7:
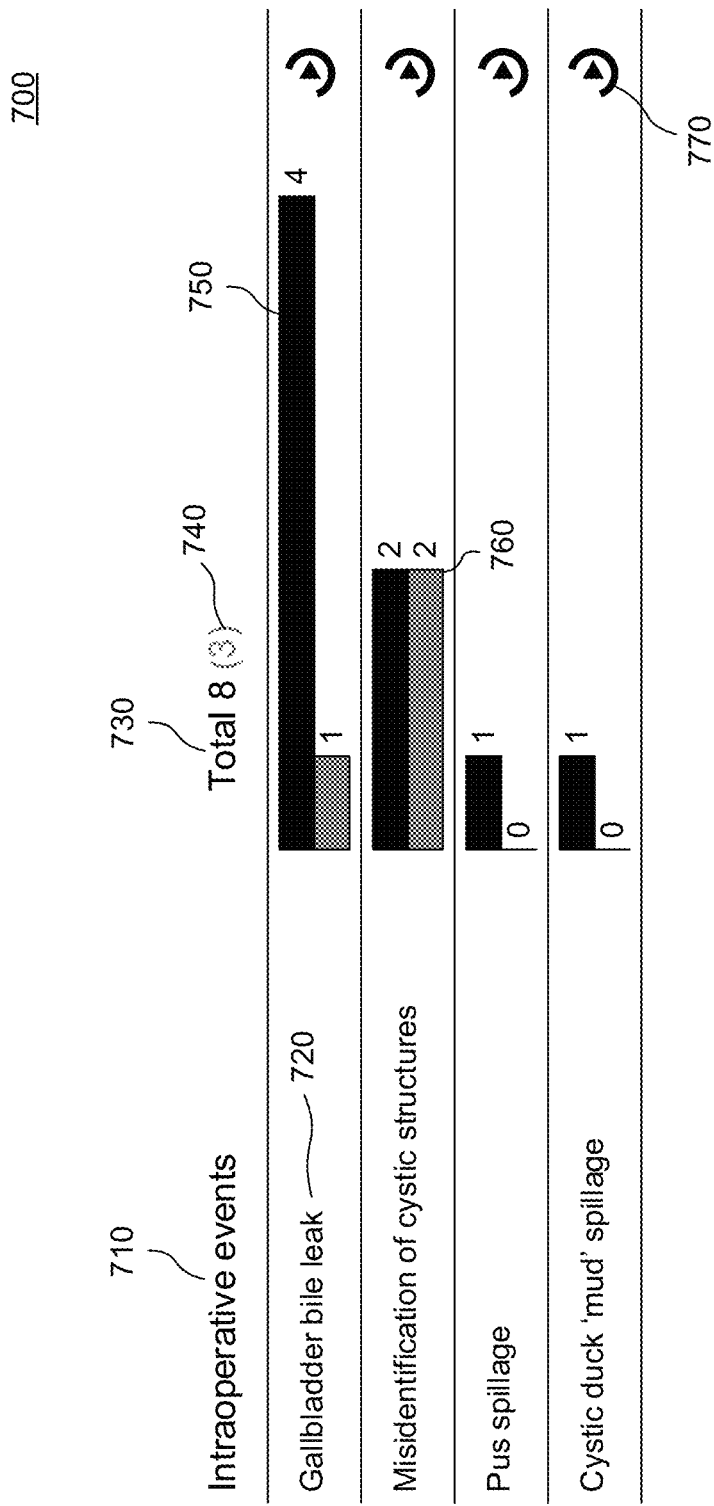
FIG. 7 is a schematic illustration of an example user interface for displaying and aggregating statistical data associated with surgical videos.

FIG. 7 is an illustration of exemplary user interface 700 for displaying surgical event-related categories for selection together with the aggregated statistics for each surgical event-related category. User interface 700 may include heading 710 denoting a surgical event-related category indicator. User interface 700 may further include surgical event-related category 720, which describes the surgical event-related category that is associated with corresponding statistics. User interface 700 may include an aggregation of statistics representing a composite statistic associated with the surgical event-related category. For example, user interface 700 may include descriptor 730, an aggregated statistic displayed for the entire surgical event-related category indicator, or it may include descriptor 750, a statistic for a single surgical event-related category. User interface 700 may include a statistical comparison of the specific medical professional with the other medical professionals. The user interface 700 may include descriptor 740, a value reflecting a statistical comparison of the specific medical professional and the other medical professional across the surgical event-related category indicator, or it may include descriptor 760, a value reflecting a statistical comparison of the specific medical professional and the other medical professional across the surgical event-related category. A user may receive a presentation of frames assigned to a particular surgical event-related category by inputting a selection of a particular surgical event-related category by clicking, tapping, or otherwise selecting icon 770.

In some embodiments, operations further include presenting in a common view patient-related data for a particular patient, and a video player configured to playback frames of surgical video associated with the particular patient. For example, a graphical user interface may display the frames of surgical video in a window alongside text or images reflecting patient-related data associated with the frames. In further embodiments, as frames associated with differing patients are presented sequentially, the patient-related data in the common view may change. Patient-related data includes any data associated with a patient, such as name, age, sex, weight, height, existing medical conditions such as obesity, diabetes, high blood pressure and the like, prior medical treatments, historic test results, information based on an analysis of electronic medical record of the patient, or any other data characterizing the patient. For example, a surgeon may input patient-related data, such as age and a pre-existing medical information, and receive playback of frames associated with that input selection. As playback progresses among a plurality of patients, the displayed patient data may be updated to reflect the data associated with frames associated with the currently displayed patient.

Figure 24A:
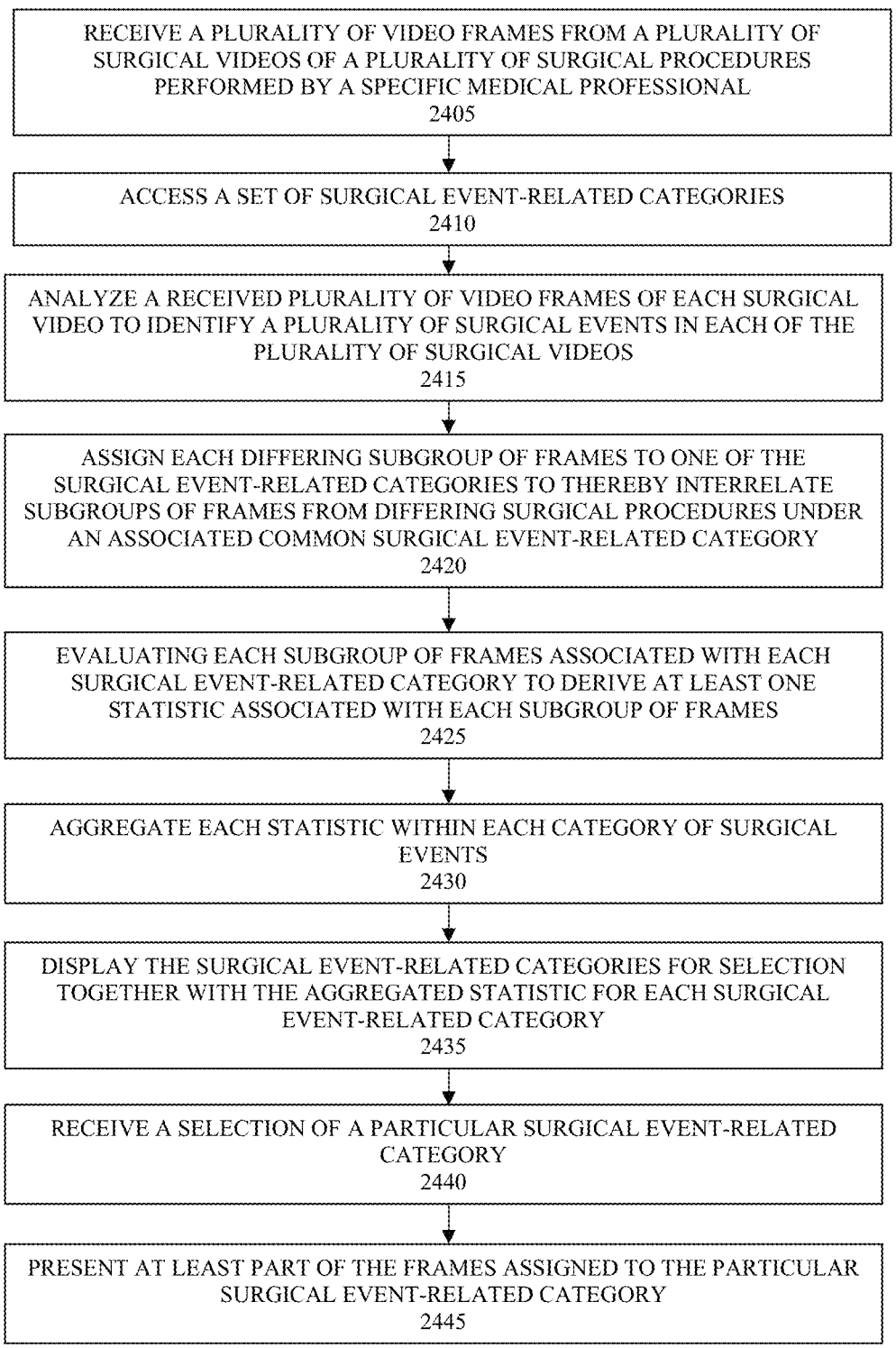
FIG. 24A is a flowchart illustrating an exemplary process for statistical analysis across surgical videos consistent with disclosed embodiments.

FIG. 24A is a flowchart illustrating an example process 2400 for statistical analysis of surgical videos, consistent with the disclosed embodiments. Process 2400 may be performed by a one or more processors. In some embodiments, a non-transitory computer readable medium may contain instructions that when executed by a processor cause the processor to perform process 2400 or portions thereof. Process 2400 is not necessarily limited to the steps shown in FIG. 24A and any steps or processes of the various embodiments described throughout the present disclosure may also be included in process 2400. At step 2405, process 2400 may include receiving a plurality of video frames from a plurality of surgical videos of a plurality of surgical procedures performed by a specific medical professional. The plurality of sets of surgical video footage may include intraoperative surgical events, surgical outcomes, patient characteristics, surgeon characteristics, and intraoperative surgical event characteristics.

At step 2410, process 2400 may include accessing a set of surgical event-related categories. Surgical event-related categories may be denoted by surgical event-related category indicators such as a procedure step, a safety milestone, a point of decision, an intraoperative event, an operative milestone, or an intraoperative decision. Surgical event-related categories may be stored in a database or data structure.

At step 2415, process 2400 may include analyzing the received video frames to identify a plurality of surgical events in each of the surgical videos. The surgical events may correspond to the category indicators as described above.

At step 2420, process 2400 may include interrelating a subgroup of frames from differing surgical procedures under an associated common surgical event-related category by assigning each differing subgroup of frames to one of the surgical event-related categories. Assignment may occur through manual user input, or it may occur through the use of a trained machine learning algorithm as described above.

At step 2425, process 2400 may include evaluating each subgroup of frames associated with each surgical event-related category to derive at least one statistic associated with each subgroup of frames. Statistical information may include a plurality of items as described above, and each item may correspond to one or more intraoperative events. Statistics may then be aggregated within each category of surgical events in step 2430 of process 2400.

At step 2435, process 2400 may include displaying the surgical event-related categories for selection together with the aggregated statistic for each surgical event-related category. As described above, displaying the categories together with the aggregated statistic may include displaying the presentation on a screen or other display device, storing the presentation in a location accessible to another computing device, transmitting the presentation, or any other process or method that may cause the enable the presentation and/or compilation to be viewed. Process 2400 may further include step 2440 to receive a selection of a particular surgical event-related category through a user interface as described above.

At step 2445, process 2400 may include enabling a medical professional to view a presentation including a compilation of frames assigned to the particular surgical event-related categories. The presentation may be displayed on a screen or other display device.

Figure 24B:
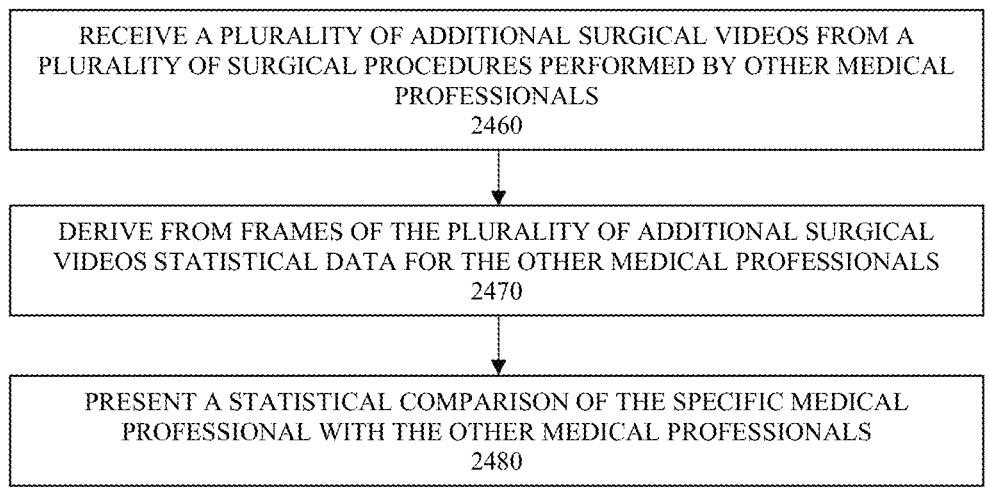
FIG. 24B is a flowchart illustrating an exemplary process for statistical analysis of other medical professionals across surgical videos consistent with disclosed embodiments.

In some embodiments process 2400 may be supplemented by a processing device performing the operations of process 2450, as illustrated in FIG. 24B. Process 2400 and process 2450 may be performed simultaneously or they may be performed at different times.

At step 2460, process 2450 may include receiving a plurality of additional surgical videos from a plurality of surgical procedures performed by other medical professionals. Different portions of the plurality of additional surgical videos may correspond to at least one of intraoperative surgical events, surgical outcomes, patient characteristics, surgeon characteristics, and intraoperative surgical event characteristics. As described above, other medical professionals may be associated with a particular location, hospital, department, specialty, or residency class.

At step 2470, process 2450 may include deriving from frames of the plurality of additional surgical videos statistical data for the other medical professionals. Statistical information may include a plurality of items as described above, and each item may correspond to one or more intraoperative events.

At step 2480, process 2450 may include presenting a statistical comparison of the specific medical professional with the other medical professionals. The presentation may be displayed on a screen or other display device.

Aspects of the present disclosure relate to systems and methods for detecting instrumental deviations from surgical planes in a surgical procedure. Disclosed systems and methods may involve using artificial intelligence to automatically detect deviations from surgical planes by analyzing frames of surgical procedures, comparing the frames to stored data characterizing a surgical plane corresponding to the location of the interaction and outputting an out-of-surgical plane signal indicating a deviation from the surgical plane by the surgical instrument.

In surgical procedures, it is important for surgeons to remain within a surgical plane, so as not to cause collateral damage to the patient. A surgeon who operates a surgical instrument within a surgical plane may minimize patient bleeding, minimize patient tissue trauma, and exert less force on a surgical instrument than a surgeon who operates a surgical instrument outside of a surgical plane. Identification that a surgical instrument has deviated from a surgical plane can be a difficult task. Inexperienced surgeons may lack the proficiency to properly identify surgical planes. Even experienced surgeons may struggle to properly identify a deviation from a surgical plane if they are performing an unfamiliar procedure. Although surgical video may be available, systems and methods for automatically detecting deviations from a surgical plane in video and providing real time feedback to medical professionals are lacking.

Therefore, there is a need for unconventional approaches to enable a user to receive an out-of-surgical plane signal indicating a deviation from a surgical plane by a surgical instrument through machine learning enabled video processing techniques to provide solutions for detecting deviations from surgical planes otherwise undetectable by a surgeon.

Aspects of this disclosure may relate to video of a surgical procedure. A surgical procedure may include any set of medical actions associated with or involving manual or operative activity on a patient's body. Surgical procedures may include one or more of surgeries, repairs, ablations, replacements, implantations, implantations, extractions, treatments, restrictions, re-routing, and blockage removal. Such procedures may involve cutting, abrading, suturing, extracting, lancing or any other technique that involves physically changing body tissues and/or organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally invasive surgery for intracerebral hemorrhage evacuation, veterinarian surgery, or any other medical procedure involving some form of incision. While the present disclosure is described in reference to surgical procedures, it is to be understood that it may also apply to other forms of medical procedures involving patient physiology.

A video of a surgical procedure may include any series of still images or frames that were captured during and are associated with the surgical procedure. In some embodiments, at least a portion of the surgical procedure may be depicted in one or more of the still images included in the video. For example, the video of the surgical procedure may be recorded by an image capture device, such as cameras 115, 121, 123, 125, and 127 as shown in FIG. 1, in an operating room, or in a cavity of a patient. Accessing the video of the surgical procedure may include retrieving the video from a storage device (such as one or more memory units, a video server, a cloud storage platform, or any other storage platform), receiving the video from another device through a communication device, capturing the video using image sensors, or any other means for electronically accessing data or files.

Figure 4:
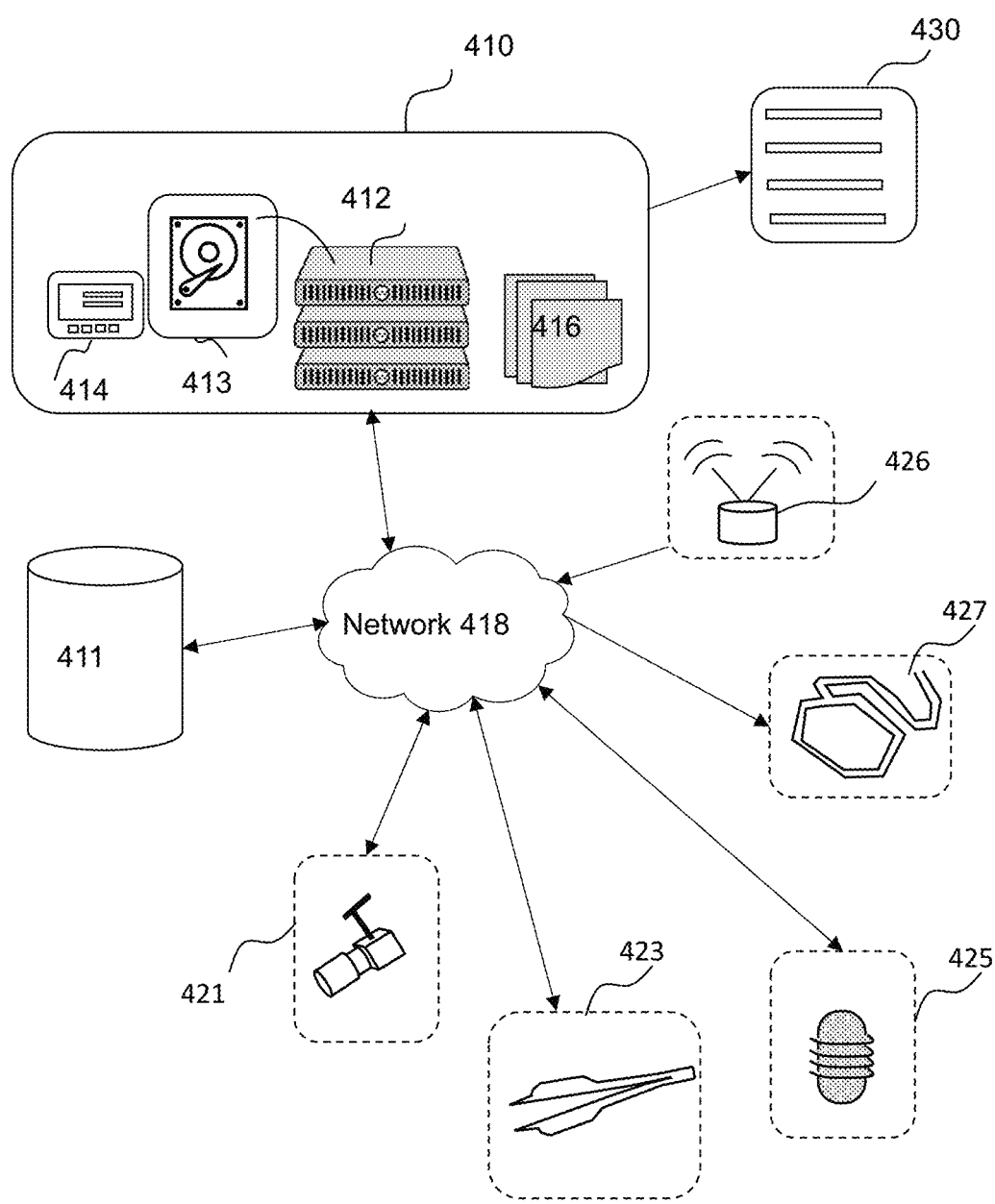
FIG. 4 is a network diagram of an exemplary system for managing various data collected during a surgical procedure, and for controlling various sensors consistent with disclosed embodiments.

Accessing the video of the surgical procedure may be performed via communication to a computer system through a network. For example, FIG. 4 shows an example system 401 that may include a computer system 410, a network 418, and image sensors 421 (e.g., cameras positioned within the operating room), and 423 (e.g., image sensors being part of a surgical instrument) connected via network 418 to computer system 401. System 401 may include a database 411 for storing various types of data related to previously conducted surgeries (i.e., historical surgical data that may include historical image, video or audio data, text data, doctors' notes, data obtained by analyzing historical surgical data, and other data relating to historical surgeries). In various embodiments, historical surgical data may be any surgical data related to previously conducted surgical procedures. Additionally, system 401 may include one or more audio sensors 425, wireless transmitters 426, light emitting devices 427, and a schedule 430.

Computer system 410 may include one or more processors 412 for analyzing the visual data collected by the image sensors, a data storage 413 for storing the visual data and/or other types of information, an input module 414 for entering any suitable input for computer system 410, and software instructions 416 for controlling various aspects of operations of computer system 410.

One or more processors 412 of system 410 may include multiple core processors to handle concurrently multiple operations and/or streams. For example, processors 412 may be parallel processing units to concurrently handle visual data from different image sensors 421 and 423. In some embodiments, processors 412 may include one or more processing devices, such as, but not limited to, microprocessors from the Pentium™ or Xeon™ family manufactured by Intel™, the Turion™ family manufactured by AMD™, or any of various processors from other manufacturers. Processors 412 may include a plurality of co-processors, each configured to run specific operations such as floating-point arithmetic, graphics, signal processing, string processing, or I/O interfacing. In some embodiments, processors may include a field-programmable gate array (FPGA), central processing units (CPUs), graphical processing units (GPUs), and the like.

Database 411 may include one or more computing devices configured with appropriate software to perform operations for providing content to system 410. Database 411 may include, for example, Oracle™ database, Sybase™ database, and/or other relational databases or non-relational databases, such as Hadoop™ sequence files, HBase™, or Cassandra™. In an illustrative embodiment, database 411 may include computing components (e.g., database management system, database server, etc.) configured to receive and process requests for data stored in memory devices of the database and to provide data from the database. As discussed before, database 411 may be configured to collect and/or maintain the data associated with surgical procedures. Database 411 may collect the data from a variety of sources, including, for instance, online resources.

Network 418 may include any type of connections between various computing components. For example, network 418 may facilitate the exchange of information via network connections that may include Internet connections, Local Area Network connections, near field communication (NFC), and/or other suitable connection(s) that enables the sending and receiving of information between the components of system 401. In some embodiments, one or more components of system 401 may communicate directly through one or more dedicated communication links.

Various example embodiments of the system 401 may include computer-implemented methods, tangible non-transitory computer-readable mediums, and systems. The computer-implemented methods may be executed, for example, by at least one processor that receives instructions from a non-transitory computer-readable storage medium such as medium 413, as shown in FIG. 4. Similarly, systems and devices consistent with the present disclosure may include at least one processor and memory, and the memory may be a non-transitory computer-readable storage medium. As used herein, a non-transitory computer-readable storage medium refers to any type of physical memory on which information or data readable by at least one processor can be stored. Examples may include random access memory (RAM), read-only memory (ROM), volatile memory, non-volatile memory, hard drives, CD ROMs, DVDs, flash drives, disks, and any other known physical storage medium whether some or all portions thereof are physically located in or near the operating room, in another room of the same facility, at a remote captive site, or in a cloud-based server farm. Singular terms, such as "memory" and "computer-readable storage medium," may additionally refer to multiple structures, such a plurality of memories or computer-readable storage mediums. As referred to herein, a "memory" may include any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Input module 414 may be any suitable input interface for providing input to one or more processors 412. In an example embodiment, input interface may be a keyboard for inputting alphanumerical characters, a mouse, a joystick, a touch screen, an on-screen keyboard, a smartphone, an audio capturing device (e.g., a microphone), a gesture capturing device (e.g., camera), and other device for inputting data. While a user inputs the information, the information may be displayed on a monitor to ensure the correctness of the input. In various embodiments, the input may be analyzed verified or changed before being submitted to system 410.

Software instructions 416 may be configured to control various aspects of operation of system 410, which may include receiving and analyzing the visual data from the image sensors, controlling various aspects of the image sensors (e.g., moving image sensors, rotating image sensors, operating zoom lens of image sensors for zooming towards an example ROI, and/or other movements), controlling various aspects of other devices in the operating room (e.g., controlling operation of audio sensors, chemical sensors, light emitting devices, and/or other devices).

As previously described, image sensors 421 may be any suitable sensors capable of capturing image or video data. For example, such sensors may be cameras 115-125.

Audio sensors 425 may be any suitable sensors for capturing audio data. Audio sensors 425 may be configured to capture audio by converting sounds to digital information. Some examples of audio sensors 425 may include microphones, unidirectional microphones, bidirectional microphones, cardioid microphones, omnidirectional microphones, onboard microphones, wired microphones, wireless microphones, any combination of the above, and any other sound-capturing device.

Wireless transmitter 426 may include and suitable wireless device capable of transmitting a location identifier. The wireless transmitter may communicate with other elements in the operating room through wireless signals, such as radio communication including Bluetooth or Wireless USB, Wi-Fi, LPWAN, or other suitable wireless communication methods.

Light emitting devices 427 may be configured to emit light, for example, in order to enable better image capturing by image sensors 421. In some embodiments, the emission of light may be coordinated with the capturing operation of image sensors 421. Additionally or alternatively, the emission of light may be continuous. In some cases, the emission of light may be performed at selected times. The emitted light may be visible light, infrared light, ultraviolet light, deep ultraviolet light, x-rays, gamma rays, and/or in any other portion of the light spectrum.

Aspects of this disclosure may relate to detecting surgical instruments. A surgical instrument may refer to a medical device, a medical instrument, an electrical or mechanical tool, a surgical tool, a diagnostic tool, and/or any other instrumentality that may be used during a surgery such as scalpels, graspers (e.g., forceps), clamps and occluders, needles, retractors, cutters, dilators, suction tips, and tubes, sealing devices, irrigation and injection needles, scopes and probes, and the like. By way of one example, a surgical instrument may include instrument 301 shown in FIG. 3.

Aspects of this disclosure may relate to detecting surgical instrumental deviations from surgical planes. In one example, a surgical plane may include an interface area between two tissue surfaces being separated. A surgeon may create separation between two structures such as tissues or contiguous organs by operating in a surgical plane. The surgical plane may consist of spider-web like areolar tissue when insufflated with very few other structures such as blood vessels. Operating in a surgical plane may enable structures to be separated with a very gentle force, both separated structures may be completely or almost completely preserved in that their wall or envelope is not interrupted, and there may be very little bleeding. In another example, a surgical plane may include a desired plane for a performance of one or more surgical operations, for example to improve outcome, to simplify the surgical procedure, to minimize bleeding, to minimize organ and tissue trauma, and so forth. A surgical instrument deviation from a surgical plane would be an unexpected departure of the surgical instrument from operating in the surgical plane. An unexpected departure may include a piercing or incision of a tissue or organ, a rupture of a blood vessel, or a resistance to separation of the tissues or organs. More broadly, any divergence from an expected action within a surgical plane may be considered a deviation.

Disclosed embodiments may involve receiving a plurality of video frames from a surgical video feed. A surgical video feed may refer to any video, group of video frames, or video footage including representations of a surgical procedure. For example, the surgical video feed may include one or more video frames captured during a surgical operation. A plurality of video frames may refer to a grouping of frames from one or more surgical videos or surgical video clips. The video frames may be stored in a common location or may be stored in a plurality of differing storage locations. Although not necessarily so, video frames within a received group may be related in some way. For example, video frames within a set may include frames, recorded by the same capture device, recorded at the same facility, recorded at the same time or within the same timeframe, depicting surgical procedures performed on the same patient or group of patients, depicting the same or similar surgical procedures, or sharing any other properties or characteristics. Alternatively, one or more video frames may be captured at different times from surgical procedures performed on differing patients. In some embodiments, the plurality of video frames of the video feed is obtained from pre-stored video footage of the surgical procedure. In other embodiments, the video feed is a real-time broadcast of the surgical procedure such as that captured by an image capture device, such as a camera, in an operating room or in a cavity of a patient.

Some embodiments include analyzing at least some of the plurality of video frames to identify a surgical instrument therein. Analyzing the received video frames to identify a surgical instrument therein may involve any form of electronic analysis using a computing device, for example as described above. In one example, one or more convolutions of at least a portion of the plurality of video frames may be calculated, and the calculated one or more convolutions may be used to identify a surgical instrument within the video frames.

Figure 8A:
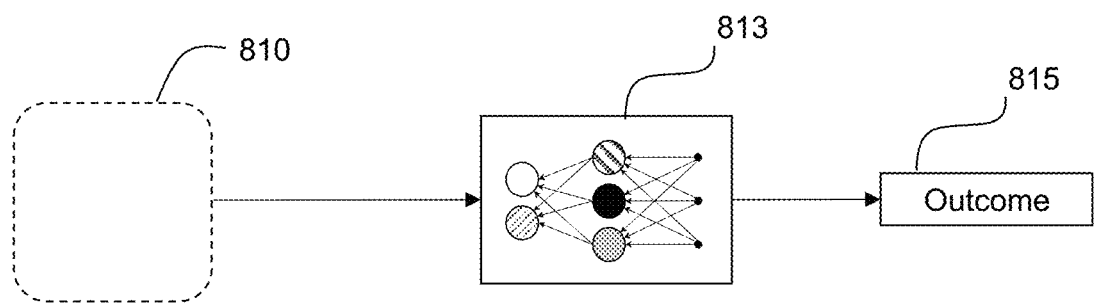
FIG. 8A is a graphical illustration of an exemplary machine-learning model, consistent with disclosed embodiments.
Figure 8B:
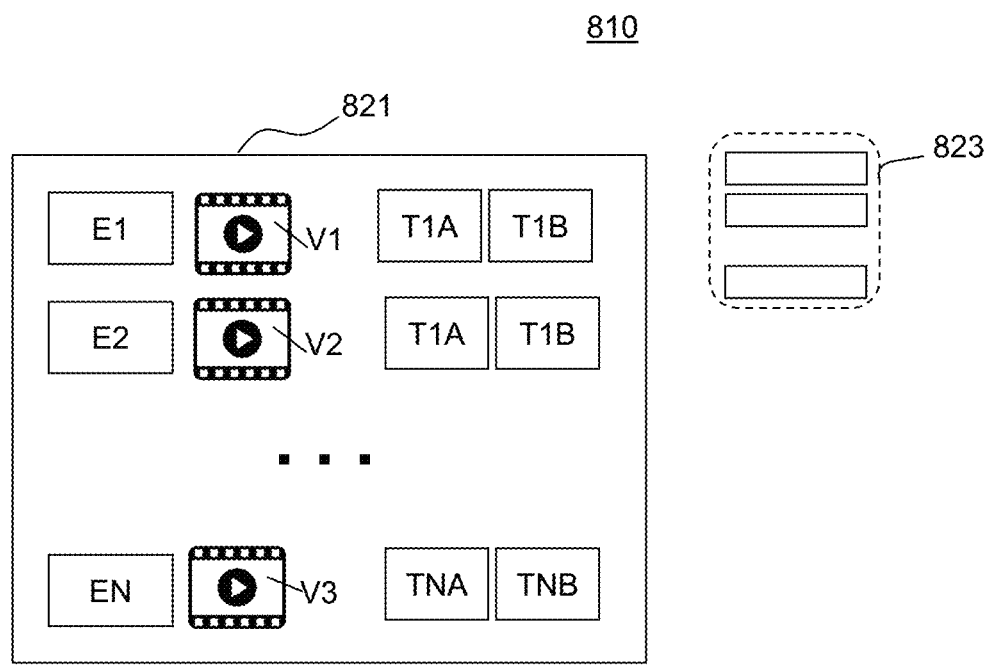
FIG. 8B shows an exemplary input for a machine-learning model, consistent with disclosed embodiments.

FIG. 8A shows an example event-based machine learning model 813 that takes input 810 and outputs a predicted outcome for a surgical procedure 815. Input 810 may include input parameters 823, as shown in FIG. 8B, such as patient characteristics and information from a medical record as previously discussed. Further, input 810 may include information from the postoperative surgical report that may include event data 821, as shown in FIG. 8B. In an example embodiment, event data 821 may include a list of events (e.g., events E1-EN), and surgical footage segments V1-VN corresponding to events E1-EN. Further, data 821 in FIG. 8B may include event starting times T1A-TNA and finishing times T1B-TNB. Surgical footage (e.g., V1) may be a set of frames of a surgical procedure corresponding to an event (e.g., E1). In an example embodiment, for an example surgical procedure, event E1 may be a short event (e.g., incision) for which T1A and T1B may be about the same time; event E2 may be an extended time (e.g., suturing) for which T2A is the time at which the suturing started and T2B is the time at which the suturing ended; and event EN may be a process of administering medications to reverse anesthesia having corresponding starting time TNA and finishing time TNB.

In various embodiments, the event-based machine learning method may be trained using training examples, for example as described above. For example, a training example may be based on historical data. In another example, a training example may include information related to a surgical procedure (for example as described above), together with a label indicating an outcome.

Some embodiments may include evaluating the plurality of video frames with the identified surgical instrument therein to ascertain an interface area corresponding to a location of an interaction between the identified surgical instrument and tissue. An interface area may be a two-dimensional plane or a three-dimensional surface captured in the video frames by the video feed, and in some examples may move from one frame to another. Evaluating may involve the computer analysis/artificial intelligence described herein. For example, visual action recognition algorithms may be used to analyze the video and detect the interactions between the surgical instrument and the anatomical structure or tissue.

Using computer analysis and artificial intelligence to evaluate the plurality of video frames increases efficiency and accuracy when evaluating surgical interactions. For instance, evaluating can be performed at speeds that are able to identify risks associated with even minute movements in real time unattainable by humans. It can enable near continuous evaluation to improve accuracy when used in real time. Furthermore, video frames of the interface area may be captured by recording devices positioned in locations otherwise inaccessible to the human eye, such as cameras located on surgical equipment inserted into a patient, or from differing vantage points. This can enable evaluation of interface areas and locations of interaction otherwise invisible to a skilled surgeon. By using the disclosed computerized methods to ascertain an interface area corresponding to a location of an interaction, the embodiments provide advantages over prior systems that merely present video without analysis and rely on human judgement for determining interaction locations. For example, relying on surgical planes may enable faster detection of evolving surgical mistakes, may improve accuracy of image based surgical error detectors, may enable better categorization of detected surgical errors, may offer explainable justification for automatic detections of surgical errors (and may therefore facilitate explainable artificial intelligent in that field), may enable localization of automatic detected surgical errors to particular regions (for example, particular regions in the patient body, particular regions in the video frames, etc.), and so forth. Further, prior automated methods for determining errors in surgery captured by video may not rely on the identification of an interaction location and may be insensitive or unresponsive to real time interactions in surgery.

An interface area may correspond to a location of an interaction between the identified surgical instrument and tissue. An interaction may include any action by the surgical instrument that may influence the anatomical structure, or vice versa. For example, the interaction may include a contact between the medical instrument and the anatomical structure, an action by the surgical instrument on the anatomical structure (such as cutting, clamping, applying pressure, scraping, etc.), a reaction by the anatomical structure (such as a reflex action), a physiological response by the anatomical structure, the surgical tool emitting light towards the anatomical structure (e.g., surgical tool may be a laser that emits light towards the anatomical structure) a sound emitted towards anatomical structure, an electromagnetic field created in a proximity of the anatomical structure, a current induced into an anatomical structure, or any other suitable forms of interaction from which biological material-instrument feedback may be obtained. For example, a machine learning model may be trained using training examples to detect interactions between surgical instruments and anatomical structures from videos, and the trained machine learning model may be used to analyze the video footage and detect the interaction between the medical instrument and the anatomical structure.

In some cases, identifying interaction may include identifying the proximity of the surgical tool to an anatomical structure. For example, by analyzing the surgical video footage of an example surgical procedure, the image analysis model may be configured to determine a distance between the surgical tool and a point (or a set of points) of an anatomical structure.

Some aspects of the present disclosure may involve accessing stored data. Stored data may refer to data of any format that was recorded and/or stored previously. In some embodiments, the stored data may be one or more video files including historical surgical footage. For example, the stored data may include a series of frames captured during the prior surgical procedures. This stored data is not limited to video files, however. For example, the stored data may include information stored as text representing at least one aspect of the stored surgical footage. For example, the stored data may include a database of information summarizing or otherwise referring to historical surgical footage. In another example, the stored data may include information stored as numerical values representing at least one aspect of the historical surgical footage. In an additional example, the stored data may include statistical information and/or statistical model based on an analysis of the historical surgical footage. In yet another example, the stored data may include a machine learning model trained using training examples, and the training examples may be based on the historical surgical footage. Accessing the stored data may include receiving the stored data through an electronic transmission, retrieving the historical data from storage (e.g., a memory device), or any other process for accessing data. In some embodiments, the stored data may be accessed from the same resource as the particular surgical footage discussed above. In other embodiments, the stored data may be accessed from a separate resource. Additionally or alternatively, accessing the stored data may include generating the stored data, for example by analyzing previously recorded surgical procedures or by analyzing data based on the stored surgical footage of prior surgical procedures.

In an example embodiment, the data structure may be a relational database having one or more database tables. For instance, FIG. 5 illustrates an example of data structure 501 that may include data tables 511 and 513. In an example embodiment, data structure 501 may be part of relational databases, may be stored in memory, and so forth. Tables 511 and 513 may include multiple records (e.g., records 1 and 2, as shown in FIG. 5) and may have various fields, such as fields "Record Number", "Procedure", "Age", "Gender", "Medical Considerations", "Time", and "Other Data". For instance, field "Record Number" may include a label for a record that may be an integer, field "Procedure" may include a name of a surgical procedure, field "Age" may include an age of a patient, field "Gender" may include a gender of the patient, field "Medical Considerations" may include information about medical history for the patient that may be relevant to the surgical procedure having the name as indicated in field "Procedure", field "Time" may include time that it took for the surgical procedure, and field "Other Data" may include links to any other suitable data related to the surgical procedure. For example, as shown in FIG. 5, 511 may include links to data 512A that may correspond to image data, data 512B that may correspond to video data, data 512C that may correspond to text data (e.g., notes recorded during or after the surgical procedure, patient records, postoperative report, etc.), and data 512D that may correspond to an audio data. In various embodiments, image, video, or audio data may be captured during the surgical procedure. In some cases, video data may also include audio data. Image, video, text or audio data 512A-512D are only some of the data that may be collected during the surgical procedure. Other data may include vital sign data of the patient, such as heart rate data, blood pressure data, blood test data, oxygen level, or any other patient-related data recorded during the surgical procedure. Some additional examples of data may include room temperature, type of surgical instruments used, or any other data related to the surgical procedure and recorded before, during or after the surgical procedure.

As shown in FIG. 5, tables 511 and 513 may include a record for a surgical procedure. For example, tables may have information about surgical procedures, such as the type of procedure, patient information or characteristics, length of the procedure, a location of the procedure, a surgeon's identify or other information, an associated anesthesiologist's identity, the time of day of the surgical procedure, whether the surgical procedure was a first, a second, a third, etc. procedure conducted by a surgeon (e.g., in the surgeon lifetime, within a particular day, on a particular patient, etc.), an associated anesthesiologist nurse assistant, whether there were any complications during the surgical procedure, and any other information relevant to the procedure. For example, record 1 of table 511 indicates that a bypass surgical procedure was performed on a male of 65 years old, having a renal disease and that the bypass surgery was completed in 4 hours. A record 2 of table 511 indicates that a bypass surgical procedure was performed on a female of 78 years old, having no background medical condition that may complicate the surgical procedure, and that the bypass surgery was completed in 3 hours. Table 513 indicates that the bypass surgery for the male of 65 years old was conducted by Dr. Mac, and that the bypass surgery for the female of 78 years old was conducted by Dr. Doe. The patient characteristics such as age, gender, and medical considerations listed in table 511 are only some of the example patient characteristics, and any other suitable characteristics may be used to differentiate one surgical procedure from another. For example, patient characteristics may further include patient allergies, patient tolerance to anesthetics, various particulars of a patient (e.g., how many arteries need to be treated during the bypass surgery), a weight of the patient, a size of the patient, particulars of anatomy of the patient, or any other patient related characteristics which may have an impact on a duration (and success) of the surgical procedure.

Data structure 501 may have any other number of suitable tables that may characterize any suitable aspects of the surgical procedure. For example, 501 may include a table indicating an associated anesthesiologist's identity, the time of day of the surgical procedure, whether the surgical procedure was a first, a second, a third, etc. procedure conducted by a surgeon (e.g., in the surgeon lifetime, within a particular day, etc.), an associated anesthesiologist nurse assistant, whether there were any complications during the surgical procedure, and any other information relevant to the procedure.

Accessing a data structure may include reading and/or writing information to the data structure. For example, reading and/or writing from/to the data structure may include reading and/or writing any suitable historical surgical data such as historic visual data, historic audio data, historic text data (e.g., notes during an example historic surgical procedure), and/or other historical data formats. In an example embodiment, accessing the data structure may include reading and/or writing data from/to database 111 or any other suitable electronic storage repository. In some cases, writing data may include printing data (e.g., printing reports containing historical data on paper).

FIG. 6 illustrates an example data structure 600 consistent with the disclosed embodiments. As shown in FIG. 6, data structure 600 may comprise a table including video footage 610 and video footage 620 pertaining to different surgical procedures. For example, video footage 610 may include footage of a laparoscopic cholecystectomy, while video footage 620 may include footage of a cataract surgery. Video footage 620 may be associated with footage location 621, which may correspond to a particular surgical phase of the cataract surgery. Phase tag 622 may identify the phase (in this instance a corneal incision) associated with footage location 621, as discussed above. Video footage 620 may also be associated with event tag 624, which may identify an intraoperative surgical event (in this instance an incision) within the surgical phase occurring at event location 623. Video footage 620 may further be associated with event characteristic 625, which may describe one or more characteristics of the intraoperative surgical event, such as surgeon skill level, as described in detail above. Each video footage identified in the data structure may be associated with more than one footage location, phase tag, event location, event tag and/or event characteristic. For example, video footage 610 may be associated with phase tags corresponding to more than one surgical phase (e.g., "Calot's triangle dissection" and "cutting of cystic duct"). Further, each surgical phase of a particular video footage may be associated with more than one event, and accordingly may be associated with more than one event location, event tag, and/or event characteristic. It is understood, however, that in some embodiments, a particular video footage may be associated with a single surgical phase and/or event. It is also understood that in some embodiments, an event may be associated with any number of event characteristics, including no event characteristics, a single event characteristic, two event characteristics, more than two event characteristics, and so forth. Some non-limiting examples of such event characteristics may include skill level associated with the event (such as minimal skill level required, skill level demonstrated, skill level of a medical care giver involved in the event, etc.), time associated with the event (such as start time, end time, etc.), type of the event, information related to medical instruments involved in the event, information related to anatomical structures involved in the event, information related to medical outcome associated with the event, one or more amounts (such as an amount of leak, amount of medication, amount of fluids, etc.), one or more dimensions (such as dimensions of anatomical structures, dimensions of incision, etc.), and so forth. Further, it is to be understood that data structure 600 is provided by way of example and various other data structures may be used.

In some embodiments, the stored data may characterize a surgical plane corresponding to the location of the interaction. Surgical planes corresponding to an interaction may be characterized by identified medical instruments, anatomical structures, interactions between medical instruments and anatomical structures, a measurement of force applied to a surgical instrument, a location within an anatomical structure, an interaction between adjacent tissues, a location between two organs, a curved area of an anatomical structure, or any other data characterizing an interface between anatomical structures or a predefined operating plane. Stored data characterizing a surgical plane corresponding to an interaction may be stored in a database or data structure. Accessing stored data characterizing a surgical plane improves surgery results for patients by enabling surgeons to detect surgical planes they might not otherwise be able to detect. For instance, a surgeon may not have experience in detecting surgical planes used in a certain procedure, or the surgeon may not have experience in detecting surgical planes commonly found in patients with certain characteristics. Accessing stored data characterizing a surgical plane and presenting this surgical plane data to the surgeon may enable the surgeon to proceed with surgery within a surgical plane and may improve patient outcomes by minimizing bleeding or minimizing organ and tissue trauma. Stored data may be accessed in a data structure consistent with the data structures disclosed herein.

In some embodiments, stored data characterizing a surgical plane is derived from at least one prior surgical procedure. For example, stored data characterizing a surgical plane may be derived from a specific surgical procedure such as an appendectomy, a carotid endarterectomy, a carpal tunnel release, a cataract surgery or any other specific procedure. The data characterizing a surgical plane may be derived from a specific procedure performed on a specific patient, or it may be derived from the specific procedure performed on a plurality of patients. For example, data characterizing a surgical plane may be derived from video frames of an appendectomy performed on a particular patient, or it may be derived from video frames of an appendectomy performed on multiple patients. The stored data may be associated with characteristics of the multiple patients, such as age, height, weight, gender, race, age, medical condition, or any other characteristic associated with the patient. The data characterizing a surgical plane that is derived from the procedure may be associated with these patient characteristics and used to further refine the data characterizing a surgical plane as applied to patients with common characteristics.

In other embodiments, stored data characterizing a surgical plane may be derived from a plurality of prior surgical procedures. The plurality of prior surgical procedures may be related, may be unrelated, may have been performed on a single patient, or may have been performed on multiple differing patients. For example, data characterizing a surgical plane may be derived from two unrelated procedures such as an angioplasty procedure on one patient and a coronary artery bypass graft performed on a differing patient. Each of these surgical procedures may share common interactions between surgical instruments and a surgical plane. Thus, data characterizing a surgical plane may be derived from both surgical procedures and stored in the database. Similarly, data characterizing a surgical plane may be derived from a plurality of prior surgical procedures and is not limited to the example disclosed here.

Aspects of this disclosure may include using the stored data to determine whether the interface area is outside of the surgical plane. For example, video frames may depict the surgical instrument interacting with tissue at an interface area that does not correspond with the location of a surgical plane corresponding to the location of the interaction. In another example, based on a type of interaction and/or stage of the surgical operation, a desired surgical plane may be determined, and the video frames may depict the surgical instrument interacting with tissue at an interface area that does not correspond with the location of the determined surgical plane. The indication that the surgical instrument and its corresponding interface area is outside of the surgical plane may be determined by any of the video analysis techniques disclosed herein. In some examples, a machine learning model may be trained using examples to identify an indication that the surgical instrument and its corresponding interface area is outside of the surgical plane. Non-limiting examples of indications that the surgical instrument and its corresponding interface area is outside of the surgical plane include a piercing of tissue or an organ, an incision of a tissue or organ, a rupture of a blood vessel, bleeding, a release of fluids, a resistance to separation by the tissues or organs indicated by a use of force on the surgical instrument, a color of tissue or organs, or a mix of colors of tissue or organs.

In some embodiments, using the stored data to determine whether the interface area is outside of the surgical plane may include applying artificial intelligence to video frames of prior surgical procedures and extrapolating the surgical plane therefrom. For example, a machine learning model may be trained using examples as disclosed herein. The examples may include one prior surgical procedure, or they may include a plurality of prior surgical procedures. Using examples of prior procedures, machine learning models may be used to identify an interface area that corresponds to a surgical plane extrapolated for the current surgical procedure.

In some aspects of this disclosure, the stored data characterizing the surgical plane may include an indication of expected tissue colors corresponding to the surgical plane. For example, video frames of prior surgical procedures may be analyzed to determine tissue colors that indicate an identified surgical instrument is interacting with tissue at an interface area corresponding to a surgical plane. In other aspects, using stored data to determine whether the interface area is outside of the surgical plane is based on the expected tissue colors corresponding to the surgical plane and on color data of one or more pixels corresponding to the interface area in at least one of the plurality of video frames. For example, pixel data in video frames may indicate a tissue color at the interface area corresponding to a location of an interaction between the surgical instrument and tissue. Stored data may include pixel data representing an expected tissue color corresponding to the surgical plane corresponding to the location of the interaction. The determination may involve evaluating the pixel data in video frames from the surgical procedure and comparing it to pixel data from stored data representing an expected tissue color corresponding to the surgical plane. In some embodiments, the determination of whether the interface area is outside of the surgical plane may be based on at least one convolution of a plurality of pixels corresponding to the interface area in at least one of the plurality of video frames.

Aspects of the present disclosure may include outputting an out-of-surgical plane signal. Outputting an out-of-surgical plane signal may include generating any stimulus that causes a corresponding effect. The signal may transmit a recommendation to a device, cause a display of a notification at an interface, cause a sound to be played, provide haptic feedback, and/or cause any other indication. The indication may be output to a device in an operating room, to a device associated with a surgeon (e.g., a human surgeon and/or a surgical robot), and/or to any other system or device. For example, outputting a signal may include transmitting a notification to a computer, a mobile device, an external device, a surgical robot, and/or any other computing device. In another example, outputting a signal may include causing a notification to be logged in a file. The indication may be a real time warning of a deviation from a surgical plane, a record of such a deviation, or in the case of a surgical robotic system, an instruction for controlling the surgical robot.

In some embodiments outputting an out-of-surgical plane signal may indicate a deviation from the surgical plane by the surgical instrument. For example, stored data may be used to determine whether the interface area between an instrument and a biological structure is outside of the surgical plane, and upon such a determination, an out-of-surgical plane signal may be outputted indicating a deviation from the surgical plane by the surgical instrument. Outputting the out-of-surgical plane signal may include the signal types disclosed herein. A feedback device (light, sound, haptic) in the operating theater may receive the out-of-surgical plane signal and alert the operating surgeon.

In some embodiments the operations may be continuously repeated to continuously monitor deviations from the surgical plane. For example, when a video feed is a real time broadcast of the surgical procedure, the operations may be repeated after a certain quantity of video frames from a video feed is received, or upon elapse of a certain predetermined time interval. This continuous monitoring may enable a surgeon wielding a surgical instrument to experience real-time notification via the out-of-surgical plane signal that a deviation from the surgical plane by the surgical instrument has occurred.

In other embodiments, the operations are continuously repeated to ascertain during the surgical procedure when the surgical instrument is projected to deviate from the surgical plane. For example, an analysis of video frames may identify a surgical instrument interacting with tissue at an interface area corresponding to a boundary of a surgical plane. Stored data characterizing a surgical plane may include boundary data indicating the outer limit of a surgical plane. In some embodiments, evaluating the video frames may include determining that the surgical instrument is adjacent to boundary of a surgical plane, and that due to this proximity, a deviation from the surgical plane is projected to occur. Boundary data may be determined using the video analysis techniques disclosed herein.

In other embodiments, ascertaining when the surgical instrument is projected to deviate from the surgical plane includes tracking movement of the surgical instrument to define a projected path of the surgical instrument. Movement of the surgical instrument may be detected using a motion detection algorithm, for example, based on changes in pixels between frames, optical flow, or other forms of motion detection algorithms. Thus, for example, a path of a surgical instrument may be projected based on a direction and/or speed of movement. If the direction of the path and/or the speed of movement tends to indicate that the surgical instrument is projected to deviate from the surgical plane, an advance warning may be provided. Tracking movement may be combined with evaluating boundary data of the surgical plane or other stored data to determine if the surgical instrument is projected to deviate from the surgical plane.

In some embodiments, operations may include outputting a warning signal before the surgical instrument deviates from the surgical plane. The warning signal may be of a type similar to the out-of-surgical plane signal disclosed herein. For example, the system may determine that the surgical instrument is approaching a boundary of a surgical plane or it may ascertain that the projected path of the surgical instrument indicates the surgical instrument will deviate from the surgical plane. In other embodiments, outputting the warning signal occurs when the surgical instrument is within a predetermined distance from the surgical plane. For example, a predetermined distance may be identified to allow a certain factor of safety or allow for human error by the surgeon such that a warning signal may be outputted prior to the surgical instrument deviating from the surgical plane.

In other embodiments, the warning signal may include instructions on how to avoid deviation from the surgical plane. Instructions may be determined by accessing stored data as described herein. In one example, as a surgical instrument approaches a surgical plane boundary, instructions may be outputted indicating a location of an interface area that is inside of the surgical plane. Instructions may be output through a display, a speaker, a light, a haptic feedback component, an AR display and/or any other input and/or feedback mechanism. Instructions are not limited to the display of an interface area and may include other instructions such as directional haptic feedback, illumination of lights or other signals on the surgical instrument corresponding to a desirable direction of movement, may include audible instructions delivered through a speaker or other sound-producing device, or any other communication medium. The audible or visual instructions may direct the surgeon on how to manipulate a surgical instrument to avoid crossing a surgical plane or on how to return to a surgical plane.

Outputting an out-of-plane signal or a warning signal may improve patient surgical outcomes by alerting a surgeon to deviations or potential deviations of surgical instruments from surgical planes, thereby enabling the surgeon to make corrections to the location of the surgical instrument to operate within the surgical plane. Operating in surgical planes may improve outcomes for patients by minimizing patient bleeding, minimizing patient tissue trauma, decreasing the surgery time, and improving patient recovery.

In some aspects of this disclosure, the operations may further include determining from the plurality of video frames a current step of the surgical procedure. A step may include any action performed by a surgeon (e.g., a human or robotic surgeon) during a surgical procedure, or by a person or robot assisting a surgical procedure. Examples of steps may include remedial actions, diagnostic actions, actions following a surgical procedure, actions deviating from a surgical procedure, and/or any other activity that might occur during a surgical procedure. Such actions may include engaging a medical instrument with a biological structure, administering a medication, cutting, suturing, altering surgical contact, conducting a medical test, cleaning an anatomical structure, removing excess fluid, and/or any other action that may occur during a surgical procedure. A current step may be an action by a surgeon occurring in real time or near real time. Determining a current step of the surgical procedure may include performing computer image analysis on frames of video footage to identify a surgical event, such as a procedure step, a safety milestone, a point of decision, an intraoperative event, an operative milestone, or an intraoperative decision. Determining a current step may also include accessing stored data associated with the surgical procedure to access a list of steps associated with the surgical procedure and based on elements present in the video frames, derive a current step of the surgical procedure through a comparison of video frames associated with a list of steps associated with the current procedure. The comparison may be performed through the computer image analysis disclosed herein.

In some embodiments, determination of the current step of the surgical procedure is used to identify the stored data characterizing a surgical plane. For example, stored data associated with the current step of the surgical procedure may include data characterizing a surgical plane. In one example, the system may determine the current step of the surgical procedure is to separate two interfacing organs. Stored data associated with this step of the surgical procedure may include pixel data based on excepted tissue color corresponding to the surgical plane. Stored data associated with a current step of the surgical procedure is not limited to pixel data and may include boundary data, image data, or other data identifying organs, tissues, or curved areas characterizing the surgical plane. An ordinary artisan would understand that that a plane may refer to any boundary in space, including a two-dimensional plane or a three-dimensional surface (e.g., a boundary defined by a radius), a plane changing in time, and so forth.

Figure 9:
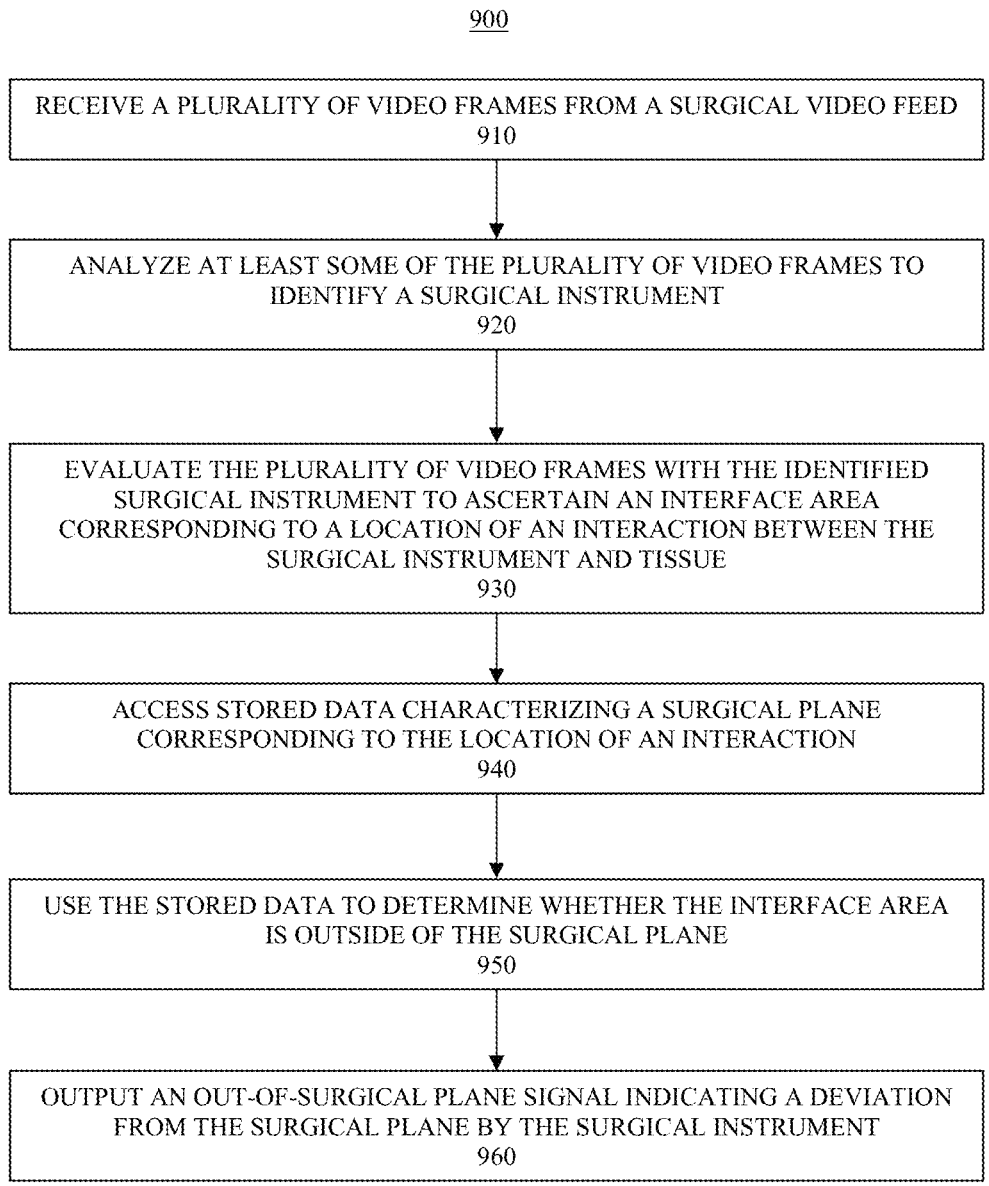
FIG. 9 is a flowchart illustrating an exemplary process for video detection of instrumental deviations from a surgical plane in a surgical procedure, consistent with disclosed embodiments.

FIG. 9 is a flowchart illustrating an example process 900 for detecting instrumental deviations from surgical planes in video of a surgical procedure. Process 900 may be performed by a one or more processors. In some embodiments, a non-transitory computer readable medium may contain instructions that when executed by a processor cause the processor to perform process 900. Process 900 is not necessarily limited to the steps shown in FIG. 9 and any steps or processes of the various embodiments described throughout the present disclosure may also be included in process 900. At step 910, process 900 may include receiving a plurality of video frames from a surgical video feed. The plurality of video frames of the video feed may be obtained from pre-stored video footage of the surgical procedure or it may be a real-time broadcast of the surgical procedure.

At step 920, process 900 may include analyzing at least some of the plurality of video frames to identify a surgical instrument. Analyzing at least some of the plurality of video frames to identify a surgical instrument may involve any form of electronic analysis using a computing device such as object detection algorithms, tracking algorithms, texture-based detection algorithms, or any other suitable algorithms for analyzing video frames as disclosed herein.

At step 930, process 900 may include evaluating the plurality of video frames with the identified surgical instrument to ascertain an interface area corresponding to a location of an interaction between the surgical instrument and tissue. Ascertaining an interface area may be performed by a visual action recognition algorithm.

At step 940, process 900 may include accessing stored data characterizing a surgical plane corresponding to the location of the interaction. Stored data may include frames captured during prior surgical procedures, information stored as text representing an aspect of the stored surgical footage, information stored as numerical values, pixel data, or boundary data, each characterizing a surgical plane corresponding to the location of the interaction.

At step 950, process 900 may include using the stored data to determine whether the interface area is outside of the surgical plane. Using stored data may include comparing image data depicting the location of an interaction between the surgical instrument and tissue and comparing it to image data characterizing a surgical plane corresponding to the location of the interaction.

At step 960, process 900 may include outputting an out-of-surgical plane signal indicating a deviation from the surgical plane by the surgical instrument. Outputting an out-of-surgical plane signal may include transmitting a recommendation to a device, displaying a notification at an interface, playing a sound, providing haptic feedback, and/or any other method. For example, an out-of-surgical notification may be visual, audible, tactile, textual, electronic, and so forth. In one example, visual notification may be provided on a display screen, as an overlay over an image, through an augmented reality device, and so forth.

Aspects of the present disclosure relate to systems, computer readable media, and methods for providing intraoperative video review of surgical procedures. Aspects of the disclosure involve using artificial intelligence and computer image analysis to predict future events in an ongoing surgical procedure, generate an option to review a surgical video clip associated with the expected future event, and output for presentation one or more surgical video clips associated with the expected future event.

In lengthy surgical procedures, a surgeon may conduct numerous intraoperative procedures during a single surgery. Complex surgeries may require several hours for a skilled surgeon to perform. In some cases, a surgeon may wish to review a summary of the intraoperative procedures that the surgeon has performed up to a critical point in the surgery before moving on to a next step in the surgery. In other cases, a second surgeon may enter the operating room and need to review a summary of intraoperative procedures that the first surgeon has already performed in an ongoing surgery. In yet other cases, an inexperienced surgeon may forget to perform an essential intraoperative procedure which could lead to a bad patient result if not corrected before proceeding with the surgery. However, manual recall of all intraoperative procedures performed thus far in a surgery is cumbersome because the quantity of intraoperative procedures is too numerous for a surgeon to recall and may be prone to error. In addition, manual recall can distract the surgeon from the ongoing intraoperative procedures. In other situations, such as in residency training programs, the surgeon may lack the experience required to properly identify all necessary intraoperative procedures in a surgery. Existing methods of presenting video during intraoperative procedures suffer from lack of automation. For example, existing systems are often inflexible and are unable to automatically predict future events and identify relevant videos based on current video data.

Therefore, there is a need for unconventional approaches to enable a user to review intraoperative procedures using video by receiving a surgical video clip associated with an expected future event in a surgical procedure, the expected future event determined through machine learning enabled video processing analysis of a video feed of an ongoing surgical procedure.

Aspects of this disclosure may relate to intraoperative video review. Intraoperative video review may involve the examination and assessment of a collection of video frames from an ongoing surgical procedure. Intraoperative video review may be presented to a medical professional through a video display device such as a screen (e.g., an OLED, QLED LCD, plasma, CRT, DLPT, electronic paper, or similar display technology), a light projector (e.g., a movie projector, a slide projector), a 3D display, screen of a mobile device, electronic glasses (e.g., augmented reality glasses or other augmented reality display), virtual reality devices, or any other form of visual and/or audio presentation.

Some embodiments may include receiving a plurality of video frames. A plurality of video frames may refer to a grouping of frames from one or more surgical videos or surgical video clips. The video frames may be stored in a common location or may be stored in a plurality of differing storage locations. Although not necessarily so, video frames within a received group may be related in some way. For example, video frames within a set may include frames, recorded by the same capture device, recorded at the same facility, recorded at the same time or within the same timeframe, depicting surgical procedures performed on the same patient or group of patients, depicting the same or similar surgical procedures, or sharing any other properties or characteristics.

In some embodiments, the plurality of video frames is from a surgical video feed. A surgical video feed may refer to any video, group of video frames, or video footage including representations of an ongoing surgical procedure. For example, the surgical video may include one or more video frames captured during a surgical operation. A surgical procedure may include any set of medical actions associated with or involving manual or operative activity on a patient's body. Surgical procedures may include one or more of surgeries, repairs, ablations, replacements, implantations, implantations, extractions, treatments, restrictions, re-routing, and blockage removal. Such procedures may involve cutting, abrading, suturing, extracting, lancing or any other technique that involves physically changing body tissues and/or organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally invasive surgery for intracerebral hemorrhage evacuation, veterinarian surgery, or any other medical procedure involving some form of incision. While the present disclosure is described in reference to surgical procedures, it is to be understood that it may also apply to other forms of medical procedures, or procedures generally.

The surgical video feed may be from an ongoing surgical procedure. An ongoing surgical procedure may be a surgical procedure that that is currently in progress. The ongoing surgical procedure may be at any stage of the surgical procedure such as a preparation stage, an injection, an incision, an implantation, a wound sealing, a cleaning, or any other stage of a surgical procedure. The surgical video feed from an ongoing surgical procedure is not limited to the time a patient is in the operating room and may include video of preparation activities or cleanup activities in an operating room before the entry of the patient and after the egress of the patient. Surgical video feed from an ongoing surgical procedure may be received in real-time or in near real-time. For example, the video of the surgical procedure may be recorded by an image capture device, such as cameras 115, 121, 123, 125, and 127 as shown in FIG. 1, in an operating room, or in a cavity of a patient.

Accessing the video of the surgical procedure may be performed via communication to a computer system through a network such as the system depicted in FIG. 4.

Some aspects of this disclosure involve accessing stored data. Stored data may refer to data of any format that was recorded and/or stored previously. In some embodiments, the stored data may be one or more video files including historical surgical footage or historical data. For example, the stored data may include a series of frames captured during the prior surgical procedures. This stored data is not limited to video files, however. For example, the stored data may include information stored as text representing at least one aspect of the stored surgical footage. For example, the stored data may include a database of information summarizing or otherwise referring to historical surgical footage. In another example, the stored data may include information stored as numerical values representing at least one aspect of the historical surgical footage. In an additional example, the stored data may include statistical information and/or statistical model based on an analysis of the historical surgical footage. In yet another example, the stored data may include a machine learning model trained using training examples, and the training examples may be based on the historical surgical footage. Accessing the stored data may include receiving the stored data through an electronic transmission, retrieving the historical data from storage (e.g., a memory device), or any other process for acquiring data. Additionally or alternatively, accessing the stored data may include generating the stored data, for example by analyzing previously recorded surgical procedures or by analyzing data based on the stored surgical footage of prior surgical procedures. The stored data may be in a data structure consistent with disclosed embodiments, such as in FIG. 5 or FIG. 6.

The stored data may be based on prior surgical procedures. Stored data may include any data derived directly or indirectly from images of previous surgical procedures. This data may include, for example, patient characteristics, surgeon characteristics (e.g., a skill level), and/or surgical procedure characteristics (e.g., an identifier of a surgical procedure, an expected duration of a surgical procedure). Stored data may include correlations or other data describing statistical relationships between historical intraoperative surgical events and historical outcomes. In some embodiments, a data structure may include data relating to recommended actions, alternative courses of action, and/or other actions that may change a probability, likelihood, or confidence of a surgical outcome. For example, a data structure may include information correlating a break from a surgical procedure with an improved outcome. Depending on implementation, a data structure may include information correlating a skill level of a surgeon, a request for assistance from another surgeon, and outcomes. Similarly, a data structure may store relationships between surgical events, actions (e.g., remedial actions), and outcomes. In one example, a model (such as a statistical model, a machine learning model, a deep learning model, etc.) may be generated based on the prior surgical procedures, and the stored data may include the generated model and/or an indication of at least part of the generated model. For example, a machine learning model and/or a deep learning model may be trained using training examples based on the prior surgical procedures. While a host of correlation models may be used for prediction as discussed throughout this disclosure, exemplary predictive models may include a statistical model fit to historical image-related data (e.g., information relating to remedial actions) and outcomes; and a machine learning models trained to predict outcomes based on image-related data using training data based on historical examples.

Accessing stored data may include accessing stored historical data identifying intraoperative events, associated outcomes, or a recommended sequence of events. As used herein, an intraoperative event for the surgical procedure (also referred to as a surgical event) may refer to an action that is performed as part of a surgical procedure, such as an action performed by a surgeon, a surgical technician, a nurse, a physician's assistant, an anesthesiologist, a doctor, any other healthcare professional, a surgical robot, and so forth. The intraoperative surgical event may be a planned event, such as an incision, administration of a drug, usage of a surgical instrument, an excision, a resection, a ligation, a graft, suturing, stitching, or any other planned event associated with a surgical procedure or phase. Additionally or alternatively, an intraoperative event may also refer to an event occurring to an anatomical structure and/or to a medical instrument related to the surgical procedure, whether the event includes an action performed by a healthcare professional or not. One example of such an intraoperative event may involve a change in a condition of an anatomical structure.

Figure 10:
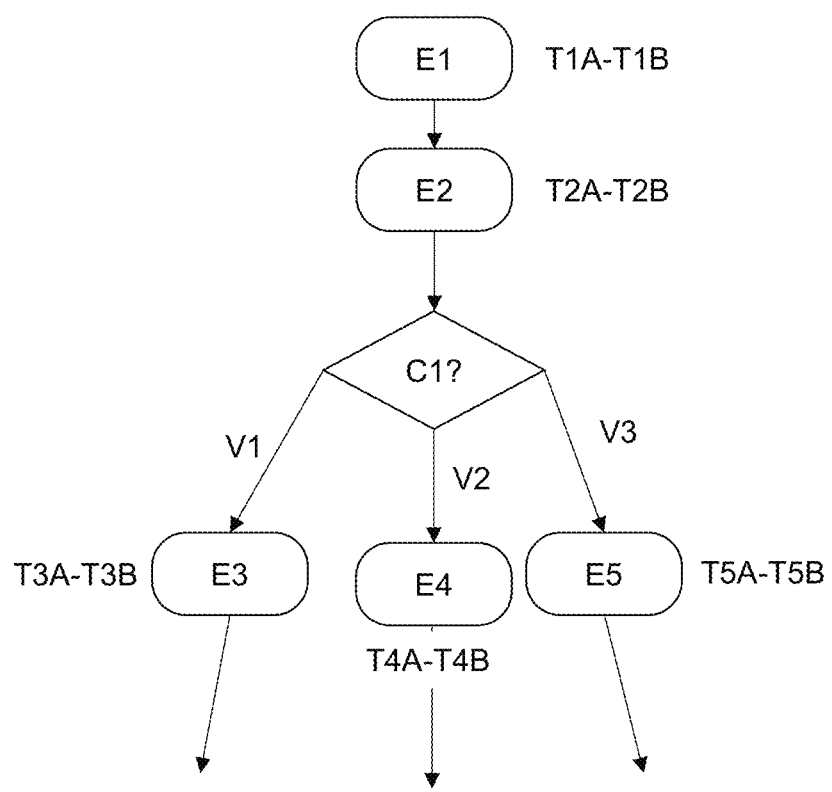
FIG. 10 is a schematic illustration of an exemplary sequence of events, consistent with disclosed embodiments.

An example recommended sequence of events 1001 is schematically illustrated in FIG. 10. For example, an event E1 (e.g., connecting a heart-lung bypass machine) may be a first event in the recommended sequence. Event E1 may be required to occur during a time interval T1A-T1B of the surgical procedure. An event E2 (e.g., suturing), may be a second event and may be required to occur during a time interval T2A-T2B of the surgical procedure (or in other examples, during a time interval T2A-T2B after the completion of event E1, during a time interval T2A-T2B after the beginning of event E1, and so forth). After completion of event E2, a conditional statement C1 (e.g., determining a pulse of a patient's heart) may be evaluated. If conditional statement C1 evaluates to value V1 (e.g., if the patient has no pulse), an event E3 (e.g., activate the heart-lung bypass machine) may be required during a time interval T3A-T3B. If statement C1 evaluates to value V2 (e.g., pulse of ten beats per minute) an event E4 (e.g., administer a first medicine to the patient) may be required during a time interval T4A-T4B, and if statement C1 evaluates to value V3 (e.g., pulse of hundred beats per minute) an event E5 (e.g., administer a second medicine to the patient) may be required during a time interval T5A-T5B.

Further, comparing the accessed video frames with the recommended sequence of events may include comparing a sequence of the identified events within the video frames with the recommended sequence of events for the surgical procedure. For example, FIG. 11 shows a sequence 1101 of recommended (or mandatory) events and a sequence 1102 of the identified events within the video frames. When comparing sequence 1101 with sequence 1102, a deviation of sequence 1102 from sequence 1101 may be determined. Sequence 1102 may deviate from sequence 1101 in a variety of ways. In some cases, sequence 1102 may have different events than sequence 1101. For example, sequence 1101, as shown in FIG. 11 may have events E1-E4, and sequence 1102 may have events S1-S5. Sequences 1101 and 1102 may be compared for each of intervals I1-I4, as shown in FIG. 11. For example, event E1 of sequence 1101 may be compared with event S1 for interval I1 of the sequences. In an example embodiment, event E1 may deviate from event S1. Alternatively, event E1 may be substantially the same as event S1. In some cases, event E1 may be substantially different from event S1.

In various embodiments, to quantify a difference between event E1 and event S1, a suitable measure function F(E1, S1) may be defined that may have a range of values. In an example embodiment, measure function F may return a single number that determines a difference between events E1 and S1. For instance, if $F(E1, S1)<F_0(E1)$, events E1 and S1 are determined to be substantially the same, whereas if $F(E1, S1)>F_1(E1)$, events E1 and S1 are determined to be substantially different. Herein, values $F_0$ and $F_1$ may be any suitable predetermined threshold values, which may be selected for each type of event (i.e., threshold values $F_0(E1)$ and $F_1(E1)$ for event E1 may be different from threshold values $F_0(E2)$ and $F_1(E_2)$ for event E2). In various cases, events E1 and S1 may be characterized by a set of parameters (also referred to as event characteristics). For example, event E1 may be characterized by parameters $P1_{E1}$-$PN_{E1}$, as shown in FIG. 11. Parameters $P1_{E1}$-$PN_{E1}$ may include words, numbers, or data that may be represented by an array of numbers (e.g., images). For instance, parameter $P1_{E1}$ may indicate a type of event E1 characterized by a text string (e.g., "incision"), parameter $P2_{E1}$ may be a number characterizing a length of the incision (e.g., one centimeter), parameter $P3_{E1}$ may be the depth of the incision (e.g., three millimeters), parameter $P4_{E1}$ may be a location of the incision that may be characterized by two numbers (e.g., {10,20}). The location of incision may be specified by identifying the incision in one or more of the video frames captured during the surgical procedure, and parameter $PN_{E1}$ may indicate a type of surgical tool used for the incision (e.g., "CO2 laser"). Event E1 may have as many parameters as needed to fully characterize the event. Further event E1 may be characterized by a starting time $TS_{E1}$ and a finishing time $TF_{E1}$ which may be defined to any suitable precision (e.g., to a precision of a millisecond). $TS_{E1}$ and $TF_{E1}$ may be represented using any suitable time format (e.g., the format may be hour:minute:second:millisecond) Similarly, event S1 may be characterized by parameters $P1_{S1}$-$PN_{S1}$, starting time $TS_{S1}$, and a finishing time $TF_{S1}$, as shown in FIG. 11. As an illustrative example, parameters $\{P1_{E1}, P2_{E1}, P3_{E1}, P4_{E1}, PN_{E1}, TS_{E1}, TF_{E1}\}$ may be represented by any suitable data structure (e.g., $\{P1_{E1}, P2_{E1}, P3_{E1}, P4_{E1}, PN_{E1}, TS_{E1}, TF_{E1}\}$={"incision", 1 [cm], 3 [mm], {10,20}, "CO2 laser", 13:20:54:80, 13:20:59:76}).

In various embodiments, measure function F(E1, S1) may be defined in any suitable way. As an example embodiment, measure function may be defined as $F(E1, S1) = \Sigma_i (P_{i_{E1}} - P_{i_{S1}}) +$ $\Sigma_k M(P_{k_{E1}}, P_{k_{S1}})$, where $P_{l_{E1}}$ and $P_{1_{S1}}$ are related numerical parameters, when event E1 and event S1 are of the same type (e.g., both events are of type "incision"), where parameters $P_{k_{E1}}$ and $P_{k_{S1}}$ are text strings (or data, such as images, that may be represented by arrays of numbers), and where function M returns zero if text strings $P_{k_{E1}}$ and $P_{k_{S1}}$ contain the same meaning, or returns one if text strings $P_{k_{E1}}$ and $P_{k_{S1}}$ contains a different meaning. For cases when $P_{k_{E1}}$ and $P_{k_{S1}}$ correspond to images, function M may return zero if images are substantially the same or return one if images are different. In various embodiments, the images may be compared using any suitable image recognition algorithm further described below. Alternatively, function M may be configured to execute any suitable algorithm for comparing $P_{k_{E1}}$, and $P_{k_{S1}}$ depending on a type of data represented by parameters $P_{k_{E1}}$, and $P_{k_{S1}}$, where the data may include text strings, an array of numbers, images, videos, audio signals, and the like.

For cases when events E1 and S1 are not of the same type (e.g., event E1 may correspond to "incision" and event S1 may correspond to "administering a medication"), and when sequence 1102 does not contain an event of the same type as event E1, the measure function F(E1, S1) may be evaluated to a large predetermined number (or string) indicating that events E1 and S1 are substantially different.

As described above the deviation between sequence of events 1101 and 1102 may be determined by evaluating a suitable measure function $F(E_i, S_i)$ 53 for each interval of a surgical procedure I1-I4. A complete deviation may be calculated as a sum of measure functions $\Sigma_i(E_i, S_i)$, where i={I1 ... I4}. In various embodiments, however, calculating all the deviations for all of the events S1-S4 from the corresponding events E1-E4 may not be important and/or necessary. In various cases only large deviations (i.e., deviations where $F(E_i, S_i) > F_1(E_i)$ may be important. For such deviations, events $E_i$, $S_i$ may be identified and stored for further analysis. Additionally, a value of measure function $F(E_i, S_i)$ may be stored for further analysis as well. In various embodiments, data related to events $E_i$, $S_i$, and measure function $F(E_i, S_i)$ may be stored using any suitable means (e.g., hard drive, database 411, and the like).

In various embodiments, how well the measure of the deviation coincides with the desired measure of the deviation may be asserted using any suitable, appropriate mathematical measure function G. For example, if a measure of a deviation for an event is a number, (e.g., d), and the desired measure of the deviation is another number (e.g., $d_0$) then an example mathematical measure function for a given event $E_i$ may be $G_i(d, d_0)$ may be $G_i(d, d_0) = d - d_0$, and the measure function may be, for example, a number $G = \Sigma_i G_i(d_i, d_{i_0})^2$. Alternatively, in another example embodiment, G may be a vector $G = \{G_i(d_i, d_{i_0})\}$.

To further illustrate a process of determining the deviation of sequence 1102 from sequence 1101, FIG. 11 shows intervals I1-I4 at which events E1-E4 of sequence 1101 may be compared with events S1-S5 of sequence 1102. For example, during interval I1, event S1 may be substantially the same as event E1, and during interval I2 event S2 may deviate from event E2 but may be sufficiently similar to event E2. For example, event S2 may correspond to "incision" having an incision length of three centimeters, and event E2 may correspond to "incision" having an incision length of two centimeters. In an example embodiment, during interval I3 of the surgical procedure, event E3 may be substantially different from event S3 (e.g., event E3 may be identified as an "incision" and event S3 may be identified as "suturing"). During interval I4, event E4 may be substantially different from event S4 but may be substantially the same (as indicated by arrow 1111, as shown in FIG. 11) as event S5 identified during interval I5. When calculating the deviation of sequence 1102 from 1101, event S4 of sequence 1102 may be identified as an "inserted" event that does not have a corresponding counterpart in sequence 1101. Such characterization of event S4 may be recorded (e.g., stored on a hard drive, database 111, or some other location) for further analysis.

An exemplary surgical intraoperative event for a laparoscopic cholecystectomy surgery may include trocar placement, calot's triangle dissection, clipping and cutting of cystic duct and artery, gallbladder dissection, gallbladder packaging, cleaning and coagulation of liver bed, gallbladder retraction, and so forth. In another example, surgical events of a cataract surgery may include povidone-iodine injection, corneal incision, capsulorhexis, phaco-emulsification, cortical aspiration, intraocular lens implantation, intraocular-lens adjustment, wound sealing, and so forth. In yet another example, surgical characteristic events of a pituitary surgery may include preparation, nasal incision, nose retractor installation, access to the tumor, tumor removal, column of nose replacement, suturing, nose compress installation, and so forth. Some other examples of surgical characteristic events may include incisions, laparoscope positioning, suturing, and so forth.

In some embodiments, the surgical intraoperative event may include an adverse event or a complication. Some examples of adverse surgical events may include bleeding, mesenteric emphysema, injury, conversion to unplanned open surgery (for example, abdominal wall incision), incision significantly larger than planned, and so forth. Some examples of intraoperative complications may include hypertension, hypotension, bradycardia, hypoxemia, adhesions, hernias, atypical anatomy, dural tears, periorator injury, arterial occlusions, and so forth. In some cases, surgical events may include other errors, including technical errors, communication errors, management errors, judgment errors, decision-making errors, errors related to medical equipment utilization, miscommunication, and so forth. In various embodiments, events may be short or may last for a duration of time. For example, a short event (e.g., incision) may be determined to occur at a particular time during the surgical procedure, and an extended event (e.g., bleeding) may be determined to occur over a time span. In some cases, extended events may include a well-defined beginning event and a well-defined ending event (e.g., beginning of suturing and ending of the suturing), with suturing being an extended event. In some cases, extended events are also referred to as phases during a surgical procedure.

In some cases, a surgical event may identify a group of sub-events (i.e., more than one sub-event or steps). For example, an event of administering general anesthesia to a patient may include several steps such as a first step of providing a medication to a patient via an IV line to induce unconsciousness, and a second step of administering a suitable gas (e.g., isoflurane or desflurane) to maintain the general anesthesia.

In some embodiments, operations may include predicting at least one expected future event in the ongoing surgical procedure. Predicting may involve calculating or estimating a likelihood that something will happen in the future (e.g., an occurrence of a future event), determining that something is likely to happen in the future, and so forth. The predicting may occur using one or more artificial neural networks, as discussed herein. For example, a future event may be associated with a likelihood of occurrence generated using a model, and an expected future event may be predicted based on the likelihood of occurrence and a threshold. An expected future event may be associated with various likelihoods. For example, an expected future event may be more likely than not, it may be the most likely event in a set possible future events, a top N-events in a list of events, or it may meet a threshold likelihood. In some embodiments, an expected future event in the ongoing surgical procedure may be associated with a predetermined assessment point. For example, the system may determine that the future expected event is a wound closure, at which time the surgeon may wish to assess whether all necessary intraoperative events required to be completed before performing the wound closure have been performed. Predetermined assessment points are not limited to wound disclosures and may be associated with any intraoperative events, such as a pre-incision check, a pre-suturing check, an anesthesia safety check, an evaluation of airways/aspiration risks, a check of patient or procedural data, or any other intraoperative event. The future expected event may be a complication, such as the adverse events and complications discussed earlier. Future expected events are not limited to events associated with predetermined assessment points or complications and may include any intraoperative event associated with a surgical procedure.

Some embodiments may include analyzing at least some of the plurality of video frames to determine an intraoperative event therein. Analyzing the received video frames to determine an intraoperative event therein may involve any form of electronic analysis using a computing device (i.e., computer image analysis, for example using action recognition algorithms). The analysis may involve artificial intelligence applied to the video frames, such as through the use of an artificial neural network, as described herein.

Predicting a future event may be based on computer image analysis. For example, a future event may be predicted using a model trained to output a likelihood of occurrence of a future event. Future events may be predicted based on a correlated, a regression result, or other statistical relationship with a predetermined assessment point, a determined event or other information derived from video data. Additionally or alternatively, future events may be predicted based on an analysis of stored data associated with a video. Such analyses may employ machine vision to assess video images and artificial intelligence to compare assessed video images with prior assessed video images. In one example, image-based information (such as video frames, selected portions of video frames, results of analysis of the video frames, one or more convolutions of portions of the video frames, etc.) may be used together with temporal information (such as elapsed time since the beginning of the surgical procedure, elapsed time since a particular event within the surgical procedure, etc.) to predict the future event. In one example, an entry in a table may be selected based on the image-based information and the temporal information, and the entry may specify the prediction of the future event. For example, the table may be based on the stored data and/or on the prior surgical procedures. In another example, the table may be based on a particular surgeon participating in the ongoing surgical procedure, using a first table for a first particular surgeon, and a second table for a second particular surgeon, the second table may differ from the first table. In some examples, video frames may be analyzed to identify an entry of a particular surgical tool to a selected region (such as the field of view of the camera, a selected portion of a video frame, a region in a vicinity of particular part of the patient, etc.), and the prediction of the future event may be based on the particular surgical tool and/or on the selected region.

Predicting a future event may be based on an event-based machine learning model such as those described in reference to FIGS. 8A and 8B.

Aspects of disclosed embodiments may include analyzing the received plurality of video frames and, based on information obtained from stored data, identifying in the accessed frames at least one intraoperative event. As previously described, and consistent with various embodiments, a process of analyzing the accessed frames may be performed by a suitable machine-learning model such as an image recognition algorithm, as described above. In various embodiments, information obtained from historical data may be used to train and/or calibrate the image recognition algorithm to recognize specific intraoperative events base on accessed frames of surgical footage, as previously described. In one example, the historical data may include a statistical model and/or a machine learning model based on an analysis of information and/or video footage from historical surgical procedures (for example as described above), and the statistical model and/or the machine learning model may be used to analyze the accessed frames and identify in the accessed frames the at least one specific intraoperative event.

Figure 12:
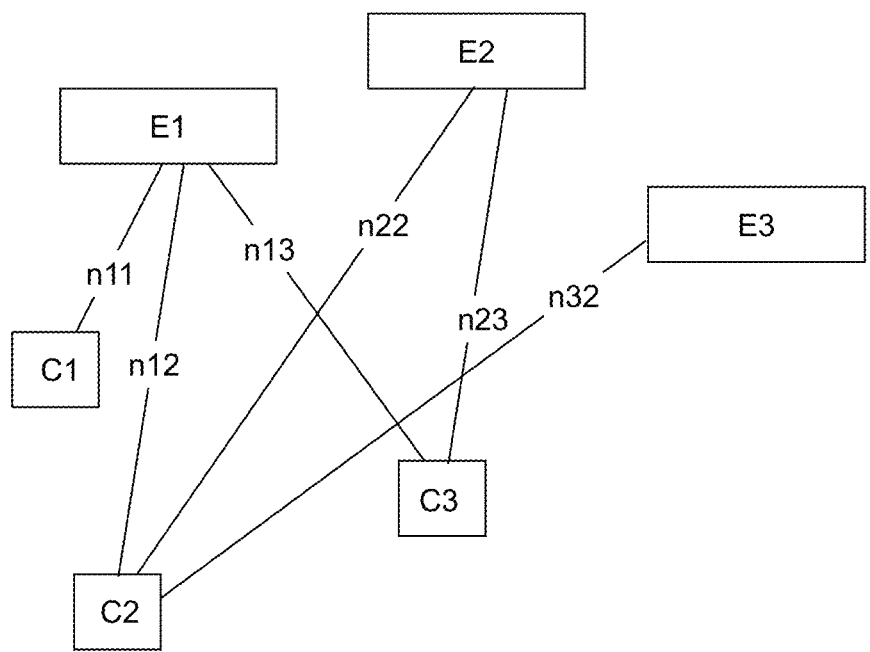
FIG. 12 is an exemplary graph showing a relationship between intraoperative events and outcomes, consistent with disclosed embodiments.

Aspects of this disclosure may include predicting, based on the plurality of video frames and the stored data based on prior surgical procedures, at least one expected future event in the ongoing surgical procedure. For example, a data structure may include stored data representing relationships between intraoperative events and predicted outcomes. Such data structures may be used to obtain a predicted outcome associated with a specific surgical procedure. For example, FIG. 12 shows an example graph 1200 of intraoperative events E1-E3 connected to possible outcomes C1-C3 using connections n11-n32. Connection n11 may include information indicating a probability of an outcome C1 (i.e., information indicating how often outcome C1 happens in surgical procedures that includes event E1). In some aspects, connection n11 may indicate that given an occurrence of intraoperative event E1, outcome C1 may happen 30 percent of the time, connection n12 may indicate that outcome C2 may happen 50 percent of the time, and connection n13 may indicate that outcome C3 may happen 20 percent of the time. Similarly, connection n22 may indicate a probability of outcome C2, given an occurrence of intraoperative event E2, and connection n23 may indicate a probability of outcome C3, given an occurrence of intraoperative event E2. A connection n32 may indicate a probability of outcome C2, given an occurrence of intraoperative event E3. Thus, once an intraoperative event is known, using information obtained from historical data (e.g., using information from graph C100), a most probable outcome (e.g., outcome C2) may be determined based on probability assigned to connections n11-n13. In another example, the historical information may include a hypergraph, a hyperedge of the hypergraph may connect a plurality of intraoperative events with an outcome and may indicate a particular probability of the outcome in surgical procedures that included the plurality of events. Thus, once a plurality of intraoperative events is known, using information obtained from historical data (e.g., from the hypergraph), a most probable outcome may be determined based on probability assigned to the hyperedges. In some examples, probabilities assigned to edges of graph C100 or to the hyperedges of the hypergraph may be based on an analysis of historical surgical procedures, for example by calculating the statistical probability of an outcome in a group of historical surgical procedures that include particular group of intraoperative events corresponding to a particular edge or a particular hyperedge. In some other examples, the historical information may include a trained machine learning model for predicting outcome based on intraoperative events, and the trained machine learning model may be used to predict the outcome associated with the specific surgical procedure based on the identified at least one intraoperative event. In one example, the trained machine learning model may be obtained by training a machine learning algorithm using training examples, and the training examples may be based on historical surgical procedure. An example of such training example may include a list of intraoperative surgical events, together with a label indicating an outcome corresponding to the list of intraoperative surgical events. In one example, two training examples may have the same list of intraoperative surgical events, while having different label indicating different outcomes.

Figure 13:
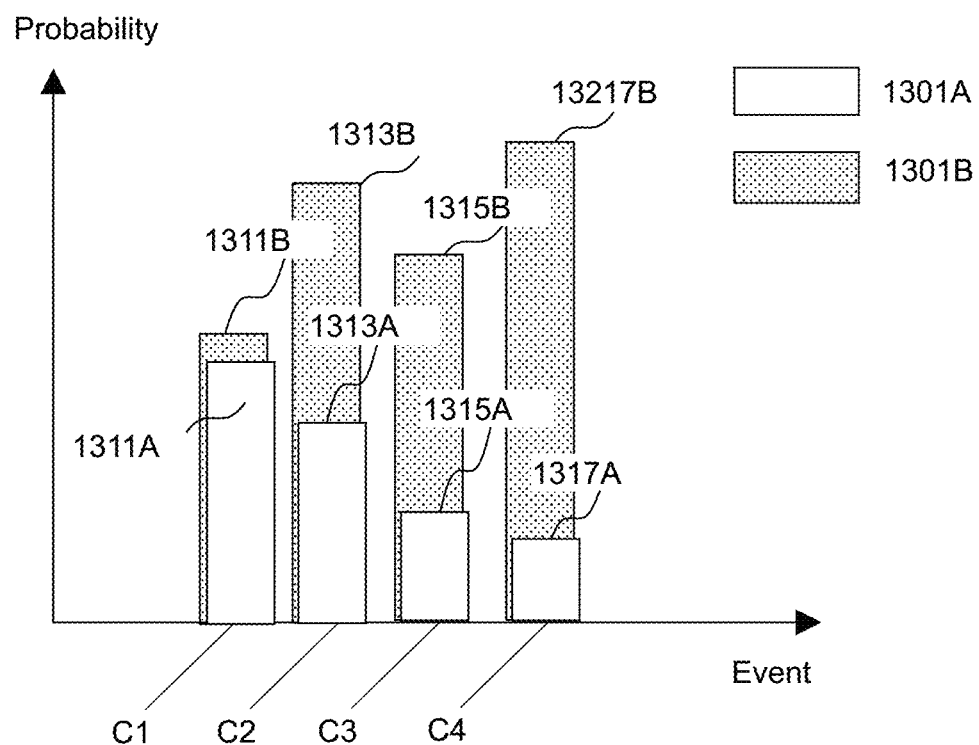
FIG. 13 is an exemplary probability distribution graph for different events with and without the presence of an intraoperative event, consistent with disclosed embodiments.

The predicting of the expected future event associated with the surgical procedure based on the received plurality of video frames may be accomplished using a statistical analysis. For example, historical surgical data for past (also referred to as historical) surgical procedures containing an intraoperative event, may be analyzed to determine a historical outcome for such past surgical procedures. For example, for a given type of a historical surgical procedure, surgical outcome statistics may be collected, as shown in FIG. 13. For instance, a probability distribution 1301A represented by bars 1311A-1317A (herein also referred to as probability bars) may determine a probability of corresponding outcomes C1-C4, when an intraoperative event is not present (e.g., when an adverse intraoperative event such as bleeding, cardiac arrest, or any other adverse event is not present). Similarly, probability distribution 1301B represented by probability bars 1311B-1317B may determine a probability of corresponding outcomes C1-C4 when the intraoperative event (e.g., an adverse intraoperative event) is present. In an example embodiment, outcome C1 may correspond to a specific post-discharge mishap (e.g., a foreign object such as gauze is left in a patient's body), outcome C2 may correspond to a specific post-discharge adverse event (e.g., bleeding, pain, nausea, confusion, or any other adverse event), outcome C3 may correspond to a post-discharge complication (e.g., paralysis, pain, bleeding, or any other complication), and outcome C4 may correspond to an elevated risk of readmission. It should be noted that any other suitable outcomes may be used to evaluate the surgical procedure (e.g., an outcome that evaluates an objective measure of a patient's "well-being" several days after the surgical procedure). In an example embodiment, the height of probability bars 1311A-1317A and 1311B-1317B may relate to a probability of occurrence of corresponding outcomes C1-C4.

In an example embodiment, an intraoperative event may affect the probabilities of occurrence of outcomes C1-C4, as shown by bars 1311B-1317B that have different heights than corresponding bars 1311A-1317A. In an illustrative example, if the intraoperative event corresponds to a cardiac arrest during a surgical procedure, bar 1313B corresponding to a probability of outcome C2 (e.g., confusion) may be higher than bar 1311B corresponding to a probability of outcome C2 when the intraoperative event was not detected during the surgical procedure.

Figure 14:
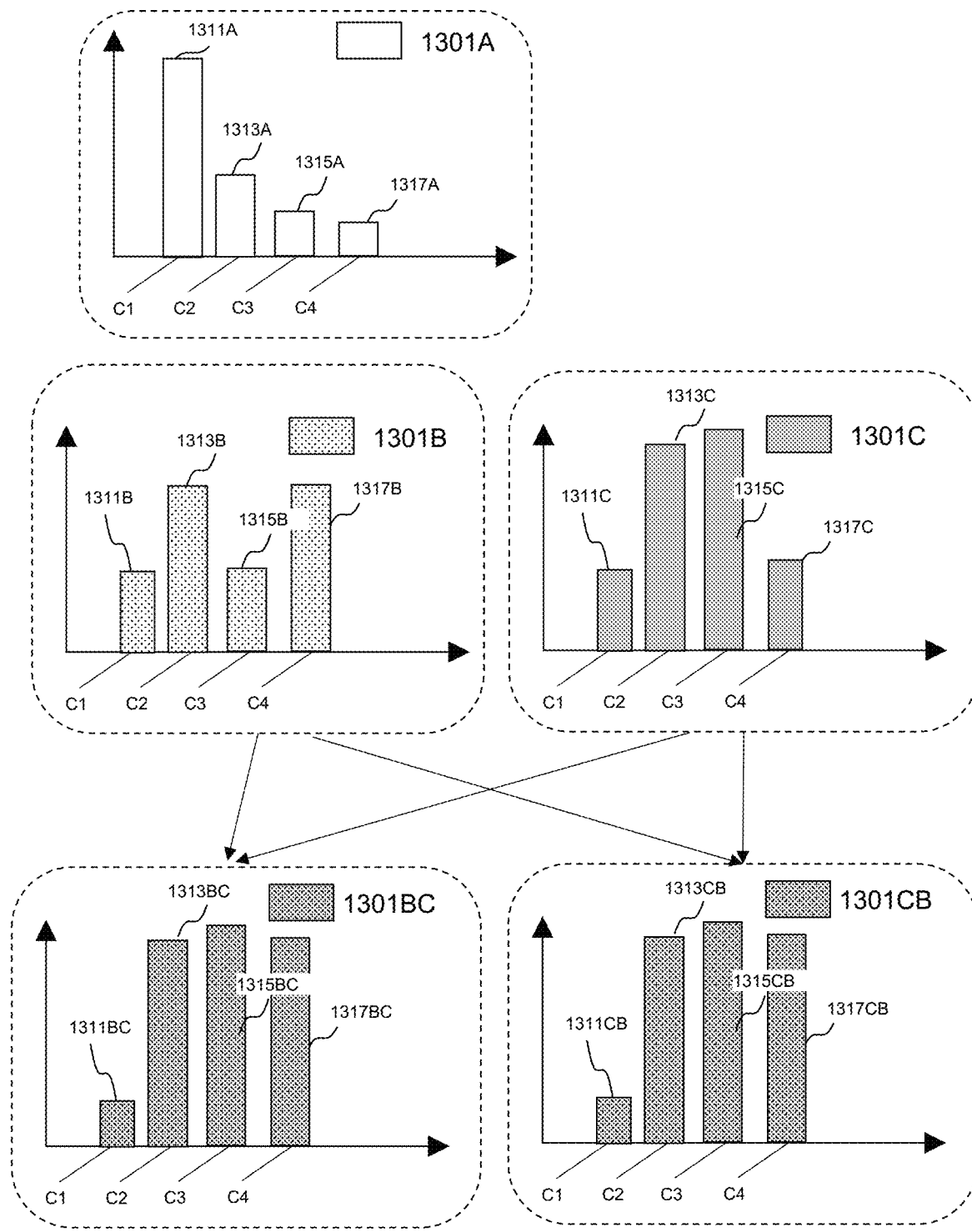
FIG. 14 shows exemplary probability distribution graphs for different events, consistent with disclosed embodiments.

In some cases, a statistical analysis may be used to determine the predicted outcome associated with the surgical procedure based on a determination of several intraoperative events that may occur during the surgical procedure. For example, FIG. 14 shows a probability distribution 1301A with probability bars 1311A-1317A corresponding to probability for outcomes C1-C4 when there are no adverse intraoperative events present (as described above). FIG. 14 also show a probability distribution 1301B with probability bars 1311B-1317B corresponding to probability for outcomes C1-C4 when there is a first adverse event labeled "B" present during a surgical procedure. Likewise, FIG. 14 also shows a probability distribution 1301C with probability bars 1311C-1317C corresponding to probability for outcomes C1-C4 when there is a second adverse event labeled "C" present during a surgical procedure. Further, using statistical data for surgical procedures that include event "B" and event "C", with event "B" starting prior to a start of event "C", the probability distribution 1301BC may be determined as shown by bars 1311BC-1317BC corresponding to probability for outcomes C1-C4.

Figure 15:
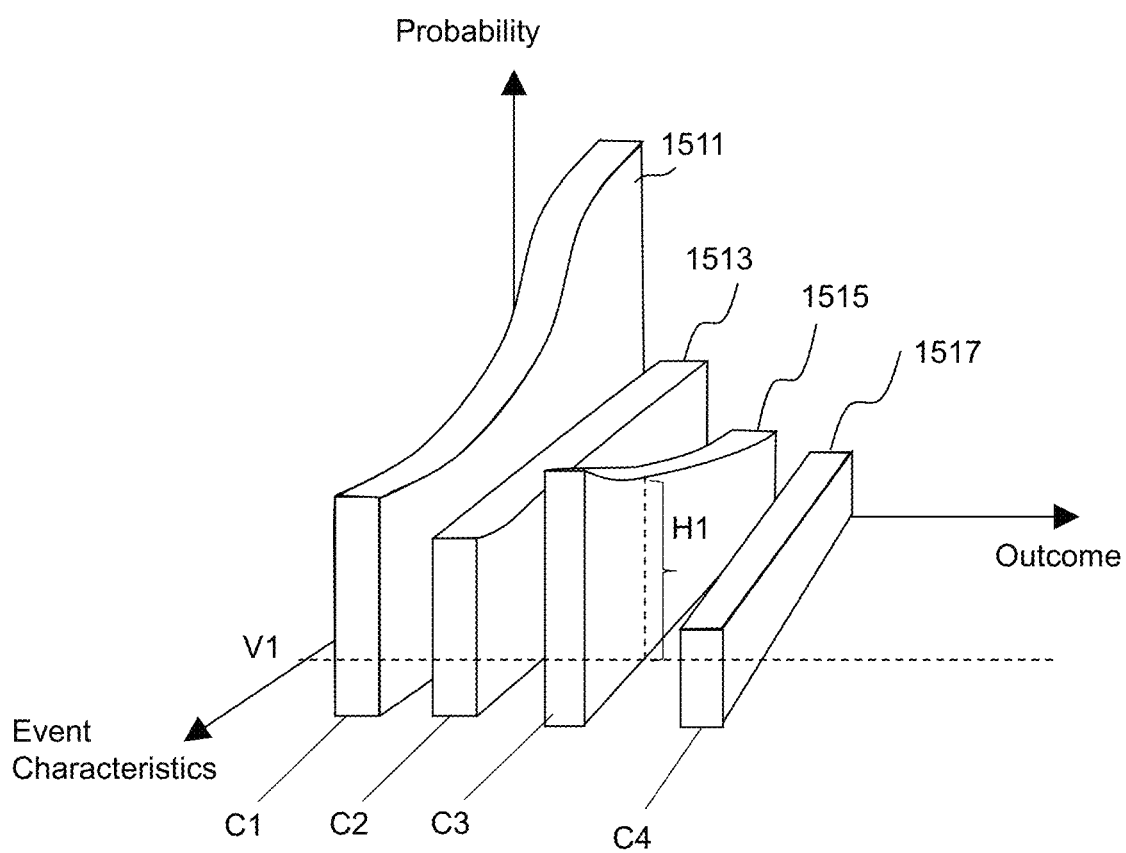
FIG. 15 shows exemplary probability distribution graphs for different events, as a function of event characteristics, consistent with disclosed embodiments.

Additionally or alternatively, using statistical data for surgical procedures that include event "B" and event "C", with event "B" starting after the start of event "C", the probability distribution 1301CB may be determined as shown by bars 1311CB-1317CB corresponding to probability for outcomes C1-C4. It should be noted that other probability distributions (besides distributions 1301B, 1301C, 1301BC, and 1301CB) may be determined using a suitable statistical data depending on various characteristics of events "B", and/or "C" and/or combination of thereof. For instance, an event characteristic may include a duration of time for the event, a starting time for the event, a finishing time for the event, or any other suitable characteristic (e.g., if an event is an incision, an event characteristic may be a length of the incision; if the event is a cardiac arrest, the event characteristics may be blood pressure values during the cardiac arrest; or any other suitable characteristic). An example embodiment of how the probability distribution is affected by an event characteristic is shown in FIG. 15 by plotting heights of bars 1511-1517 corresponding to probability for outcomes C1-C4 in a three-dimensional Cartesian system. As shown in FIG. 15, one axis is a probability for outcomes C1-C4, another axis denotes the outcome (e.g., outcomes C1-C4), and the third axis denotes "Event Characteristics" of an intraoperative event and is represented by a numerical value (herein referred to as the event characteristic value) such as, for example, incision length for intraoperative event being an incision. FIG. 15 shows that bar heights for bars 1511-1517 may change continuously as the event characteristic value changes, while in other examples the event characteristic value may be discrete. For a given event characteristic value (e.g., V1, as shown in FIG. 15) the height value (e.g., H1) for an example bar (e.g., 1515), corresponding to a probability of outcome C3 in case of an event characteristic V1, may be interpolated using nearby height values for bar 1515, when height value H1 is not known for value V1.

In an illustrative example, the system may receive video frames from an ongoing kidney transplant procedure. Using the video analysis techniques disclosed herein, the system may determine a list of intraoperative events that have been performed during the procedure. The system may access stored data containing a complete list of ordered intraoperative events associated with the kidney transplant procedure. Based on the intraoperative events depicted in the plurality of video frames and on the stored data, the system may determine that an expected future event in the ongoing kidney transplant surgical procedure is to close the incision point.

In another illustrative example, the system may determine a list of intraoperative events that have been performed during the procedure, and after accessing stored data containing a complete list of ordered intraoperative events associated with the procedure, the system may determine that an essential intraoperative event was omitted. The system may then determine that the expected future event may be a complication based on the omitted intraoperative event. For example, the system may receive video frames depicting the closure of an incision point, often performed near the completion of a surgical procedure. The system may determine a list of intraoperative events that have been performed during the procedure, compare this list to stored data based on prior surgical procedures, and determine that an intermediate step to suture an internal organ was omitted from the procedure. The system may then determine that an expected future event may be an internal bleeding based on this internal step being omitted. Predicting at least one expected future event in the surgical procedure is not limited to the forgoing examples and may include any number of future events in a surgical procedure such as a fluid leak, a bleeding, a decision making junction, an operative milestone, or a next step in a planned surgical procedure.

Some embodiments may include generating at least one option to review at least one surgical video clip. An option may include a prompt on a graphical user interface inviting selection by the user to facilitate review of surgical video frames. The option may correspond to a menu depicting choices of video clips for display. The option may be presented to a user through a user interface of a user device, such as a desktop computer, a laptop, a table, a mobile phone, a wearable device, an augmented reality device, a virtual reality device, an internet of things (IoT) device, or any other means for receiving input from a user. A surgical video clip may be a collection of surgical video frames. Surgical video clips may be stored in the same location or may be selected from a plurality of storage locations. Although not necessarily so, surgical video frames within a surgical video clip may be related in some way. For example, surgical video frames within a surgical video clip may include frames, recorded by the same capture device, recorded at the same facility, recorded at the same time or within the same timeframe, depicting surgical procedures performed on the same patient or group of patients, depicting the same or similar surgical procedures, depicting surgical procedures sharing a common characteristic (such as similar complexity level, including similar events, including usages of similar techniques, including usages of similar medical instruments, etc.), depicting a specific intraoperative event, or sharing any other properties or characteristics. Surgical video clips may include video frames from the ongoing surgical procedure or from one or more previous surgical procedures. Surgical video clips from the previous surgical procedures may be related in some way, such as sharing common intraoperative events, being performed by common medical professionals, being performed on patients with similar characteristics such as age, gender, body weight, or pre-existing conditions, previous medical treatments, sharing common complications, or they may be unrelated.

The at least one surgical video clip may be associated with the expected future event in the surgical procedure. Using machine vision and or other artificial intelligence techniques described herein and applied to both the current surgical procedure and past surgical procedures, the system may be able to predict an upcoming future surgical event, and present for viewing during the surgery an option to view at least one related video clip. By way of example, an expected future event may be removal of an organ. Using artificial intelligence applied to the video of the ongoing surgical procedure, the system may determine that the surgery is nearing a point in the surgical timeline where the organ removal will take place. To prepare the surgeon or the team for that future event, the system may identify stored prior surgical footage of similar removals performed on one or more other patients and make that clip available for viewing. This may help the surgeon or other members of the surgical team prepare for the future event. More than one option may be presented for viewing. For example, one or more options may demonstrate complications that previously occurred during other organ removals, and one or more options may demonstrate prior procedures that were complication free. Additionally, or alternatively, one or more options may present differing techniques for performing the removal. The system may select the options based on similarities between the patient undergoing surgery and patients in prior recorded surgeries. For example, if the current patient is an obese 45-year-old male with diabetes, the system may seek to select video clips from prior patients sharing similar characteristics. These characteristics may be identified from patient medical records, from video, or from both.

The system may generate an option to review a video clip. Generating an option refers to any manner of providing a viewer with an ability to view associated video. It may include for example, identifying relevant video clips and presenting via a user interface, and ability to view the option. An option may be presented automatically once generated, or, a viewer may be provided with a pick list or other mechanism for choosing clips of interest. Options may be presented with textual summaries. For example, the textual video summary might identify a particular complication presented in a particular clip, or a particular technique used in a particular clip. This may provide the surgeon or other viewer with the ability to choose clips of interest for playback. The viewer may have the ability to speed up, slow down, skip, or replay portions of video clips, either through a touch screen interface, a foot pedal, an AR interface, or any other control mechanism.

In another example, an expected future event may be a complication, such as an internal bleeding predicted based on an occurrence during the ongoing surgical procedure. Thus, for example, if a complication occurs during a surgical procedure, the system may be able to demonstrate to members of the surgical team an occurrence expected to result from that complication, permitting the team to take steps to avert or prepare for the expected occurrence.

The at least one option to review at least one surgical video clip may be generated for intra-surgical presentation. In other words, the option to review may be presented to the user in the operating room while surgery is in progress. The option to review may be presented through a user interface of a user device or a display device of the type disclosed herein. In some examples, the at least one option to review at least one surgical video clip presenting prior events in the ongoing surgical procedure, for example prior events in the ongoing surgical procedure that are associated with the expected future event in the surgical procedure. For example, a subset of the plurality of video frames from the surgical video feed of the ongoing surgical procedure may be selected, for example the subset may be selected to be associated with the expected future event in the surgical procedure, and the at least one surgical video clip may include and/or be based on the selected subset. In one example, the selected subset may depict prerequisites of the expected future event. In one example, at least one frame of the plurality of video frames from the surgical video feed of the ongoing surgical procedure is not included in the selected subset.

Aspects of this disclosure may include accessing a data structure containing the at least one surgical video clip. The data structure may be of the type disclosed herein. Accessing the data structure may include interfacing with the stored data through an electronic link or address. For example, if a surgeon selects an option to view a particular video clip, the selection may include an embedded link or address to a corresponding video clip stored in a data structure. This might occur through a lookup table, or the link or address might point to a specific location where a corresponding video clip is stored on a server. Thus, if multiple video clip options are presented to the surgeon, each option might contain a link the activation of which enables access to a corresponding video clip stored in a data structure. Accessible video clips may be stored in multiple locations or in a common location, depending on system architecture. In one example, the data structure may be a file system, and the at least one surgical video clip may be stored in one or more files within the file system. In one example, the data structure may be a file, and the at least one surgical video clip may be stored in the file. In one example, the data structure may be a database, and the at least one surgical video clip may be stored in the database. In one example, the data structure may be configured to store a sequence of values, and the at least one surgical video clip may be encoded in the sequence of values.

Some aspects of the present disclosure may include outputting for intra-surgical presentation, the at least one surgical video clip associated with the expected future event. Outputting for intra-surgical presentation may include outputting code from at least one processor, wherein the code may be configured to cause the surgical video clip to be presented. Thus, for example, after a user such as a surgeon selects a video clip for viewing and that clip is accessed, the clip may be outputted from its source (e.g., a server) for presentation during a surgical procedure. The presentation may be any form of visual display including the compilation of frames. In some embodiments the presentation may be a compilation video. The presentation may include other elements, such as menus, controls, indices, timelines, or other content in addition to the compilation. The output may be configured to cause a visual presentation on a display device, such as those described earlier. In some embodiments, the display device may be located in the operating room, facilitating review of the presentation during an on-going surgery. Consistent with the present embodiments, outputting the surgical video clip may include storing the presentation in a location that may be accessible by one or more other computing devices. Such storage locations may include a local storage (such as a hard drive of flash memory), a network location (such as a server or database), a cloud computing platform, or any other accessible storage location. Accordingly, the presentation may be accessed from an external device to be displayed on the external device. In some embodiments, outputting the surgical video clip may include transmitting the video to an external device. For example, enabling the surgeon to view the presentation may include transmitting the presentation through a network to a user device or other external device for playback on the external device. In one embodiment, the expected future event may be a wound closure, and the at least one surgical video clip may be configured to enable a pre-closure surgical review. For example, when the system detects that a surgery is nearing closure, the system may present an option to enable a surgical review of the highlights of the current surgical procedure. In other words, the system is configured to playback to members of the surgical team, prior footage of the ongoing surgery. This may enable the team to review their work before closing. In instances where there is a surgical count disparity, summary video may indicate a location in the surgical cavity where an instrument, sponge, sharp, sutures or miscellaneous items were last seen. This may occur via artificial intelligence, as the system may keep track of the instruments that were not removed from the surgical cavity and may automatically play back during the pre-closure surgical review, clips of those locations. Aside from assisting with surgical counts, the pre-closure surgical review might consolidate for playback key moments in the surgery, such as instances that typically give rise to posts-surgical complications. These key moments might be learned through artificial intelligence performed on the video footage to isolate for playback those portions of the surgical footage that is relevant for the surgical team to check before closing. This feature improves patient outcomes by creating video evidence of the intraoperative events conducted by the surgeon in advance of the wound closure, allowing the surgeon to verify that all necessary intraoperative events were satisfactorily completed. Creation of video evidence documenting the intraoperative events and displaying them in real time reduces the risk of surgeon error in omitting an intraoperative event and removes distractions from the surgeon by eliminating the need for human recall of intraoperative events.

In some embodiments, outputting for intra-surgical presentation includes generating a composite video presentation including clips from a plurality of prior surgical procedures. For example, surgical video clips may include frames from multiple surgical procedures and may contain multiple intraoperative events. The plurality of surgical procedures may be of the same type, for example, all including appendectomies, or may be of different types. In some embodiments, the plurality of surgical procedures may share common characteristics, such as the same or similar phases or intraoperative events. For example, a composite clip might show a procedure being performed incorrectly, followed by a clip of the correct procedure. This might demonstrate to the surgeon what to do and what not to do. By way of another example, a composite video presentation might include clips of differing techniques for handling the same procedure, thereby providing the surgeon with differing surgical options. In another example, the composite might include clips from patients having anatomical differences so that the surgeon is able to be prepared if such a difference is encountered.

Aspects of this disclosure may include accessing information characterizing a current patient undergoing the surgical procedure. Information characterizing a current patient may include characteristics of the patient, including age, gender, weight, height, or preexisting medical conditions. In some embodiments, the at least one surgical video clip may be selected to reflect video of at least one prior patient sharing characteristics with the current patient. For example, the surgical video clips may include frames from patients with common characteristics as the current patient, such as patients of the same gender, age, medical history, or common preexisting medical condition such as obesity, or high blood pressure. Medical histories may be considered similar if both the current patient and a patient in the prior surgical video share a prior medical condition such as, for example, heart attack, or common orthopedic implants. Information characterizing a current patient may include any stored information and is not limited to the patient characteristics described here. Such characterizing information may be accessed from surgical video, medical records, or both.

In some embodiments, following the outputting for intra-surgical presentation, additional options to review additional surgical video related the at least one surgical video clip outputted for presentation are presented. A surgeon may wish to view more than the selected surgical video. For example, a video clip showing a removal of a tumor may be outputted. The surgeon may be presented with additional options to view additional surgical videos depicting removal of additional tumors. In this way, the surgeon may review many examples of the same or similar intraoperative event. After video clip review, more options for selection may be automatically presented. Alternatively or additionally, the interface may include a button that enables the viewer to access other examples.

In some embodiments, the surgical video clip includes selected portions of the surgical video feed of the ongoing surgical procedure captured before the generation of the at least one option. For example, a surgeon may wish to review a video clip depicting a summary of certain critical steps performed in the surgery and may not wish to review the entire video of the surgical procedure when presented with the option to review. In some embodiments, a summary of the surgical procedure may be presented wherein at least one video frame of the surgical video feed of the ongoing surgical procedure is not included in the surgical video clip. In some embodiments, the operations may further comprise selecting the portions of the surgical video feed based on the predicted at least one expected future event in the ongoing surgical procedure. For example, the system may determine, through accessing stored data, that only a subset of video frames of the ongoing surgical procedure is associated with a predicted future event. In one example, the expected future event may be that the patient leaves the operating room at the conclusion of the procedure. The system may present the option to review a surgical video clip of critical intraoperative events of that patient's surgical video that relate to an event predicted to occur later in the surgical procedure. For example, if a bleed is predicted to occur later because a particular suture was incomplete, the surgeon may be shown video clips of the incomplete suture in the current surgery in order to help the surgeon understand the source of the bleed. One or more video clips of similar bleeds in other surgeries may also be presented to the surgeon providing examples of how to rectify the situation. The video clip may omit video frames not associated with the expected future event, such as patient preparation or video frames not associated with intraoperative events, or frames associated with inactivity.

In some embodiments, the operations may further comprise determining at least one prerequisite of the predicted at least one expected future event in the ongoing surgical procedure. A prerequisite of an expected future event may be an intraoperative event that should occur or must occur to facilitate the expected future event. A prerequisite of a predicted expected future event may be determined in advance by a medical professional, may be determined through the computer image analysis techniques disclosed herein, or may be determined by a hospital group or board of medical professionals. A prerequisite may be a single intraoperative event, or it may be a plurality of prerequisites representing more than one intraoperative event. Prerequisites may be stored in a data structure and associated with surgical video clips as disclosed herein. The system determines a prerequisite by accessing a data structure of the type disclosed herein that contains prerequisite data associated with the expected future event. For example, the system may determine certain prerequisites to the expected future event of closing a surgical patient such as removal of patient tissue, removal of all operating equipment and surgical tools, suturing of any internal bleeding, or other appropriate intraoperative events.

In some embodiments, the selected portions of the surgical video feed of the ongoing surgical procedure are configured to enable a surgeon to verify the at least one prerequisite. The system may enable display of that perquisite, in the form of a video clip to the surgeon. For example, prior to an organ removal, particular vessels may need to be tied-off. In association with presenting to the surgeon an ability to see video clips of an organ removal from a similar prior surgery the surgeon, the system may also provide the surgeon with the ability to view in video footage of the current surgery, the prerequisites. This may enable the surgeon to confirm, for example, that the prerequisites were properly performed. A list or thumbnails of prerequisites may be output to a display device for viewing. By selecting one or more of the prerequisites, the surgical team's own work in the current procedure may be displayed in the form of video clips, enabling confirmation that all is in order for the upcoming event. Additionally or alternatively, the system might select a group of clips to be shown sequentially as a composite, demonstrating a group of prerequisites. Regardless of format, as each video clip of the ongoing surgical video is played, the surgeon may be able to verify through comparison to the list that each prerequisite has been completed. Verification is not limited to manual review by a medical professional and may be performed automatically through the system analyzing video frames and accessing stored data associated with the surgical video clips. In such situations, if a prerequisite was missed or improperly competed, a warning might be displayed to the surgeon. The warning might include one of more of text, audio, a selection of a video clip from a prior surgery demonstrating the missed prerequisite, and a video clip from the current surgery illustrating the improperly completed prerequisite.

The at least one prerequisite may be a plurality of prerequisites, and the operations may further comprise enabling the surgeon to select a prerequisite of the plurality of prerequisites. For example, there may be more than one prerequisite to an expected future event, and each prerequisite may need to be performed in a specific order with one required to be performed before the other. In some embodiments, selecting a prerequisite of the plurality of prerequisites causes a presentation of a portion of the surgical video feed of the ongoing surgical procedure captured before the generation of the at least one option that corresponds to the selected prerequisite. For example, the option to review may include two prerequisites, and in response to the user's selection of one of the prerequisites, a presentation of a portion of the surgical video feed associated with the one prerequisite may be displayed, with portions of the surgical video feed associated with the other prerequisites are omitted.

In some embodiments, the system may cause a presentation of an indication of a prerequisite in conjunction with the intra-surgical presentation. An indication of a prerequisite may be any textual, audible, or graphical label identifying the video clips associated with the intra-surgical presentation as a prerequisite to an expected future event. An indication may be a label of text or numbers on a display interface on which intra-surgical video is presented, or the indication may be presented on a separate display. Moreover, the indication may be an audible signal containing words or non-word communications, or any other signal appropriate for identifying a video clip as a prerequisite. In embodiments with multiple prerequisites, the presentation of an indication of a prerequisite may be displayed in conjunction with the intra-surgical presentation associated with that prerequisite. For example, considering a future expected event with two prerequisites, the system may cause a presentation of an indication of the first prerequisite in conjunction with the intra-surgical presentation of the first part of the selected portions; and causing a presentation of an indication of the second prerequisite in conjunction with the intra-surgical presentation of the second part of the selected portions.

Aspects of this disclosure may include receiving a signal indicative of an entering of a surgeon to the ongoing surgical procedure. The signal may be generated by a surgical operation room management system, from user input, from an analysis of audio captured from a surgical operation room corresponding to the ongoing surgical procedure, using speech recognition algorithms capable of identifying a call to the surgeon or identifying the surgeon's voice, from an analysis of images captured from a surgical operation room corresponding to the ongoing surgical procedure, through visual recognition algorithms (such as face recognition, person recognition, object recognition, etc.), or from personnel tracking systems. The signal is not limited to the specific moment when the surgeon enters the ongoing surgical procedure, but may be generated in anticipation of a surgeon entering the ongoing surgical procedure determined by an operation room management system or personal location device, or it may be generated after the surgeon has entered the ongoing surgical procedure.

In some embodiments, the system outputs for intra-surgical presentation at least part of the surgical video feed of the ongoing surgical procedure in response to the signal indicative of an entering of a surgeon to the ongoing surgical procedure. For example, a surgeon may enter the operating room and wish to review a summary of intraoperative events performed in the surgery thus far. After receiving a signal indicating a new surgeon has entered the operating room, the system may output one or more surgical video clips depicting intraoperative events in a sequential order while omitting the portions of the video not related to intraoperative events. The clips may be keyed to an index for individual selection. In some examples, the part of the surgical video feed may be a visual summary of the ongoing surgical procedure before the entering of the surgeon. For example, the system may identify each intraoperative event performed before the entering of the surgeon and may then display a composite of video clips showing the intraoperative events in succession while omitting video frames not associated with an intraoperative event. In this way, the entering surgeon may view a series of video clips that depict only a subset of intraoperative events, allowing the surgeon to understand the surgical history in a quick period of time. In embodiments consistent with the present disclosure, the surgeon may enter the operating room for a specific purpose, such as to respond to a patient complication. In this embodiment, the system may present for display a surgical video clip depicting intraoperative events that correspond to the complication, such as an abrasion or cutting of an internal organ or blood vessel.

In some aspects, the system may receive an indication of a user desire to review past occurrences of the ongoing surgical procedure. A user may input an indication of a user desire to review past occurrences through a user interface of a user device, such as a desktop computer, a laptop, a table, a mobile phone, a wearable device, an internet of things (IoT) device, dedicated hardware, or any other means for receiving input from a user. The indication by the user may be performed at any time during the surgical procedure and may be used to facilitate a review of intraoperative events performed during the surgical procedure. In response to the user indication, at least part of the surgical video feed of the ongoing surgical procedure may be output for intra-surgical presentation. The part of the surgical video feed of the ongoing surgical procedure may correspond to the user's selection. For example, the user may select and receive a presentation of a summary of intraoperative events, a visual summary of the ongoing surgical procedure, a visual summary of the ongoing surgical procedure before the entering of the user, a subset of intraoperative events such as those corresponding to a complication, or a subset of intraoperative events corresponding to one or more prerequisites associated with the user selection.

In some embodiments, the at least one future expected event may be a complication such as the type described herein, and outputting the at least one video clip may include presenting at least on complication-avoiding video clip demonstrating a surgical technique to avoid the complication. The complication-avoiding video clip may include alternative or remedial surgical techniques or other intraoperative events that can mitigate or prevent the complication. Such clips may be drawing from prior surgical footage using artificial intelligence as described earlier. In some embodiments, the at least one complication-avoiding video clip may include a plurality of complication-avoiding video clips demonstrating alternative surgical techniques to avoid the complication. For example, if an internal bleeding is predicted, complication-avoidance video clips may be presented such as videos depicting surgical bracing, stitching or suturing, alternative surgical paths avoiding the area of the predicted complication, or other suitable videos depicting complication-avoidance surgical techniques.

In some examples, wherein the at least one future expected event may be a complication, the at least one surgical video clip includes at least one misstep clip demonstrating at least one action giving rise to the complication. A misstep clip may be a group of video frames depicting the action or intraoperative event that causes or may be most likely to cause the complication. In an example, a future complication may be a fluid leak and the misstep clip may depict an abrasion or cutting of an organ or tissue that caused or may be likely to cause the complication. Other examples of misstep clips include accidental contact with organs or tissue by a surgical instrument, omission of a prerequisite in a surgical procedure, a deviation from operating in a surgical plane, or any other actions that give rise to surgical complications. As is the case with all video clip selections presented for playback consistent with this disclosure, the misstep clips may be selected by the system using artificial intelligence, as described earlier.

Some aspects of the disclosure may involve operations may include triggering an intra-surgical warning of a risk in an upcoming portion of the ongoing surgical procedure. The warning may be triggered using artificial intelligence by predicting a future event in the ongoing surgical procedure that may be associated with increased probabilities of patient complications. An intra-surgical warning may be an audible signal such as an alarm, siren, tone, simulated speech, or the like, or it may be a visual signal such as a warning light, a pop-up message on a display, a flashing light or screen, or any other visual indicator. The intra-surgical warning may also include haptic feedback such as a buzz or vibration emitted from surgical equipment, gloves, or another wearable device on the surgeon's body. The system may further display a message describing the risk. The message may appear on a display device or screen of the type described herein. In a further embodiment, an intra-surgical picklist of risk-reducing video clips may be presented for review. The picklist may be displayed on a display device adjacent to the message describing the risk. The picklist may include complication-avoiding video clips intended to alert the surgeon to risk-mitigation techniques available to reduce risk of complication during a portion of the surgical procedure.

Figure 16:
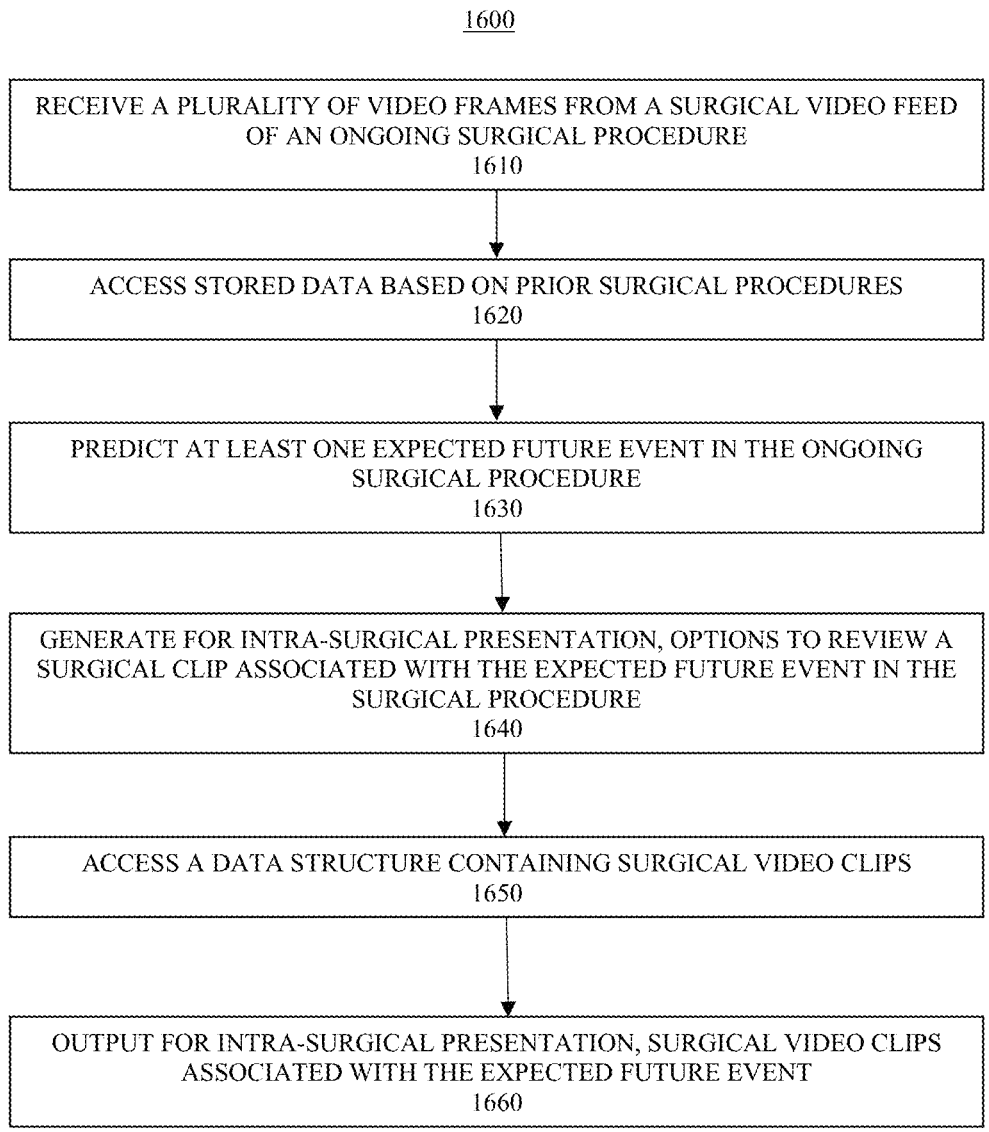
FIG. 16 is a flowchart illustrating an exemplary process for providing intraoperative video review for an ongoing surgical procedure, consistent with disclosed embodiments.

FIG. 16 is a flowchart illustrating an example process 1600 for providing intraoperative video review of surgical procedures. Process 1600 may be performed by one or more processors that implement artificial intelligence functionality. In some embodiments, a non-transitory computer readable medium may contain instructions that when executed by a processor cause the processor to perform process 1600. Process 1600 is not necessarily limited to the steps shown in FIG. 16 and any steps or processes of the various embodiments described throughout the present disclosure may be included in process 1600. At step 1610, process 1600 may include receiving a plurality of video frames from a surgical video feed of an ongoing surgical procedure. A surgical video feed may refer to any video, group of video frames, or video footage including representations of a surgical procedure currently in progress.

At step 1620, process 1600 may include accessing stored data based on prior surgical procedures. Stored data may include any data derived directly or indirectly from images of previous surgical procedures. At step 1630, process 1600 may include predicting at least one expected future event in the ongoing surgical procedure. Predicting an expected future event may be performed through use of the disclosed computer visual analysis and artificial intelligence techniques to identify an intraoperative event in the ongoing surgical procedure and referencing stored data representing relationships between intraoperative events and predicted outcomes.

At step 1640, process 1600 may include generating for intra-surgical presentation, options to review a surgical clip associated with the expected future event in the surgical procedure. As described herein, options to review surgical clips may be generated in association with the expected future event and may be displayed on a screen or other display device.

At step 1650, process 1600 may include accessing a data structure containing surgical video clips. Accessing a data structure may include receiving surgical video clips through an electronic transmission, retrieving the surgical video clips from storage (e.g., a memory device), or any other process for accessing data. At step 1660, process 1600 may include outputting for intra-surgical presentation, surgical video clips associated with the expected future event. As described herein, outputting the surgical video clips may include presenting the surgical video clips on a screen or other display device, storing the surgical video clips in a location accessible to another computing device, transmitting the surgical video clips, or any other process or method that may cause or enable the surgical video clips to be viewed.

Aspects of present disclosure relate to systems and methods for analyzing surgical procedures and assessing surgical competency of a subject. Disclosed systems and methods may involve using various techniques to analyze video frames associated with a surgical procedure to determine a competency level of a subject in the video frames.

In surgical procedures, it is important that the surgeon is competent. Thus, evaluation of the performance of health care providers (such as interns, residents, attendings, etc.) in surgeries is an import part in training of physicians and in the management of health care organizations. However, manual evaluation may be time consuming and inaccurate. Additionally, after a surgeon enters practice, the oversight of the surgeon may be limited. However, it may be essential for the health of patients that surgeons are routinely reviewed for competency. Further, complex surgeries may require several hours for a skilled surgeon to perform. Manual review of surgeons, either in person, or by manual video review is inefficient and time consuming. For example, having a surgeon of at least the same experience level routinely monitor other surgeons during lengthy procedures may significantly reduce efficiency in the medical system and decrease the number of patients that a particular hospital can serve. Additionally, review of others involved in a surgery (nurses, assistants, other doctors, etc.) may be important for optimal patient care. For example, while a surgeon is performing a complex surgery, the surgeon may be unable to closely oversee the medical professionals providing assistance in the operating room. Therefore, there is a need for unconventional approaches for automated analysis of surgical procedures to assess surgical competency of subjects involved in the procedures.

Aspects of this disclosure may include systems, methods, and computer readable media for automated video or audio analysis of surgical procedures used to assess the performance of medical professional involved in surgical procedures. For example, disclosed embodiments may include a non-transitory computer readable medium for analyzing surgical procedures and assessing surgical competency of subjects. Disclosed embodiments may use video of surgical procedures to assess various aspects of a subject's performance, such as tissue handling, economy of motion, depth perception and surgical procedure flow. The nature of the disclosed embodiments enables, for example, the creation of scores that may indicate a relative competency or skill level of a subject. The results of a competency assessment may be presented in an interface that permits user view of the associated scores, as well as links to video clips related to the scores. Accordingly, the disclosed embodiments provide solutions for automated assessment of surgical competency and presenting surgical video clips associated with the assessment thereby enabling object, accurate, and efficient review of persons performing or otherwise involved with surgical procedures.

For ease of discussion, a method is described below, with the understanding that aspects of the method apply equally to systems, devices, and computer-readable media. For example, some aspects of such a method may occur electronically over a network that is wired, wireless, or both. Other aspects of such a method may occur using non-electronic means. In a broadest sense, the method is not limited to particular physical and/or electronic instrumentalities, but rather may be accomplished using many differing instrumentalities.

Disclosed embodiments may involve receiving a plurality of video frames associated with at least one surgical procedure. A plurality of video frames may refer to a grouping of frames from one or more surgical videos or surgical video clips. The video frames may be stored in a common location or may be stored in a plurality of differing storage locations. Receiving video frames may be performed via a communication from a computer system through a network. For example, receiving the stored data may include receiving the video frames through an electronic transmission, retrieving the video frames from storage (e.g., a memory device), or any other suitable process for receiving or accessing stored data. In one example, the received plurality of video frames may include video frames captured from a captured from within a surgical cavity using at least one image sensor positioned within the surgical cavity.

Although not necessarily so, video frames within a received group may be related in some way. For example, video frames within a set may include frames, recorded by the same capture device, recorded at the same facility, recorded at the same time or within the same timeframe, depicting surgical procedures performed on the same patient or group of patients, depicting the same or similar surgical procedures, or sharing any other properties or characteristics.

In some embodiments, the plurality of video frames may be associated with a surgical procedure. For example, the video frames may be from a surgical video feed. A surgical video feed may refer to any video, group of video frames, or video footage including representations of an ongoing surgical procedure. For example, the surgical video may include one or more video frames captured during a surgical operation. A surgical procedure may include any set of medical actions associated with or involving manual or operative activity on a patient's body. While a patient as used herein generally refers to a human patient undergoing surgery, disclosed embodiments may be implemented for surgical operations performed on animals (e.g., dogs, cats, pigs, or other mammals; birds; reptiles; amphibians; and other non-human patients). Surgical procedures may include one or more of surgeries, repairs, ablations, replacements, implantations, implantations, extractions, treatments, restrictions, re-routing, and blockage removal. Such procedures may involve cutting, abrading, suturing, extracting, lancing or any other technique that involves physically changing body tissues and/or organs. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a discectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally invasive surgery for intracerebral hemorrhage evacuation, or any other medical procedure involving some form of incision. While the present disclosure is described in reference to surgical procedures, it is to be understood that it may also apply to other forms of medical procedures, or procedures generally.

Disclosed embodiments may involve accessing stored data based on prior surgical procedures. Stored data may refer to data of any format that was recorded and/or stored previously. In some embodiments, the stored data may be one or more video files including historical surgical footage or historical data. For example, the stored data may include a series of frames captured during the prior surgical procedures. This stored data is not limited to video files, however. For example, the stored data may include information stored as text representing at least one aspect of the stored surgical footage. For example, the stored data may include a database of information summarizing or otherwise referring to historical surgical footage. In another example, the stored data may include information stored as numerical values representing at least one aspect of the historical surgical footage. In an additional example, the stored data may include statistical information and/or statistical model based on an analysis of the historical surgical footage. In yet another example, the stored data may include a machine learning model trained using training examples, and the training examples may be based on the historical surgical footage. Accessing the stored data may include receiving the stored data through an electronic transmission, retrieving the historical data from storage (e.g., a memory device), or any other process for accessing data. Additionally or alternatively, accessing the stored data may include generating the stored data, for example by analyzing previously recorded surgical procedures or by analyzing data based on the stored surgical footage of prior surgical procedures. The stored data may be in a data structure consistent with disclosed embodiments, such as in FIG. 5 or FIG. 6.

The stored data may be based on prior surgical procedures. Stored data may include any data derived directly or indirectly from images of previous surgical procedures. This data may include, for example, patient characteristics, surgeon characteristics (e.g., a skill level), and/or surgical procedure characteristics (e.g., an identifier of a surgical procedure, an expected duration of a surgical procedure). Stored data may include correlations or other data describing statistical relationships between historical intraoperative surgical events and historical outcomes. In some embodiments, a data structure may include data relating to recommended actions, alternative courses of action, and/or other actions that may change a probability, likelihood, or confidence of a surgical outcome. For example, a data structure may include information correlating a break from a surgical procedure with an improved outcome. Depending on implementation, a data structure may include information correlating a skill level of a surgeon, a request for assistance from another surgeon, and outcomes. Similarly, a data structure may store relationships between surgical events, actions (e.g., remedial actions), and outcomes. While a host of correlation models may be used for prediction as discussed throughout this disclosure, exemplary predictive models may include a statistical model fit to historical image-related data (e.g., information relating to remedial actions) and outcomes; and a machine learning models trained to predict outcomes based on image-related data using training data based on historical examples.

Stored data based on prior surgical procedures may include data indicating previous performance assessments of subjects involved in the surgical procedure. As used herein, a subject may refer to a medical professional or other person involved in a surgical procedure. For example, subjects may include surgeons, nurses, anesthesiologists, interns, residents, attending physicians, physician's assistant, technicians, or others assisting with or involved in a surgical procedure. In some embodiments, a subject may be a surgical robot. Data indicating previous performance assessments may include prior competency-related scores, assessments, evaluations, or other existing data related to the performance of a subject during a previous surgical procedure.

Accessing stored data may include accessing stored historical data identifying intraoperative events, associated outcomes, or a recommended sequence of events. As used herein, an intraoperative event for the surgical procedure (also referred to as a surgical event) may refer to an action that is performed as part of a surgical procedure, such as an action performed by a surgeon, a surgical technician, a nurse, a physician's assistant, an anesthesiologist, a doctor, any other healthcare professional, a surgical robot, and so forth. The intraoperative surgical event may be a planned event, such as an incision, administration of a drug, usage of a surgical instrument, an excision, a resection, a ligation, a graft, suturing, stitching, or any other planned event associated with a surgical procedure or phase. Additionally, or alternatively, an intraoperative event may also refer to an event occurring to an anatomical structure and/or to a medical instrument related to the surgical procedure, regardless of whether the event includes an action performed by a healthcare professional. One example of such an intraoperative event may include a change in a condition of an anatomical structure.

As described herein, a recommended sequence of events may include a series of events that should occur in a particular order or within a given time frame. In some embodiments, certain events may be conditional based on patients' conditions, previous events, etc. Further, comparing the accessed video frames with the recommended sequence of events may include comparing a sequence of the identified events within the video frames with the recommended sequence of events for the surgical procedure. Comparing a sequence of events may occur, for example, as described herein with reference to FIG. 11.

An exemplary surgical intraoperative event for a laparoscopic cholecystectomy surgery may include trocar placement, calot's triangle dissection, clipping and cutting of cystic duct and artery, gallbladder dissection, gallbladder packaging, cleaning and coagulation of liver bed, gallbladder retraction, and so forth. In another example, surgical events of a cataract surgery may include povidone-iodine injection, corneal incision, capsulorhexis, phaco-emulsification, cortical aspiration, intraocular lens implantation, intraocular-lens adjustment, wound sealing, and so forth. In yet another example, surgical characteristic events of a pituitary surgery may include preparation, nasal incision, nose retractor installation, access to the tumor, tumor removal, column of nose replacement, suturing, nose compress installation, and so forth. Some other examples of surgical characteristic events may include incisions, laparoscope positioning, suturing, and so forth.

In some embodiments, the surgical intraoperative event may include an adverse event or a complication. Some examples of adverse surgical events may include bleeding, mesenteric emphysema, injury, conversion to unplanned open surgery (for example, abdominal wall incision), incision significantly larger than planned, and so forth. Some examples of intraoperative complications may include hypertension, hypotension, bradycardia, hypoxemia, adhesions, hernias, atypical anatomy, dural tears, periorator injury, arterial occlusions, and so forth. In some cases, surgical events may include other errors, including technical errors, communication errors, management errors, judgment errors, decision-making errors, errors related to medical equipment utilization, miscommunication, and so forth. In various embodiments, events may be short or may last for a duration of time. For example, a short event (e.g., incision) may be determined to occur at a particular time during the surgical procedure, and an extended event (e.g., bleeding) may be determined to occur over a time span. In some cases, extended events may include a well-defined beginning event and a well-defined ending event (e.g., beginning of suturing and ending of the suturing), with suturing being an extended event. In some cases, extended events are also referred to as phases during a surgical procedure.

In some cases, a surgical event may identify a group of sub-events (i.e., more than one sub-event or steps). For example, an event of administering general anesthesia to a patient may include several steps such as a first step of providing a medication to a patient via an IV line to induce unconsciousness, and a second step of administering a suitable gas (e.g., isoflurane or desflurane) to maintain the general anesthesia.

In some embodiments, the stored data based on prior surgical procedures may include a machine learning model trained using a data set based on prior surgical procedures. For example, a machine learning model may be trained to process video frames and generate competency-related scores, as described below. In one example, the machine learning model may be trained using a training dataset including video clips of previous surgeries (or portions thereof, such as individual frames, segments of individual frames, etc.) and corresponding labels including manual evaluations of subjects involved in the surgeries. In another example, the machine learning model may be trained using a training dataset including information based on an analysis of video clips of previous surgeries (such as functions of the video clips, convolutions of the video clips, etc.) and corresponding labels including manual evaluations of subjects involved in the surgeries.

Disclosed embodiments may involve processing, for example using the stored data, the plurality of video frames to assess at least one of tissue handling, economy of motion, depth perception and surgical procedure flow in the plurality of video frames. As described herein, processing the plurality of frames may include using a machine learning or image analysis technique. In some embodiments, artificial intelligence algorithms (such as trained machine learning algorithms) may be used to analyze inputs and generate outputs, for example in the cases described herein. Processing the plurality of video frames may include analyzing image data of the video frames. As described herein, analyzing image data (as described herein) may include analyzing the image data (in this case, data related to a video frame) to obtain preprocessed image data, and subsequently analyzing the image data and/or the preprocessed image data to obtain the desired outcome. Aspects of disclosed embodiments may include processing the received plurality of video frames and, based on information obtained from stored data, to assess tissue handling, economy of motion, depth perception, or surgical procedure flow. As previously described, and consistent with various embodiments, a process of analyzing the received video frames may be performed by a suitable machine-learning model such as an image recognition algorithm, as described above, consistent with disclosed embodiments. In various embodiments, information obtained from stored historical data based on prior surgical procedures may be used to train the image recognition algorithm to assess aspects of surgical procedures by recognizing and comparing specific intraoperative events, actions, timings, etc. base on accessed frames of surgical footage, as previously described. In one example, the historical data may include a statistical model and/or a machine learning model based on an analysis of information and/or video footage from historical surgical procedures (for example as described above), and the statistical model and/or the machine learning model may be used to analyze the accessed frames and identify deviations in the received video frames from a reference set of frames or images related to prior surgical procedures. Such automated processing and assessment techniques may provide more accurate, efficient, and objective measures of surgical competency of subjects, compared to manual assessment. For example, automated assessments may remove biases of human reviewers while also being conducted more quickly without requiring a human reviewer to watch and analyze video of a surgical procedure that could last several hours.

As an example of processing using a machine learning model, a machine learning model may take one or more video frames or preprocessed image data from the video frames as input and output information related to the video frames, such as differences between the frames and reference frames. The model may compare the received frames to expected surgical events from the stored data based on prior procedures. For example, the machine learning model may recognize a type of surgical procedure based on the processed image data, and then compare the image data to an expected list of events, timing, actions by the subject, etc. Based on the comparison, deviations between the expected actions and the actual actions taken by the subject during the surgical procedure may be assessed. For example, specific deviations may be identified, or a level of deviation for certain specific events or event characteristics may be determined. As another example, the actual timing or length of events may be compared with expected times based on the type of surgical procedure or event. In various embodiments, such an event-based machine learning method may be trained using training examples, for example as described above. For example, a training example may be based on historical data related to previous surgical procedures.

According to disclosed embodiments, a subject's tissue handling may be assessed. As used herein, tissue handling may refer to a subject's performance of various surgical tasks. For example, an assessment of tissue handling may include assessment of a subject's adherence to rules or guidelines associated with handling tissues, size or placement of incisions, suture technique (e.g., width between stitches, placement, etc.), placement of tension, other surgical techniques such as gentleness of handling tissues, sanitation techniques, or other factors related to a subject's treatment of anatomical tissue. Tissue handling assessment may also include a determination of whether the subject made any surgical errors in tissue handling, such as rough movements, tearing tissues, injury to adjacent structures, excessive tension or force applied to the tissues, or failure to follow best surgical practices. Tissue handling of a subject may be identified through actions taken by the subject during specific surgical events identified in the received video frames. The actions may be compared to reference or recommended actions accessed, for example, in accessed stored data based on prior surgical procedures. For example, the reference actions may indicate a reference size for the degree of tension placed on the tissue. The subject's actions identified from the received video frames (e.g., an incision length) may be compared to reference incision size. As an example, if there is no injury to adjacent structures, or no unnecessary bleeding, or appropriate traction applied, the subject may be assigned a relatively high competency-related score, as described in greater detail below. By contrast, if there is unnecessary bleeding or unnecessary tearing of tissues, the subject may be assigned a relatively lower competency-related score, as described in greater detail below. The tissue handling may be assessed using artificial intelligence trained on image data. For example, a machine learning model may be trained using training examples to assess tissue handling from surgical footage, and the trained machine learning model may be used to analyze the plurality of video frames and generate the assessment of the subject's tissue handling. An example of such training example may include surgical footage from a particular prior surgical procedure, together with a label indicating a desired assessment for the tissue handling in the particular prior surgical procedure.

In some embodiments, a subject's economy of motion may be assessed. As used herein, economy of motion may refer to an efficiency of the subject's movements or an indication of the subject's dexterity during a surgical procedure. Various actions taken by the subject may be identified from the received video frames and used to assess the subject's economy of motion. As an example, an action may include optimizing the field of view and exposure of tissues. Lack of exposure may impair a surgeon's ability to visualize and perform surgery optimally. If the subject takes a relatively long time to expose the field of view, the subject may receive a relatively lower economy of motion assessment. If the subject uses only one hand, without coordination with the less dominant hand, subject may receive a relatively lower economy of motion assessment. Such an economy of motion assessment may be made by comparing actions of the subject to reference action data, for example, included in the accessed stored data based on prior surgical procedures. Such reference data may include various data related to efficiency of the subject motion or dexterity, such as but not limited to, length of time to perform a given action, the relative amount of movement performed by the subject when taking a certain action, a number of movements needed to perform an action, a speed of movements of the subject, an indication of movements considered to be normal for a given action, an indication of movement considered to be anomalous for a given action, a number of movements over the course of a surgical procedure, or other factors indicating an efficiency of movement of the subject or the subject's level of dexterity. Such factors may be compared to corresponding thresholds, which may indicate if the subject makes excess movements during the procedure. Excess movements or inefficiency of movements may reduce the subject's competency-related score, as described in greater detail below. Economy of motion may be assessed using artificial intelligence trained on image data. For example, a machine learning model may be trained using training examples to assess economy of motion from surgical footage, and the trained machine learning model may be used to analyze the plurality of video frames and generate the assessment of the subject's economy of motion. An example of such training example may include surgical footage from a particular prior surgical procedure, together with a label indicating a desired assessment for the economy of motion in the particular prior surgical procedure.

Disclosed embodiments may include assessing the depth perception of the subject. Depth perception may refer to the ability of the subject to judge the distance or locations of objects in three dimensions. For example, depth perception in surgery may be important for making accurate incisions of a certain depth. Incisions that are too deep may unnecessarily damage tissue that should not be damaged during a surgical operation. However, incisions of insufficient depth may require additional cuts, thus decreasing the efficiency of the operation and potentially increasing the time required to complete the operation, as well as placing additional stress on the patient. As an example, of depth perception assessment, an estimated incision depth may be determined from the received video frames. This incision depth may be compared to a recommended incision depth for the incision based on the surgical procedure. The recommended depth may be included in, for example, the accessed stored data based on prior surgical procedures. The estimated depth based on the received video frames may be compared to a threshold depth based on the recommended depth. If the estimated depth is within the threshold depth, the subject may be assigned a relatively high competency-related score, as described in greater detail below. By contrast, if the estimated depth is not within the threshold depth (i.e., the incision is too deep or too shallow), the subject may be assigned a relatively lower competency-related score, as described in greater detail below. Depth perception may be assessed using artificial intelligence trained on image data. For example, a machine learning model may be trained using training examples to assess depth perception from surgical footage, and the trained machine learning model may be used to analyze the plurality of video frames and generate the assessment of the subject's depth perception. An example of such training example may include surgical footage from a particular prior surgical procedure, together with a label indicating a desired assessment for the depth perception in the particular prior surgical procedure. In some examples, the assessment of the subject's depth perception may be based on indication of the efficiency of subject's depth perception, such as but not limited to, overshooting a given action, time to correct a faulty movement, the number of times a subject misses a target, and so forth.

Consistent with disclosed embodiments, a subject's surgical procedure flow may be assessed. Surgical procedure flow may refer to the sequence or timing of intraoperative steps or actions taken by the subject during a surgical procedure. Surgical procedure flow may be assessed by identifying a surgical procedure flow of the surgical procedure based on the received video frames and comparing to the identified surgical procedure flow to an expected flow. For example, using techniques described herein, a series of intraoperative steps may be identified from the received video frames. Additionally, timings associated with the steps may be determined based on the video frames using disclosed techniques. A type of the surgical procedure may also be identified. As described herein, different types of surgical procedures may have preferred or required orders of steps and step timings. Accordingly, the identified intraoperative steps and timings may be compared against a recommended sequence of steps based on an identified type of the surgical procedure. For example, a recommended sequence of steps of a cataract surgery may include povidone-iodine injection, corneal incision, capsulorhexis, phaco-emulsification, cortical aspiration, intraocular lens implantation, intraocular-lens adjustment, wound sealing, and so forth. If video frames of a subject performing such a cataract surgery show an order of steps including povidone-iodine injection, a first corneal incision, a first wound sealing, a second corneal incision, capsulorhexis, phaco-emulsification, cortical aspiration, intraocular lens implantation, and a second wound sealing, significant deviations between such a sequence of steps and the recommended sequence of steps. The determined deviations between the actual sequence of steps from the received video frames and the recommended sequence of steps may influence a competency-related score for the subject, as described in greater detail below. For example, such significant deviations (e.g., here including steps performed out of order or unnecessary repetition of steps) may indicate a relatively lower competency level of the subject performing the actions.

Surgical flow may also involve recognition of adverse events or complications. The presence or absence of certain events or complications may also affect a subject's competency assessment and corresponding scores. For example, significant bleeding may indicate a relatively lower competency level of the subject, and accordingly, a lower competency-related score. Surgical flow may be assessed using artificial intelligence trained on image data. For example, a machine learning model may be trained using training examples to assess surgical procedure flow from surgical footage, and the trained machine learning model may be used to analyze the plurality of video frames and generate the assessment of the subject's surgical procedure flow. An example of such training example may include surgical footage from a particular prior surgical procedure, together with a label indicating a desired assessment for the surgical procedure flow in the particular prior surgical procedure.

Disclosed embodiments may involve calculating at least one convolution of at least part of at least one of the plurality of video frames. Such a convolution may include a mathematical operation which provides a way of multiplying together two arrays of numbers, generally of different sizes to produce a third array of numbers. For example, in the case the two arrays of numbers are of the same dimensionality, the third array of numbers would be of the same dimensionality. As described herein, a convolution may be used as part of an image analysis to analyze the data. The accessed stored data may be used to analyze the calculated at least one convolution. For example, the stored data may be compared to the calculated convolution to look for deviations from reference actions or other indications of the subject's surgical performance. Accordingly, the method may include using the analysis of the calculated at least one convolution to assess the at least one of tissue handling, economy of motion, depth perception and surgical procedure flow in the plurality of video frames.

Some disclosed embodiments may involve determining at least in part from the plurality of video frames an identity of the subject. An identity of the subject may include the subject's name, title, identification name or number, profile, or other information used to identify the subject. The subject's identity may be determined based on at least one of a user input, an associated medical record, facial recognition, voice recognition, or an output of a personnel tracking system. For example, a medical record associated with the patient may indicate the name of the surgeon performing the surgery. As another example, personnel within a hospital or other medical setting may have keycards or personal trackers that could be part of personnel tracking system. Accordingly, the subject's identity may be determined based on, for example, the subject's location within the surgical room.

Disclosed embodiments may involve receiving audio signals associated with the surgical procedure and to determine a level of subject autonomy based at least in part on the audio signals. For example, the audio signals may include verbal communications between various members of a surgical team in a surgical room. The number or nature of the communications may indicate a level of autonomy of the surgeon. As an example, a surgeon asking multiple questions to team members throughout the surgical procedure may indicate that the surgeon is less experienced and less autonomous than a surgeon who asks no questions during a procedure. By way of another example, a supervising surgeon providing regular or otherwise significant verbal direction to an operating surgeon may be an indicator that the operating surgeon has a lower level of autonomy. The system may assess the substance of the verbal interactions to differentiate between non-directional exchanges and directional instructions or guidance.

Disclosed embodiments may involve, based on the assessment of at least one of tissue handling, economy of motion, depth perception and surgical procedure flow, generating a competency-related score for a subject. A competency-related score may take the form of a numerical score on a defined scale (e.g., a scale of 1-10 or 0-25), a percentage, a relative level (e.g., a low, medium, or high competency level), or other comparative score or level. A competency-related score may indicate a level of competency or skill of a subject. A highly skilled surgeon may have a relatively high competency-related score. By contrast, a new surgical resident with less training may have a relatively low competency-related score. The competency-related score may be generated based on the assessment of at least one of tissue handling, economy of motion, depth perception or surgical procedure flow.

Consistent with disclosed embodiments, a competency score may be based on a subject's economy of motion assessment. As an example, a subject may take actions during the course of a surgical procedure which may be analyzed by, for example, a machine learning algorithm. The algorithm may identify the actions associated with the surgeon's economy of motion and assign a competency-related score based on the analysis of the identified actions. For example, the actions may include the creation of an incision. The time it takes for the subject to make the incision may influence the subject's economy of motion score. If the subject takes a relatively long time to make a short incision, the subject may receive a relatively lower economy of motion assessment. Such an economy of motion assessment may be made by comparing actions of the subject to reference action data, for example, included in the accessed stored data based on prior surgical procedures. Assessments and competency-related scores may be based on reference data, for example, a group of actions by an average or reference-level surgeon. As described above, such reference data may include various data related to efficiency of the subject motion or dexterity, such as but not limited to, length of time to perform a given action, the relative amount of movement performed by the subject when taking a certain action, a number of movements needed to perform an action, a speed of movements of the subject, an indication of movements considered to be normal for a given action, an indication of movement considered to be anomalous for a given action, a number of movements over the course of a surgical procedure, or other factors indicating an efficiency of movement of the subject or the subject's level of dexterity. Such factors may be compared to corresponding thresholds, which may indicate if the subject makes excess movements during the procedure. For example, if a surgeon exceeds a threshold level of movements while performing a certain action, the surgeon's competency-related score may be reduced.

Disclosed embodiments may include basing a competency score on the depth perception assessment of the subject. As an example, during a surgical procedure, a subject may make an incision. A machine learning model may recognize the making of the incision from the received video frames and estimate an incision depth. This incision depth may be compared to a recommended incision depth for the incision based on the type of particular surgical procedure being performed. The recommended depth may be included in, for example, the accessed stored data based on prior surgical procedures. The estimated depth based on the received video frames may be compared to a threshold depth based on the recommended depth. If the estimated depth is within the threshold depth, the subject may be assigned a relatively high competency-related score (e.g., a 5 out of 5 depending on the amount of difference from the recommended depth). By contrast, if the estimated depth is not within the threshold depth (i.e., the incision is too deep or too shallow), the subject may be assigned a relatively lower competency-related score (e.g., a 2 out of 5 depending on the degree of difference from the recommended depth).

Consistent with disclosed embodiments, a subject's competency-related score may be based on the subject's surgical procedure flow assessment. Surgical procedure flow may refer to the sequence or timing of intraoperative events or actions taken by the subject during a surgical procedure. Surgical procedure flow may be assessed by identifying a surgical procedure flow of the surgical procedure based on the received video frames and comparing to the identified surgical procedure flow to an expected flow. For example, using techniques described herein, a series of intraoperative events may be identified from the received video frames. Additionally, timings associated with the events may be determined based on the video frames using disclosed techniques. A type of the surgical procedure may also be identified. As described herein, different types of surgical procedures may have preferred or required orders of events and event timings. Accordingly, the identified intraoperative events and timings may be compared against a recommended sequence of events based on an identified type of the surgical procedure. For example, a recommended sequence of events of a cataract surgery may include povidone-iodine injection, corneal incision, capsulorhexis, phaco-emulsification, cortical aspiration, intraocular lens implantation, intraocular-lens adjustment, wound sealing, and so forth. Video frames of a subject performing such a cataract surgery may show an order of events including povidone-iodine injection, a first corneal incision, a first wound sealing, a second corneal incision, capsulorhexis, phaco-emulsification, cortical aspiration, intraocular lens implantation, and a second wound sealing. In this example, the significant deviations between such a sequence of events and the recommended sequence of events may be recognized. Accordingly, a lower competency-related score may be assigned (e.g., a 1 out of 5). Conversely, if the subject were to perform a cataract surgery performing only the recommended steps in the recommended order and within the recommended timing, a high competency-related score may be assigned (e.g., a 5 out of 5 or 19 out of 20).

In some embodiments, a score based on surgical flow may also involve recognition of adverse events or complications. The presence or absence of certain events or complications may also affect a subject's competency assessment and corresponding scores. For example, a detected adverse bleeding event may indicate a relatively lower competency level of the subject, and accordingly, a lower competency-related score. Even if the subject were to perform only the recommended steps in the recommended order and within the recommended timing, the subject's competency score may be lowered to account for an exceedingly large incision or other adverse event.

Consistent with disclosed embodiments, a plurality of competency-related scores may be generated for a subject. Each of the plurality of scores may associated with a differing skill. The skills may include, but are not limited to, tissue handling, economy of motion, depth perception, or surgical procedure flow described above. For example, for a subject a separate competency score (e.g., out of scale of 0 to 5) may be calculated for each of the subject's tissue handling, economy of motion, depth perception, and surgical procedure flow. Thus, the subject would have four separate competency-related score, one specific to each of the four different skills.

In some embodiments, a competency-related score may include a composite score assessing a plurality of scores. A composite score may be an aggregation or combination of multiple scores related to different skills. Composite scores may be calculated through simple summation of the multiple scores, by a weighted average, or other suitable method. As an example, a subject may be assigned four separate scores, one each for tissue handling, economy of motion, depth perception, and surgical procedure flow. Each on a scale of 1 to 5, the subject may receive a tissue handling score of 4, an economy of motion score of 4, a depth perception score of 5, and surgical procedure flow score of 2. Accordingly, a composite for the subject may be 15 (4+4+5+2=15). Disclosed embodiments employing a plurality of scores on different varying aspects or skills related to a surgical procedure may permit more complete and objective assessments of subjects.

Disclosed embodiments may include selecting, from the plurality of video frames, at least one video clip from which the competency score was derived. As an example, if the competency score was based on depth perception related to an incision made during the procedure, a video clip showing creation of the incision may be selected. As another example, if a competency-score based on surgical procedure flow is generated, a clip may be selected that shows where the subject's actions first departed from the recommended surgical flow. In one example, one or more of the plurality of video frames may not be included in the at least one video clip.

In some embodiments, multiple video clips may be selected. As an example, when multiple competency-related scores are generated, a selected video clip may include a plurality of video clips. Each video clip may be associated with a differing score. Continuing the previous examples, if both the depth perception score and surgical procedure flow scores were generated for the same subject, both clips may be selected for the subject.

Disclosed embodiments may involve outputting at least one score. Outputting may involve sending code from at least one processor, wherein the code may be configured to cause the score or an interface including the score to be presented. In some embodiments, outputting may include transmitting the score to an external computing device. For example, outputting the score may include transmitting the score through a network to a user device or other external device for viewing on the external device. Consistent with disclosed embodiments, outputting may include storing the score in a location that may be accessible by one or more other computing devices. Such storage locations may include a local storage (such as a hard drive of flash memory), a network location (such as a server or database), a cloud computing platform, or any other accessible storage location. Accordingly, the score may be accessed from an external device to be displayed on the external device.

Disclosed embodiments may involve updating a personnel record of the subject with a competency score. For example, an evaluation section of the subject in a personnel record of the subject may be updated based on the at least one competency score. Similarly, the method may include causing a competency score to populate an evaluation form of the subject. An evaluation form may permit a subject to receive feedback on his or her performance in a surgical procedure. An evaluation form may be related to an evaluation of a particular surgical procedure, a series of surgical procedures, intern rotation, etc.

Disclosed embodiments may involve presenting in association with the at least one score, a link to the at least one video clip. As described herein, a link may be presented such that when the link is selected, the corresponding video clip may be presented for viewing. Consistent with disclosed embodiments, a plurality of surgical procedures may be performed and selecting a video clip may include selecting a plurality of video clips. Presenting a link to the videos may include presenting at least one video clip capture date in association with each of the plurality of video clips. Presenting the link may include causing a display of a window for playback of the at least one video clip. Accordingly, presenting the link may include causing a display of controls enabling selective playback of the at least one video clip. Presenting the link may include presenting an activatable icon in a graphical user interface. When the activatable icon is selected, the window for playback or controls enabling playback may be presented in the graphical user interface for viewing by the user.

Disclosed embodiments may involve classifying a surgical procedure type associated with the at least one video clip and presenting a control enabling a viewer to access other video clips in which the subject is presented, sharing the surgical procedure type. For example, the surgical procedure type may correspond to a specific surgical skill or intraoperative event. Video clips from other surgical procedures of the same type, depicting the same surgical skill, or intraoperative event may be presented. These video clips may permit, for example, a surgeon to easily compare her performance to clips of other surgeons performing the same or similar actions.

Figure 17:
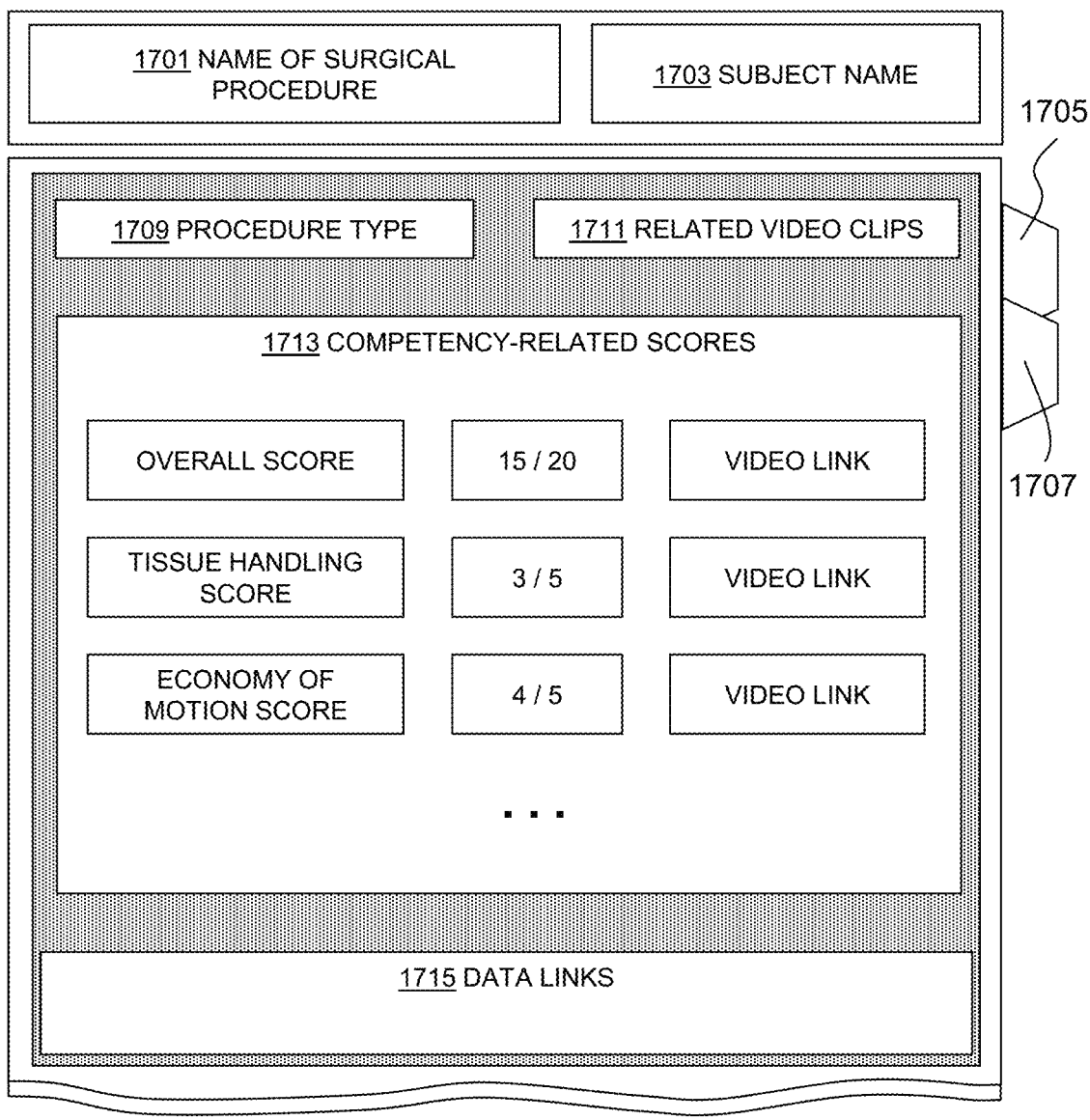
FIG. 17 is a depiction of an exemplary interface for a system for assessing surgical competency of a subject, consistent with disclosed embodiments.

By way of example, FIG. 17 illustrates an exemplary interface for a system for assessing surgical competency of a subject, consistent with disclosed embodiments. As shown in FIG. 17, interface 1700 may display a variety of information to a user. For example, interface 1700 may include a name or other indication of a surgical procedure 1701 and a name or other identifier of a subject 1703. In some embodiments, interface 1700 may indicate a procedure type 1709 (e.g., a laparoscopic surgery, an open surgery, a robotic surgery, an appendectomy, a cataract surgery, or other type of surgical procedure). Interface 1700 may also provide a link 1711 to video clips related to the procedure type 1709. Such video clips may be related to different instances of the same procedure type in which the same subject participated. Additionally, or alternatively, such video clips linked by link 1711 may be related to procedures having procedure type 1709 that were performed by other subjects. For example, such video clips may be model or reference clips showing a highly skilled surgeon properly executing the procedure or specific actions related to the procedure.

While interface 1700 is shown as relating to a single subject, it is possible for interface 1700 to convey information about more than one subject. For example, interface 1700 may provide assessment information about a surgical team. As another example, interface 1700 may provide tabs

1705, 1707. Each tab 1705, 1707 may correspond to a particular subject. In other embodiments, tabs 1705, 1707 may correspond to different surgical procedures performed by the same subject. For example, interface 1700 or another interface (not shown) may demonstrate trends in a surgeon's competency by summarizing data across a number of surgical procedures in which the surgeon was previously involved.

Interface 1700 may include an indication of competency-related scores 1713. As described herein, competency-related scores may include an overall (e.g., composite) score, as well as individual scores related to certain aspects of a procedure or surgical skills (e.g., tissue handling, economy of motion, etc.). Interface 1700 may provide an indication of the type of score, the score itself, or a link to a video related to the score. For example, interface 1700 shows an overall score of 15 out of a maximum 20 and a corresponding video link. As described above, the link may include an activatable icon. When the activatable icon is selected, a window may open for playback and controls enabling playback may be presented in the graphical user interface for viewing by the user.

Interface 1700 may also include additional data links 1715. Data links 1715 may correspond to a variety of other data related to the surgical procedure, the type of surgical procedure, the subject, actions or events within the surgical procedure, previous assessments or performance statistics of the subject, previous video clips of the subject, or other suitable information. For example, links 1715 may provide a link to a previous assessment for the subject related to a different surgical procedure of the same type. As another example, links 1715 may display graphs, charts, or other visuals indicating the subject's performance over time (e.g., a line graph showing a change in a particular competency score of the subject over multiple procedures).

Figure 18:
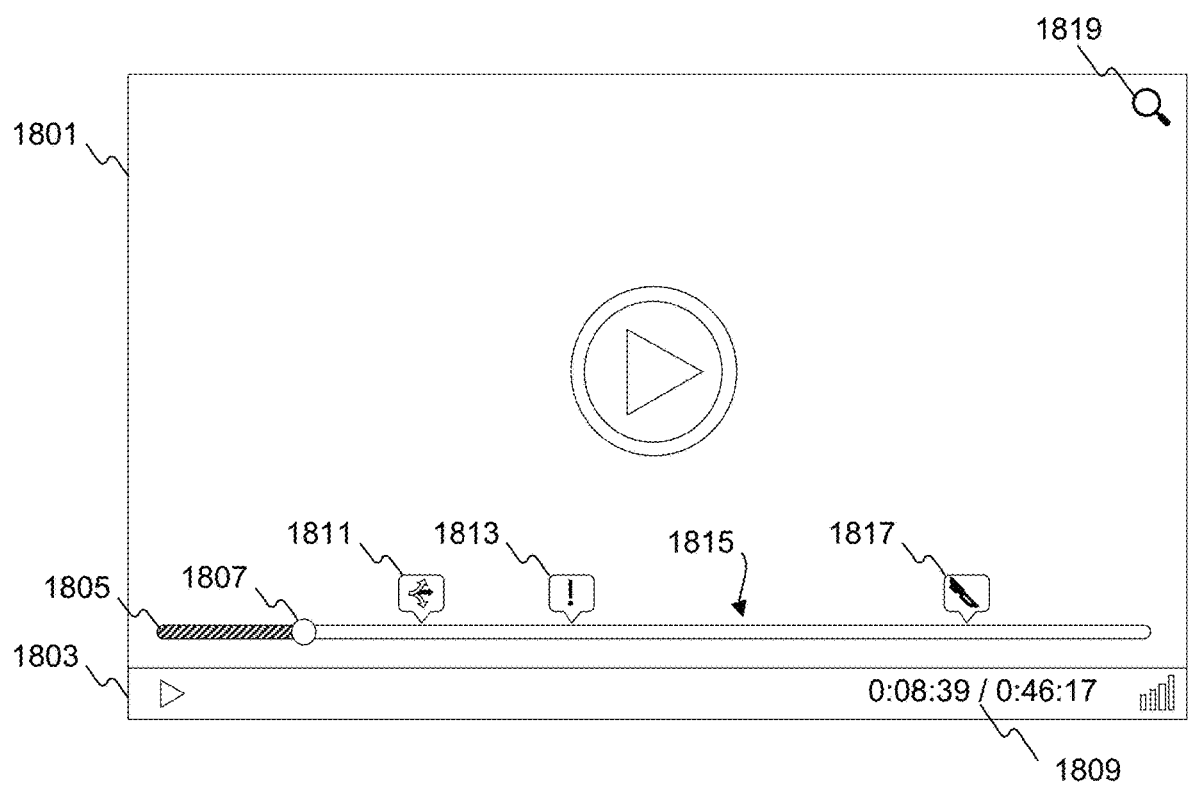
FIG. 18 is a depiction of an exemplary interface for viewing a video, consistent with disclosed embodiments.

When a user selects a video link of interface 1700, the user may be directed to a new window or interface presenting the video for viewing. This new window may include, for example, interface 1800 of FIG. 18. FIG. 18 is a depiction of an exemplary interface for viewing a video, consistent with disclosed embodiments. The interface may include an interface window 1800 for playback of the at least one video clip. Accordingly, selecting a video link from interface 1700 may cause a display of controls enabling selective playback of the at least one video clip. The video may be presented in a video playback region 1801, which may sequentially display one or more frames of the video. Interface 1800 may include a timeline 1815 displayed as a horizontal bar representing time, with the leftmost portion of the bar representing a beginning time of the video and the rightmost portion of the bar representing an end time. Timeline 1815 may include a position indicator 1807 indicating the current playback position of the video relative to the timeline. Colored region 1805 of timeline 1815 may represent the progress within timeline 1815 (e.g., corresponding to video that has already been viewed by the user, or to video coming before the currently presented frame). In some embodiments, position indicator 1807 may be interactive, such that the user can move to different positions within the video by moving position indicator 1807. In some embodiments, the surgical timeline may include markers identifying at least one of a surgical phase, an intraoperative surgical event, and a decision making junction. For example, timeline 1815 may further include one or more markers 1811, 1813, and/or 1817. Such markers may correspond to surgical events, decision points, or other points of interests, as described herein. Interface 1800 may also include a control bar 1803, with a play button and time indication 1809.

In the example shown in FIG. 18, timeline 1815 may be displayed such that it overlaps video playback region 1801, either physically, temporally, or both. In some embodiments, timeline 1815 may not be displayed at all times. As one example, timeline 1815 may automatically switch to a collapsed or hidden view while a user is viewing the video and may return to the expanded view shown in FIG. 18 when the user takes an action to interact with timeline 1815. For example, user may move a mouse pointer while viewing the video, move the mouse pointer over the collapsed timeline, move the mouse pointer to a particular region, click or tap the video playback region, or perform any other actions that may indicate an intent to interact with timeline 1815. As discussed above, timeline 1815 may be displayed in various other locations relative to video playback region 1801, including on a top portion of video playback region 1801, above or below video playback region 1801, or within control bar 1803. In some embodiments, timeline 1815 may be displayed separately from a video progress bar. For example, a separate video progress bar, including position indicator 1807 and colored region 1805, may be displayed in control bar 1803 and timeline 1815 may be a separate timeline of events associated with a surgical procedure. In such embodiments, timeline 1815 may not have the same scale or range of time as the video or the video progress bar. For example, the video progress bar may represent the time scale and range of the video, whereas timeline 1815 may represent the timeframe of the surgical procedure, which may not be the same (e.g., where the video includes a surgical summary, as discussed in detail above). In some embodiments, video playback region 1801 may include a search icon 1819, which may allow a user to search for video footage related to specific topics. The surgical timeline shown in FIG. 18 is provided by way of example only, and one skilled in the art would appreciate various other configurations that may be used.

Disclosed embodiments may involve selecting a surgical team member for a prospective surgery based on the competency-related score. As an example, surgical team may include several different surgeons. The surgeons may each have different skill sets, experience levels, or competency levels related to certain surgical actions or procedures. Accordingly, when a surgeon is needed for a particular surgery, the surgeon may be selected based on a comparison of the multiple surgeons scores related to the particular surgery. For example, the surgery may be a spinal disk replacement. Accordingly, the surgeon with the highest competency-related score for spinal disk replacement procedures may be selected. As another example, a surgery may be an operation to correct an injury very close to the patient's spinal cord. In such a case, the surgeon's depth perception may be critical to avoid damage to the spinal cord during the procedure. Accordingly, a surgeon having a high depth perception score may be selected.

Disclosed embodiments may involve providing a suggestion for additional training of the subject in response to a first competency-related score. For example, a surgeon with a low score corresponding to a particular skill may be sent a suggestion for additional training (e.g., classes, training videos, practice sessions, remedial lections, or other training or learning opportunities) related to the particular skill. Upon detection of a sub-par competency score in a certain area through, for example, the use of artificial intelligence applied to the video, the system might include programmed responses that include the training recommendations discussed above. In response to a second competency-related score, embodiments of this disclosure may forgo providing a suggestion for additional training of the subject. That is, if the competency score is not determined to be sub-par, no recommendation may be made. Determining whether to suggest additional training may be made based on a threshold score. The threshold score may indicate whether additional training should be recommended. For example, if a particular score exceeds a threshold score, additional training may not be recommended. In some embodiments, different threshold scores may be assigned to different types of scores. As an example, one threshold may be set for depth perception scores, while another threshold may be set for tissue handling scores. Yet another threshold may be set for tissue handling scores, and a fourth threshold may be set for overall or composite scores.

FIG. 19 is a flowchart illustrating an exemplary process 1900 for analyzing a surgical procedure and assessing surgical competency of a subject, consistent with disclosed embodiments. Process 1900 may be performed by a computing device or a system of computing devices. Various steps of process 1900 may be executed by a processing device, such as any of the processors described throughout the present disclosure. It is to be understood that throughout the present disclosure, the term "processor" is used as a shorthand for "at least one processor." In other words, a processor may include one or more structures that perform logic operations whether such structures are collocated, connected, or disbursed. In some embodiments, a non-transitory computer readable medium may contain instructions that when executed by a processor cause the processor to perform process 1900. Process 1900 is not necessarily limited to the steps shown in FIG. 19 and any steps or processes of the various embodiments described throughout the present disclosure may also be included in process 1900.

At step 1910, process 1900 may include receiving a plurality of video frames associated with at least one surgical procedure. Receiving video frames may be performed via a communication from a computer system through a network. For example, receiving the stored data may include receiving the video frames through an electronic transmission, retrieving the video frames from storage (e.g., a memory device), or any other suitable process for receiving or accessing stored data. Video frames within a set may include frames, recorded by the same capture device, recorded at the same facility, recorded at the same time or within the same timeframe, depicting surgical procedures performed on the same patient or group of patients, depicting the same or similar surgical procedures, or sharing any other properties or characteristics.

At step 1920, process 1900 may include accessing stored data based on prior surgical procedures. In some embodiments, the stored data may be one or more video files including historical surgical footage or historical data. For example, the stored data may include a series of frames captured during the prior surgical procedures. As described herein, this stored data is not limited to video files, however. For example, the stored data may include information stored as text representing at least one aspect of the stored surgical footage. For example, the stored data may include a database of information summarizing or otherwise referring to historical surgical footage. The stored data may be based on prior surgical procedures. Stored data may include any data derived directly or indirectly from images of previous surgical procedures. This data may include, for example, patient characteristics, surgeon characteristics (e.g., a skill level), and/or surgical procedure characteristics (e.g., an identifier of a surgical procedure, an expected duration of a surgical procedure). Stored data may include correlations or other data describing statistical relationships between historical intraoperative surgical events and historical outcomes.

At step 1930, process 1900 may include processing, for example using the stored data, the plurality of video frames to assess at least one of tissue handling, economy of motion, depth perception and surgical procedure flow in the plurality of video frames. As described herein, processing the plurality of frames may include using a machine learning or image analysis technique. In some embodiments, trained machine learning algorithms (e.g., artificial intelligence algorithms) may be used to analyze inputs and generate outputs, for example in the cases described herein.

At step 1940, process 1900 may include, based on the assessment of at least one of tissue handling, economy of motion, depth perception and surgical procedure flow, generating a competency-related score for a subject. As described herein, a competency-related score may indicate a relative competency or skill level of a subject. Scores may be generated for individual skills, actions, etc. of the subject. In some embodiments, an overall score indicating the subject's general overall competency may be generated. Composite scores including an aggregation or weighted average of individual skill scores may also be generated.

At step 1950, process 1900 may include selecting, from the plurality of video frames, at least one video clip from which the competency score was derived. As an example, if the competency score was based on depth perception related to an incision made during the procedure, a video clip showing creation of the incision may be selected. As another example, if a competency-score based on surgical procedure flow is generated, a clip may be selected that shows where the subject's actions first departed from the recommended surgical flow.

At step 1960, process 1900 may include outputting at least one score. In some embodiments, outputting may include transmitting the score to an external computing device. For example, outputting the score may include transmitting the score through a network to a user device or other external device for viewing on the external device. Consistent with disclosed embodiments, outputting may include storing the score in a location that may be accessible by one or more other computing devices. Accordingly, the score may be accessed from an external device to be displayed on the external device. In some embodiments, the method may include updating a personnel record of the subject with the competency score. Consistent with disclosed embodiments, the method may include presenting in association with the score, a link to at least one video clip.

At step 1970, process 1900 may include presenting in association with the at least one score, a link to the at least one video clip. As described herein, a link may be presented such that when the link is selected, the corresponding video clip may be presented for viewing. As described herein, the score and link may be presented, for example, in an interface in which a user may view the score and actuate the link to view the corresponding video. According to disclosed embodiments, the method may further include classifying a surgical procedure type associated with the video clip and presenting a control enabling a viewer to access other video clips in which the subject is presented sharing the surgical procedure type.

Aspects of the present disclosure relate to systems, computer readable media, and methods for aggregating and analyzing medical information. In particular, aspects of the disclosure involve analyzing time and location information associated with a piece of medical equipment to associate medical information with a patient medical record.

When capturing medical data during a medical procedure, correct identification of a room or a space corresponding to the medical data may be valuable and even necessary for properly correlating captured data. For example, the identity of an operation room may be used in conjunction with scheduling information to determine a case number, a type of medical procedure, a patient undergoing the medical procedure, a healthcare professional performing the medical procedure, and so forth. Accordingly, the captured medical data may be automatically linked with other medical information.

In many instances, the medical equipment used to capture this medical data, such as laparoscopic towers or other equipment, are used in multiple rooms. For example, some medical devices may be hand-held or may be placed on carts for easy transfer between rooms. Thus, multiple rooms may share a common piece of equipment, or if equipment in one room malfunctions, equipment from other rooms may be brought in as a backup. As a result, identifying the equipment alone may be insufficient for properly linking the captured medical data with a patient or other entity. Therefore, there is a need for unconventional approaches to automatically determine an operating room location for linking medical data with the correct patient medical record or other information about a medical procedure.

Aspects of this disclosure may relate to receiving medical information from a piece of medical equipment and associating the medical information with a particular medical record. Accordingly, the medical information may be made accessible through access to the medical record. In particular, the present disclosure may include receiving location and time information associated with the medical equipment. The location and time information may then be used to determine an identity of a particular patient associated with the medical information, which may then be used to identify the medical record.

This may be particularly applicable in instances for information captured by mobile equipment. For example, the equipment may be hand-held or may be placed on a cart in order to be easily transferred between rooms. Accordingly, identifying the equipment alone may not be sufficient to associate medical data with the correct patient or medical record. Further, performing this form of electronic analysis and aggregation of data may not feasibly be performed manually. For example, a medical facility may have hundreds of associated patients undergoing medical procedures at any given time. Because the data may need to be analyzed in real time to provide meaningful insights, manually tracking schedules and equipment locations to identify associated patients or patient medical records may be an insurmountable task. Therefore, the disclosed techniques for linking time and location information to medical data described herein overcome several technological problems relating to efficiency, convenience, and functionality in the field of medical data capturing and analysis.

For ease of discussion, in some instances, a method is described below with the understanding that aspects of the method apply to systems, devices, and computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities. Collectively and individually, systems, devices, and computer readable media disclosed herein are referred to generally as "embodiments."

Aspects of the present disclosure may involve receiving an identifier (ID) of a piece of equipment in a medical facility. As used herein, a piece of medical equipment may refer to any apparatus, instrument, tool, or other device used as part of a medical procedure. For example, the piece of medical equipment may include, but is not limited to a blood pressure monitor, a ventilator, an anesthesia delivery machine, an oxygen concentrator, a sleep apnea machine, a kidney dialysis machine, an infusion pump, an insulin pump, a blood analyzer, a respiratory monitoring machine, and a fluid management system. Other examples medical equipment may include cutting instruments (such as scalpels, scissors, or saws), grasping and/or holding instruments (such as Billroth's clamps, hemostatic "mosquito" forceps, atraumatic hemostatic forceps, Deschamp's needle, or Hopfner's hemostatic forceps), retractors (such as Farabef's C shaped laminar hook, blunt-toothed hook, sharp-toothed hook, grooved probe, or tamp forceps), tissue unifying instruments and/or materials (such as needle holders, surgical needles, staplers, clips, adhesive tapes, or a mesh), protective equipment (such as facial and/or respiratory protective equipment, headwear, or footwear), laparoscopes, endoscopes, patient monitoring devices, and so forth. In some embodiments, the piece of medical equipment may be configured to capture medical information during a medical procedure. Some non-limiting examples of such medical information may include sensor data, image data, video data, audio data, or other forms of information as described in greater detail below. In some embodiments, the piece of medical equipment may include at least one image sensor configured to capture images and/or videos.

Consistent with some embodiments described herein, the piece of medical equipment may be movable from between spaces in the medical facility. For example, the piece of medical equipment may be a handheld device or apparatus that may be carried by an individual between multiple spaces. As another example, the piece of medical equipment may have wheels (either integral to the medical equipment or by virtue of the medical equipment being placed on a cart or other wheeled apparatus) such that the piece of medical equipment may be rolled between spaces. Various other mechanisms for moving the piece of medical equipment may be used, such as a track system, a drone, a pulley system, a swivel system, or the like.

The ID of the piece of medical equipment may be any form of information that may identify a particular piece of equipment. In some embodiments, the ID may be contained within an active or passive electronic tag included as original equipment with a piece of medical equipment or a tag added later. A database, lookup table, or other data structure may correlate a particular assigned tag with a particular piece of medical equipment. An ID of the piece of equipment may additionally or alternatively include a unique identifier of the piece of equipment. For example, the unique identifier may be an alphanumerical serial number associated with a particular piece of equipment, a numerical identifier (for example, a binary number, a decimal number, a hexadecimal number, etc.), a digital identifier, and so forth. The unique identifier may be assigned by a manufacturer of the equipment, or may be assigned by a particular medical facility or organization. In some embodiments, the unique identifier may be a randomly or semi-randomly generated identifier. Alternatively, or additionally, the unique identifier may be generated according to a numbering scheme. For example, equipment within a medical facility may be assigned identifiers incrementally, sequentially, etc. In some embodiments, at least a portion of the unique identifier may be based on information associated with the piece of equipment, such as a floor number, building number, model number, manufacturer, equipment type, or other information associated with the equipment. For example, a piece of equipment generally assigned to Floor 6 of Building 3 of a medical facility may have a unique identifier in the format of "B3-FL06-XXXXX."

As another example, the ID of the piece of equipment may include information indicating a type of the piece of equipment. For example, the type may include a make, model, manufacturer, an equipment category (e.g., ventilator, dialysis machine, etc.), or similar information that may be associated with a particular type of equipment. In some embodiments, the ID of the piece of equipment may include a version number associated with the equipment. For example, this may include a hardware version, a date of manufacture of the equipment, a version of software installed on the piece of medical equipment, a date of installation of the software, or any other information that may indicate a version. Alternatively, or additionally, the ID may include various other attributes or characteristics that may be used to identify the piece of equipment, such as a size, configuration, maintenance date, battery percentage or performance, operating frequency, response time, acoustic signal, or various other characteristics that may be unique or at least semi-unique to a piece of equipment.

The disclosed embodiments may further involve receiving location information for the piece of equipment. As used herein, location information may refer to any information indicating the relative or the absolute position of a piece of equipment within a medical facility. As described above, the location information may identify a space in which the piece of medical equipment is located. As used herein, a space may not necessarily be a room but may include other areas, such as a hallway, a doorway, an entryway, a stairway, a station, or other spaces. In some embodiments, a space may be an area or region within a room. For example, a room may include multiple similar pieces of medical equipment and the location information may specify a particular location or region within a room where the equipment is placed. In some embodiments, the piece of medical equipment may be common to a single room having multiple spaces. For example, an operating room may include multiple operating tables or other facilities for performing medical operations, and the piece of medical equipment may be on a track or swivel system such that it may be used in more than one space within the operating room. Accordingly, the location information may specify which space within the room the piece of medical equipment is being used with.

The location information may be represented in a variety of different formats. In some embodiments, the location may be determined by one or more indoor positioning systems. Such systems may employ proximity sensors, WiFi sensors, ultra-wide band sensors, acoustic sensors, infrared sensors, and/or any other type of sensor enabling a location or an approximate location to be determined. Similarly, the location may be based on satellite data, such as a Global Navigation Satellite System (GNSS). This may involve, for example, an indoor GPS repeater. For example, the piece of medical equipment may include a Global Positioning System (GPS) receiver configured to determine a location based on triangulation of information received from a plurality of satellites. Other examples of GNSS that may be similarly affected include Galileo, Globalnaya Navigazionnaya Sputnikovaya Sistema (GLONASS), and the BeiDou Navigation Satellite System (BDS).

In some instances, GPS data may be insufficient for determining a location of the medical equipment, for example, when the equipment is located indoor. Accordingly, various other techniques, such as the indoor positioning systems described earlier, may be used for determining a location. In such embodiments, the location may be determined based on a positioning system within the medical facility, which may use a beacon device or other form of transceiver device, such as wireless transmitter 145 (which may equally be configured to receive transmitted signals, as described above). For example, the piece of equipment may include at least one transmitter configured to transmit location signals to at least one receiver associated with the location. The receiver may be any device capable of receiving wireless signals transmitted by the medical device. The signals may be transmitted through various formats or protocols. For example, this may include Bluetooth®, infrared light, near-field communication (NFC), ultra-wideband, ZigBee®, Z-Wave®, WiFi, ultrasonic signals, audible signals, or any other mechanism or protocol through which at least one-way communication may be established. The signal may be a predetermined ping or other standardized signal, which may be detected by the receiver. In some embodiments, the signal may include identifying information of the piece of equipment, such as the ID described above.

The received location information may be determined based on the signals detected by the at least one receiver. For example, the receiver may be installed in an operating room and when the piece of medical equipment transmits the signal to the receiver, the signal detected at the receiver may indicate the presence of the piece of medical equipment in the room. This may be based on detection of the signal alone, or based on other factors, such as the strength of the signal, a wavelength of the signal, a clarity of the signal, a timing of the signal, or other characteristics. In some embodiments, the receiver may be connected to a central system (e.g., a server or other computing device associated with the medical facility, a remote server or computing device, etc.) and the receiver may report the detected location to the piece of medical equipment to the central system. For example, the receiver may be associated with an identifier and the receiver may transmit a signal including the identifier which may indicate the piece of medical equipment is detected in proximity to the receiver. In embodiments where the signal includes identifying information for the piece of medical equipment, the identifying information may also be transmitted by the receiver.

In some embodiments, the location information may be based on signals received at multiple receivers positioned in the medical facility. For example, the signal may be received at multiple receivers located in the medical facility and the system may determine the location information based on triangulation or other location techniques. Triangulation or other techniques may be based on timings of received signals, signal strengths or other attributes of signals received at the receivers, as described above. In one example, one or more beacons and/or receivers that are nearest to the medical equipment (of a plurality of beacons and/or receivers) may be identified, for example based on comparison of signal strength, comparison of time of arrival, and so forth, and the location information may be based on the identified nearest one or more beacons and/or receivers.

Conversely, the piece of medical equipment may be configured to receive signals from a beacon device or other form of transmitter for purposes of determining a location. For example, an operating room may include a transmitter, such as wireless transmitter 145, and the piece of medical equipment may determine a location based on receipt of a signal transmitted by the transmitter. Accordingly, the piece of medical equipment may be configured to transmit the determined location along with captured medical data. As described above, the location may be determined based on detection of the signal alone, or based on other factors, such as the strength of the signal, a wavelength of the signal, a clarity of the signal, a timing of the signal, or other characteristics. In some embodiments, the transmitters in the medical facility may transmit an identifier or other means for the piece of medical equipment to determine the transmitter from which the signal is received. As described above, the location information may be determined based on triangulation of signals received from multiple transmitters. According to some embodiments, the location information may be determined based on two-way communication between receivers and transmitters. For example, the piece of medical equipment may ping beacon devices positioned throughout the medical facility and may receive signals for determining location in return, or vice versa.

As another example, the location information may be determined based on captured images associated with the piece of medical equipment. For example, the piece of equipment may include at least one image sensor and the location information may include image data captured by the image sensor. As described generally throughout the present disclosure, the image sensor may be any device capable of capturing and processing light signals from within an environment, such as a camera or LiDAR sensor. The disclosed methods may include processing the image data to determine an identity of a space corresponding to the location. For example, an operating room may have distinguishing characteristics such as equipment placement (e.g., operating tables, furniture, lights, devices, or other equipment), room layout (e.g., based on the placement of windows, walls or doors; room dimensions, room shape; ceiling contours, or other layout properties), color (e.g., paint color, equipment color, etc.), lighting properties, individuals within the room (e.g., physicians, nurses, technicians, etc.), equipment types or combinations of equipment, types of medical procedures being performed, artwork, patterns, or other visual characteristics that may distinguish a space from other spaces in a medical facility. In some embodiments, the space may include a tag or other distinguishing feature unique to the space. For example, determining the location information may include analyzing one or more images to detect a room number, room name, a scannable code (e.g., a barcode, a quick response (QR) code, an encoded image, a proprietary code, or similar formats), or other visual tags that may be used to identify a room. For example, a piece of medical equipment may include a receiver, and a room may contain a passive or active tag from which the piece of medical equipment can determine its own location.

In some embodiments, the images may be captured by an image sensor separate from the piece of medical equipment. For example, a room or other space may include a camera or other sensor configured to capture images within the space. The disclosed methods may include analyzing the images to detect representations of pieces of equipment within the captured images of the room. For example, the system may detect a particular piece of equipment based on visual characteristics of the equipment, such as the shape, color, texture, size, or other properties of the equipment. As another example, the equipment may include a tag with a barcode, QR code, alphanumerical identifier, or other information that may be detected in the images.

The location information may be received based on various timings or triggers. In some embodiments, the location information may be received periodically, for example, every few seconds, every few minutes, hourly, daily, weekly, or based on other suitable intervals. As another example, the location information may be received based on a detected change in location. For example, the piece of medical equipment or an external device may periodically determine a position of the equipment using the techniques described above and may only transmit the location information upon detecting a change from a previous location. In some embodiments, the location information may be received based on triggers associated with a medical procedure, such as the beginning of a procedure, the end of a procedure, a detected intraoperative event during the procedure, or various other triggers. As another example, the location information may be triggered manually, for example, by a medical professional, a patient, an administrator, or other individuals.

Disclosed embodiments may involve receiving medical information captured by the piece of equipment during a medical procedure. As used herein, a medical procedure may be any operation or course of action associated with healthcare of a patient. For example, a medical procedure may include a propaedeutic procedure (e.g., inspection, auscultation, palpation, percussion, measurement), a diagnostic procedure (e.g., a lab test, an endoscopy, an electrocardiogram, medical imaging, neuroimaging, an evoked potential test, posturography, or other tests), a therapy (e.g., nebulization, electrotherapy, laser therapy, radiation therapy, chemotherapy, hemodialysis, or other treatments), anesthesia, or other procedures. In some embodiments, the medical procedure may include a surgical procedure as described throughout the present disclosure. For example, the medical procedure may include one or more of surgeries, repairs, ablations, replacements, implantations, extractions, treatments, restrictions, re-routing, and blockage removal. Such procedures may involve cutting, abrading, suturing, extracting, lancing or any other technique that involves physically changing body tissues and/or organs. In some embodiments, the medical procedure may be a veterinary procedure and the medical professional performing the procedure may be a veterinarian.

The medical information may include any data or information captured by a piece of equipment during the medical procedure. In some embodiments, the medical information may include a reading or measurement from a sensor associated with the piece of medical equipment. For example, the piece of equipment may be configured to capture a vital sign of a patient and the captured medical information may include the vital sign. For example, the vital sign may include a body temperature, a blood pressure, a pulse (heart rate), a breathing rate (respiratory rate), a pain level, a menstrual cycle, an oxygen saturation, a blood glucose level, or various other vital signs. The captured medical information may include other measurements that may be associated with a patient or a physical feature of a patient, such as a height, a weight, a width, a distance, a density, a rate, a temperature, a frequency, a volume, a hardness, an amplitude, a duration, an electrical current, a luminosity, or various other measurements.

As another example, the medical information may include image data of a procedure performed on the particular patient. In some embodiments, the image data may include video footage of the medical procedure. For example, the medical procedure may include a surgical procedure, and the medical information may include footage of the surgical procedure. The disclosed systems may analyze image data (e.g., included in the video footage) to monitor, track, report, assess, or otherwise evaluate various aspects of a procedure. For example, the system may detect intraoperative events that occur during a medical procedure. Various examples of surgical footage and other forms of image data are described in greater detail throughout the present disclosure.

The disclosed embodiments may involve ascertaining a time of information capture by the piece of equipment. The time may be determined based on a clock associated with one or more devices of the system. For example, the time may be determined based on a quartz crystal oscillator and associated circuitry or other time-keeping hardware included within the piece of medical equipment. In some embodiments, the time may be determined, at least in part, based on external information, such as WiFi or other network data. Accordingly, the medical information may be associated with a timestamp or other information indicating a time of capture. In some embodiments, the time may be determined based on a clock associated with another device, such as a central computing device that receives the medical information. For example, the time of capture may be estimated based on the time it is received.

The disclosed embodiments may further involve accessing at least one data record. A data record may be any form of electronic data that associates scheduled medical procedures with locations of medical procedures and patient information. In some embodiments, the data record may be a calendar indicating scheduled medical procedures and associated rooms where the procedures will be performed. For example, this may include medical facility scheduling software assigning patients to spaces at particular times. The data record may be represented in other data formats, such as a database, table, array, spreadsheet, list, or various other data structures, as defined throughout the present disclosure. The data record may include other information, such as a physician, surgeon, or other medical professional performing the procedure, a nurse, technician, or other support staff involved with the procedure, a type of procedure being performed, equipment associated with the procedure, patient data (e.g., diagnosis data, past treatments, medications, etc.), adjacent scheduled procedures (e.g., temporally, in neighboring spaces, etc.), expected duration, contingent locations for performing the procedure, or the like.

Disclosed embodiments may further involve performing a look-up in the data record to determine an identity of a particular patient assigned to a location associated with the location information. For example, the particular patient may be a patient scheduled to undergo a medical procedure in the location associated with the location information. The look up may be performed using the location information and the ascertained time. For example, the disclosed embodiments may include cross-referencing the location information and the ascertained time with a data record to identify a procedure scheduled to occur within the specified location at the specified time. Accordingly, the system may determine the particular patient is likely the subject of the medical information captured during the medical procedure. By way of non-limiting example, if a patient (or the use of medical equipment) is detected in a particular operating room, a system may perform a look-up in a scheduling database for the identity of a patient scheduled to be in that particular operating room at that particular time. Thereafter, the data derived from the medical equipment in that space may be associated with that particular patient's electronic medical record.

Consistent with the present disclosure, the identity of the patient may be determined using various other forms of wireless transmitters and/or receivers. For example, a wireless transceiver may be worn by a physician or other medical professional in the space where the medical procedure is being performed. For example, wireless transmitter 145 may be worn by a surgeon and may transmit a signal that is received by the piece of medical equipment. The signal may include an identifier associated with the surgeon which may be used to perform the look up described above. For example, the system may look up a schedule of the surgeon along with a time of capture to determine a particular patient assigned to the surgeon at the time of capture. Alternatively, or additionally, the piece of medical equipment may transmit a signal to a wireless receiver worn by the medical professional, which may be used to correlate the data captured by the medical equipment to a particular medical professional. For example, the wireless transmitter worn by the medical professional may transmit the ID of the piece of medical equipment along with a medical professional identifier to a central system for performing a lookup function. Multifactor identification may be employed in that more than one piece of information may need to align with existing records in order to verify a patient in a space. For example, the presence of both an assigned surgeon and one or more other assigned medical professionals (or pieces of medical equipment) scheduled to be with a particular patient during a particular time in the particular space may be used to enhance identity verification.

As another example, a wireless transmitter or receiver may be worn by a patient, which may verify the patient's ID. The piece of medical equipment may transmit a signal including the ID of the piece of medical equipment to a wireless receiver worn by the patient to thereby associate the data captured by the equipment to a particular patient. Similarly, a wireless transmitter worn by the patient may transmit a signal to the equipment. For example, the signal may include a patient ID, which may be used to identify a particular patient.

Embodiments of the present disclosure may further include accessing a medical record data structure. As described throughout the present disclosure, a data structure may include any collection of data values and relationships among them. Accordingly, the medical record data structure may indicate relationships between patients and associated medical records. For example, the data structure may include a database of patients and associated patient medical records. As used herein, a medical record may include any form of structured or unstructured data documenting a patient's care over time. In some embodiments, each patient in the medical record data structure may be associated with one or more medical records. For example, a physician associated with the patient, a nurse associated with the patient, a specialist associated with the patient, or the like, may each generate a separate medical record for the patient. Alternatively, each patient may be associated with a single aggregated medical record including data from one or more sources. One or more records may be collated and/or stored in the same data structure, or the one or more records may be distributed across a plurality of data structures. The records may be stored and/or represented a plurality of electronic data formats. For example, the patient records may be represented as one or more electronic files, such as text files, portable document format (PDF) files, extensible markup language (XML) files, or the like. The medical record data structure may include the medical records themselves, or may include links, location information, or other data suitable for identifying or accessing the medical records.

Disclosed embodiments may further involve performing a lookup in the medical record data structure to identify a medical record of the particular patient. For example, the lookup may be performed using the identity of the particular patient determined in any of the exemplary ways described above. In some embodiments, the look up may be performed using a name of the patient. For example, the data record described above may indicate a patient name and the look up may be performed using the determined patient name. Various other information identifying a patient may be used as the patient's identity. For example, the identity of the particular patient may include an anonymized patient ID, such as an alphanumeric string assigned to the patient. The patient ID may be an identifier assigned to the patient by the medical facility or a medical system or organization, or may be a global identifier. Performing a lookup in the medical record data structure to identify a medical record of the particular patient includes using the anonymized ID to locate the medical record of the particular patient. Various other forms of patient identifiers may be used, such as a data of birth, a phone number, an address, a social security number, or other data that may be tied to the identity of a particular patient.

Further, disclosed embodiments may involve establishing an association between the medical information captured by the piece of equipment and at least some information in the medical record of the particular patient. Accordingly, establishing the association may enable access to the medical information captured by the piece of equipment through access to the medical record of the particular patient. In some embodiments, establishing the association may include adding or writing data to the medical record. For example, as described above, the captured medical information may include image data of a procedure performed on the particular patient. Accordingly, establishing the association may include storing at least part of the image data in the medical record. For example, this may include storing an image, a plurality of images (e.g., a series of consecutive images, a group of selected images, etc.), a video clip, or other forms of image data in the medical record. This may include storing the image data in a raw format, a processed format, a compressed format, a report format, or any other suitable format.

As another example, establishing the association may include embedding a link in the medical record to connect to the medical information from another data source. For example, as described above, the medical information may include a vital sign of the patient or image data captured by the piece of medical equipment. Establishing the association may include linking the image data, vital sign of the particular patient, or other forms of medical information with the medical record of the particular patient. In particular, when the medical information includes video footage of the medical procedure, establishing the association may include storing the video footage in a video footage repository and embedding in the medical record a link to the stored video footage. For example, the video repository may be a database, such as database 411 described above. Various other repositories may be used, which may include a local memory device, such as data storage 413, a cloud-based storage platform, a remote server, or the like.

In some embodiments, the disclosed embodiments may involve processing image data and analyzing the processed data. Information determined based on the processed image may be used to establish the association with the medical record. For example, as described above, the medical information may include image data of a procedure performed on the patient. The disclosed methods may further include calculating at least one convolution of the image data. The convolution may be a 2D convolution, a 3D convolution, etc. For example, the convolution may include one or more image filters, such as low-pass filters, high-pass filters, band-pass filters, all-pass filters, and so forth. In other examples, the transformation function may comprise a non-linear function. Other examples may include a Gaussian convolution, a median filter, a representation of at least part of the image data in a frequency domain, a Discrete Fourier Transform of at least part of the image data, a Discrete Wavelet Transform of at least part of the image data, a time/frequency representation of at least part of the image data, a representation of at least part of the image data in a lower dimension, a lossy representation of at least part of the image data, a lossless representation of at least part of the image data, a time ordered series of any of the above, or any combination of the above.

The disclosed embodiments may further involve determining information based on the calculated at least one convolution. For example, the processed image may enable additional information to be extracted relative to the original unprocessed image. For example, the processed image may be used for analyzing image data using various methods and algorithms described herein. In one example, the calculated at least one convolution may be used as an input to at least one of a trained machine learning model, an artificial neural network, an artificial neuron, a non-linear function and an activation function, and the determined information may include and/or be based on the corresponding output of the at least one of the trained machine learning model, the artificial neural network, the artificial neuron, the non-linear function and the activation function. The disclosed methods may further include linking the determined information with the medical record of the particular patient to establish the association, as described above.

The linked medical data may be used in various ways. In some embodiments, the disclosed embodiments may further include outputting data based on the association. For example, this may include transmitting or storing output data. The output may include any format of electronic data indicating the association. In some embodiments, the output may include a link to the medical record or the stored captured medical information. In other embodiments, the output may include the medical record or captured medical information. Consistent with the present disclosure, outputting the data may include presenting a video file to a user through a graphical user interface. Based on the look up operations performed as described above, the system may be able to accurately determine a patient, and therefore associated medical professionals, who may be interested in the video footage. In some embodiments, the output may be used for scheduling purposes. For example, the output may indicate that a medical procedure has concluded and therefore the piece of medical equipment is available for use in other spaces, or that the space is available for other procedures.

As another example, the disclosed embodiments may further involve transmitting patient-specific alerts based on information in the medical record. The alerts may include any information associated with the particular patient that may be determined based on the established association. The alert may be transmitted to the particular patient, a family member of the particular patient, a representative of the particular patient (e.g., a health care surrogate, an individual having medical power of attorney, etc.), a healthcare physician associated with the particular patient, a medical organization (e.g., a clinical trial organization, a research organization, etc.), an insurance company, the medical facility, or any other party that may be interested in the associated data. The alert may indicate that the medical record has been updated, that the medical procedure has been performed, that the medical procedure as begun, the time or location of the medical procedure, the type of equipment used, an identity of the equipment, information about the captured medical information (e.g., a detected intraoperative event, a detected adverse event), a detected or predicted potentially harmful drug interaction, or any other information about the established association.

In some embodiments, the disclosed embodiments may involve analyzing the medical information in conjunction with the medical record of the particular patient. In particular, the disclosed embodiments may involve retrieving information from the medical record of the particular patient and using the retrieved information to analyze the medical information captured by the piece of equipment. The embodiments may then involve providing information based on the analysis of the medical information captured by the piece of equipment. For example, this may include determining whether a proper medical procedure was followed based on the patient's medical information, such as the patient's diagnosis, health condition, gender, age, medications, preferences, or other information that may affect a proper procedure. As another example, this may include determining a progression of a disease for a patient. For example, the medical information may include the size of a tumor or growth measured during a medical procedure and the analysis may include comparing the current measurements to past measurements for the tumor. Accordingly, the system may be configured to automatically assess a progression of the disease. While example analysis is provided above, various other forms of analysis, including those described throughout the present disclosure may be performed to generate information.

In some embodiments, the information may be provided during the medical procedure. For example, this may include generating an alert or notification for a physician performing the medical procedure, which may inform the physician of a correct procedure to follow, an update to the procedure, a recommended response to an adverse event, a recommended medical tool, a recommended medical technique, a recommendation to stop a medical procedure, a notification or reminder of an underlying condition or other health information of the patient, or various other patient-related information that may be useful to a physician during a medical procedure. The information may be provided at other stages of the medical procedure, such as after completion of the procedure. For example, the information may allow the physician to review events or portions of the procedure in reference to information associated with the patient's medical record. Similarly, the information may be provided to nurses, technicians, support staff, medical facility administrators, or the like. In some embodiments, the information may be used to generate a patient-specific alert as described in further detail above.

Figure 22:
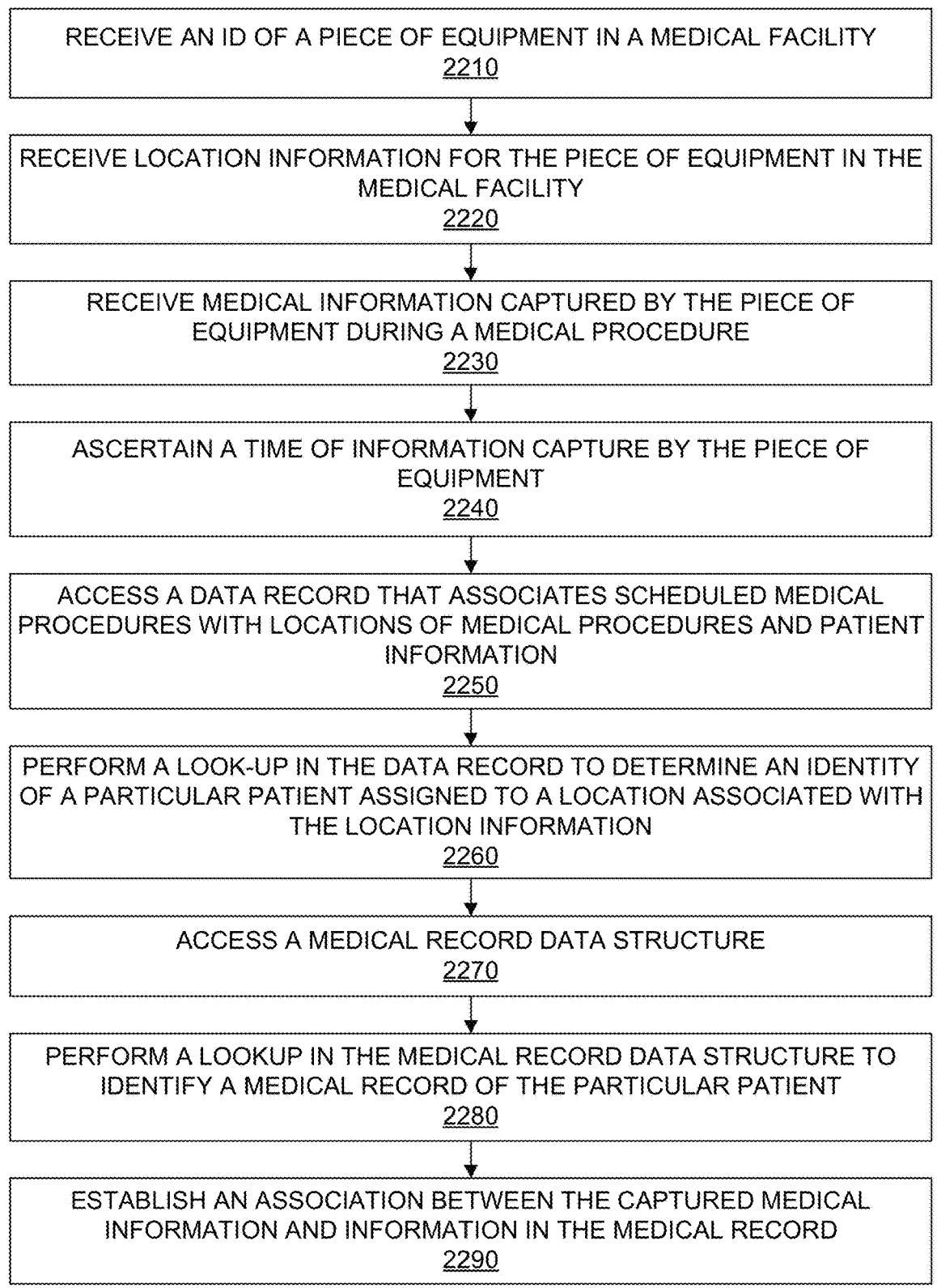
FIG. 22 is a block diagram illustrating an exemplary process for aggregating and analyzing equipment, time, and space data to update medical records, consistent with disclosed embodiments.

FIG. 22 is a block diagram illustrating an example process 2200 for aggregating and analyzing equipment, time, and space data to update medical records, consistent with disclosed embodiments. Process 2200 may be performed by one or more processors, such as processors 412. In some embodiments, a non-transitory computer readable medium may contain instructions that when executed by a processor cause the processor to perform process 2200. Process 2200 is not necessarily limited to the steps shown in FIG. 22 and any steps or processes of the various embodiments described throughout the present disclosure may be included in process 2200.

At step 2210, process 2200 may include receiving an ID of a piece of equipment in a medical facility. As described above, the ID may include any form of information that may be used to identify a particular piece of equipment. For example, the ID may include a unique identifier and an identifier of equipment type. The piece of equipment may include at least one of a blood pressure monitor, a ventilator, an anesthesia delivery machine, an oxygen concentrator, a sleep apnea machine, a kidney dialysis machine, an infusion pump, an insulin pump, a blood analyzer, a respiratory monitoring machine, and a fluid management system.

At step 2220, process 2200 may include receiving location information for the piece of equipment in the medical facility. In some embodiments, the location information may include image data captured by an image sensor. Alternatively, or additionally, the location information may be received based on signals detected by at least one receiver, as described above.

At step 2230, process 2200 may include receiving medical information captured by the piece of equipment during a medical procedure. For example, the medical information captured by the piece of equipment during the medical procedure may include image data of a procedure performed on the particular patient. As another example, the piece of equipment may be configured to capture at least one vital sign, and the captured medical information may include at least one vital sign of the particular patient. Various other example medical information is described above.

At step 2240, process 2200 may include ascertaining a time of information capture by the piece of equipment. For example, the medical information captured by the piece of equipment may include timestamp information indicating the time of capture. As another example, the time of capture may be based on a time of receipt of the information.

At step 2250, process 2200 may include accessing at least one data record that associates scheduled medical procedures with locations of medical procedures and patient information. In some embodiments, this may include accessing medical facility scheduling software assigning patients to spaces at particular times. At step 2260, process 2200 may include performing a look-up in the data record using at least the location information and the ascertained time to determine an identity of a particular patient assigned to a location associated with the location information. For example, the patient may be scheduled to undergo a medical procedure in a room or other space associated with the location information at the time of capture.

At step 2270, process 2200 may include accessing a medical record data structure. For example, the medical record data structure may be a database associating patient names with one or more medical records. Various other example data structures are described above. At step 2280, process 2200 may include performing a lookup in the medical record data structure using the identity of the particular patient to identify a medical record of the particular patient. In some embodiments, the identity of the particular patient may include an anonymized patient ID. Accordingly, performing a lookup in the medical record data structure to identify a medical record of the particular patient may include using the anonymized ID to locate the medical record of the particular patient.

At step 2290, process 2200 may include establishing an association between the medical information captured by the piece of equipment and at least some information in the medical record of the particular patient. This may enable access to the medical information captured by the piece of equipment through access to the medical record of the particular patient. For example, establishing the association between the medical information and the medical record may include recording or storing vital signs, image data (e.g., images, video footage, etc.), or other information in the medical record. In some embodiments, establishing the association may include embedding a link in the medical record to connect to the medical information from another data source.

Aspects of the present disclosure relate to systems, computer readable media, and methods for assigning surgical teams to prospective surgical procedures. Aspects of the disclosure involve using artificial intelligence and computer image analysis to determine requirements associated with a prospective surgery, determining whether a particular surgeon meets the requirements associated with the prospective surgery, and outputting an indication that the particular surgeon meets the requirements.

Proper operating room scheduling is fraught with difficulties. Aside from the logistics of efficiently using space, surgeons need to be efficiently used and skill sets of surgeons need to be appropriately matched with the needs of certain patients and expected complications based on patient profile data. A change in one parameter can have a cascading effect on an entire schedule, making efficient human manipulation very difficult. Conventional methods for scheduling surgical teams may be limited in access to data. For example, a scheduler may have no or little access to data beyond the scheduler's personal knowledge or experience, and even then, balancing the myriad of factors across a myriad of teams scheduled to be in various operating rooms at overlapping times may pose difficult challenges unsolvable with conventional technology.

Therefore, there is a need for unconventional approaches to assist in scheduling surgeries and surgical teams by using data made available as a result of computer image analysis using machine learning techniques. These unconventional approaches allow data driven decisions in assigning surgical teams, such as ensuring that residents obtain appropriate exposure to training opportunities or other requirements to complete their residency, or by ensuring the most skilled surgeons are assigned the most complicated patients, or that more efficient surgeons are assigned to procedures when time is of the essence. The system may automate the assignment of surgical teams. In another concept, preparation materials such as links to videos of similar surgeries for review may be provided according to a schedule for a surgeon.

Aspects of this disclosure may relate to using machine learning-enabled video processing analysis of video feeds to facilitate assignment of surgical teams to prospective surgeries. For example, some of the disclosed embodiments provide solutions for assigning and scheduling surgeons to prospective surgeries based on characteristics of prospective surgeries and characteristics of surgical teams determined by analyzing video frames of prior surgical procedures. Some disclosed embodiments provide solutions for assisting a scheduler to assign surgical teams by determining a level of skill of a particular surgeon, an expected amount of time for the particular surgeon to perform the prospective surgery, requirements for the prospective surgery, and whether the particular surgeon meets the requirements.

Aspects of this disclosure may relate to assigning surgical teams to prospective surgeries. A surgical team, in its broadest sense, may include one or more surgeons, and may also include one or more medical assistants such as nurses, technicians, or other physicians or support staff who may be involved in a surgical procedure. Assigning a surgical team may include selecting or scheduling one or more individuals to perform prospective surgeries or aid a user such as a scheduler in performing the same. Assigning surgical teams or individual members of a surgical team to prospective surgeries may involve publishing a schedule or otherwise notifying a surgical team or individual surgical team member of an assignment to a prospective surgery, providing instruction and/or information to a system that facilitate scheduling, such as a calendar. A prospective surgery may refer to a future or potential surgical procedure, as defined herein.

According to disclosed embodiments, a skill level may be ascertained. As used herein, skill level may refer to any indication or measure of an individual surgeon's relative abilities. In some embodiments, the skill level may include a score reflecting the surgeon's experience or proficiency in performing a surgical procedure or specific techniques within a surgical procedure. Skill level may be based on past performances of the surgeon, a type and/or level of training or education of the surgeon, a number of surgeries the surgeon has performed, types of surgeries surgeon has performed, qualifications of the surgeon, a level of experience of the surgeon, ratings of the surgeon from patients or other healthcare professionals, past surgical outcomes, past surgical complications, adherence to safety practices, or any other information relevant to assessing the skill level of a healthcare professional.

In some embodiments, the skill level may be a global skill level assigned to each surgeon or may be in reference to specific events. For example, a surgeon may have a first skill level with regard to a first technique or procedure and may have a second skill level with regard to a different technique or procedure. The skill level of the surgeon may also vary throughout an event, technique and/or procedure. For example, a surgeon may act at a first skill level within a first portion or phase of a procedure but may act at a second skill level at a second portion or phase of the same procedure. Accordingly, the skill level may be a skill level associated with a particular intraoperative event, portion, or stage of a procedure. A skill level also may be a plurality of sub-skill levels during an event or may be an aggregation of the plurality of sub-skill levels during the event, such as an average value, a rolling average, a median, a mode, or other forms of aggregation. A skill level may further refer to a general required skill level for performing a surgical procedure, a phase of a surgical procedure, and/or an intraoperative surgical event. A skill level may be expressed in various ways, including on a numerical scale (e.g., 1-10, 1-100, etc.), as a percentage, on a scale of text-based indicators (e.g., "highly skilled," "moderately skilled," "unskilled," etc.), or any other suitable or desired format for expressing the skill of a surgeon. While the skill level is described herein as the skill level of a surgeon, in some embodiments the skill level may be associated with a surgical team or another individual healthcare professional, such as a surgical technician, a nurse, a physician's assistant, an anesthesiologist, a doctor, or any other healthcare professional participating in a procedure.

Some embodiments may include analyzing a plurality of video frames of prior surgical procedures performed by a particular surgeon to ascertain a skill level of the particular surgeon. A process of analyzing video frames may be performed by a suitable machine-learning model such as an image recognition algorithm, as described herein. In various embodiments, information obtained from stored historical data based on prior surgical procedures may be used to train the image recognition algorithm to assess aspects of surgical procedures by recognizing and comparing specific intraoperative events, actions, timings, etc. base on accessed frames of surgical footage, as described herein. In one example, the historical data may include a statistical model and/or a machine learning model based on an analysis of information and/or video footage from historical surgical procedures (for example as described herein), and the statistical model and/or the machine learning model may be used to analyze video frames and identify deviations in the received video frames from a reference set of frames or images related to prior surgical procedures. Such automated processing and assessment techniques may provide more accurate, efficient, and objective measures of surgical competency of a surgeon, compared to manual assessment. For example, automated assessments may remove biases of human reviewers while also being conducted more quickly without requiring a human reviewer to watch and analyze video of a surgical procedure that could last several hours. A skill level of the surgeon may be determined based on how well the surgeon performs during the event, which may be based on timeliness, effectiveness, adherence to a preferred technique, a lack of injury or adverse effects, or any other indicator of skill that may be gleaned from analyzing the footage. In one example, one or more convolutions of at least part of the plurality of video frames of prior surgical procedures performed by the particular surgeon may be calculated, and the calculated one or more convolutions may be used to ascertain the skill level of the particular surgeon. For example, in response to first calculated values of the one or more convolutions, a first skill level of the particular surgeon may be determined, and in response to second calculated values of the one or more convolutions, a second skill level of the particular surgeon may be determined, the second skill level may differ from the first skill level.

As an example of analyzing using a machine learning model, a machine learning model may take one or more video frames or preprocessed image data from the video frames as input and output information related to the video frames, such as differences between the frames and reference frames. The model may compare the received frames to expected surgical events from the stored data based on prior procedures. For example, the machine learning model may recognize a type of surgical procedure based on the processed image data, and then compare the image data to an expected list of events, timing, actions by the subject, etc. Based on the comparison, deviations between the expected actions and the actual actions taken by the subject during the surgical procedure may be assessed and a skill level determined or updated. For example, specific deviations may be identified, or a level of deviation for certain specific events or event characteristics may be determined. As another example, the actual timing or length of events may be compared with expected times based on the type of surgical procedure or event. In various embodiments, such an event-based machine learning method may be trained using training examples. For example, a training example may be based on historical data related to previous surgical procedures. An event-based machine learning model such as the type shown in FIG. 8A may be used.

Some aspects of this disclosure may include accessing a data structure containing patient characteristics associated with the prior surgical procedures. The stored data may be in a data structure consistent with disclosed embodiments, such as in FIG. 5 or FIG. 6.

Stored data may include any data derived directly or indirectly from images of previous surgical procedures. This data may include, for example, patient characteristics, surgeon characteristics (e.g., a skill level), and/or surgical procedure characteristics (e.g., an identifier of a surgical procedure, an expected duration of a surgical procedure). Stored data may include correlations or other data describing statistical relationships between historical intraoperative surgical events and historical outcomes. In some embodiments, a data structure may include data relating to recommended actions, alternative courses of action, and/or other actions that may change a probability, likelihood, or confidence of a surgical outcome. For example, a data structure may include information correlating a break from a surgical procedure with an improved outcome. Depending on implementation, a data structure may include information correlating a skill level of a surgeon, a request for assistance from another surgeon, and outcomes. Similarly, a data structure may store relationships between surgical events, actions (e.g., remedial actions), and outcomes. While a host of correlation models may be used for prediction as discussed throughout this disclosure, exemplary predictive models may include a statistical model fit to historical image-related data (e.g., information relating to remedial actions) and outcomes; and a machine learning models trained to predict outcomes based on image-related data using training data based on historical examples.

Accessing stored data may include accessing stored historical data identifying intraoperative events, associated outcomes, or a recommended sequence of events. As used herein, an intraoperative event for the surgical procedure (also referred to as a surgical event) may refer to an action that is performed as part of a surgical procedure, such as an action performed by a surgeon, a surgical technician, a nurse, a physician's assistant, an anesthesiologist, a doctor, any other healthcare professional, a surgical robot, and so forth. The intraoperative surgical event may be a planned event, such as an incision, administration of a drug, usage of a surgical instrument, an excision, a resection, a ligation, a graft, suturing, stitching, or any other planned event associated with a surgical procedure or phase. Additionally or alternatively, an intraoperative event may also refer to an event occurring to an anatomical structure and/or to a medical instrument related to the surgical procedure, whether the event includes an action performed by a healthcare professional or not. One example of such an intraoperative event may involve a change in a condition of an anatomical structure.

Some aspects of this disclosure may include accessing a data structure containing patient characteristics associated with the prior surgical procedures. Patient characteristics may include any information describing a patient that may be used to characterize a patient. Examples include but are not limited to, age, weight, size, gender, allergies, tolerance to anesthetics, preexisting conditions, prior surgeries, various particulars of a patient (e.g., how many arteries need to be treated during the bypass surgery), anatomical particulars, or any other patient-related characteristics which may be taken into account in connection with a surgical procedure.

In some embodiments, operations may include accessing a surgical schedule including a plurality of prospective surgical procedures overlapping in time. A surgical schedule may include, for example, an agenda, plan or program associated with one or more surgical spaces such as operating rooms or portions thereof. A surgical schedule in some senses may include underlying data associated with an agenda, plan or program, and in other senses may also include the presentation of that data, through, for example, an interface. As described by way of example below, schedule 2100 may include an interface for displaying a scheduled time associated with completion of the ongoing surgical procedure, as well as scheduled times for starting and finishing future surgical procedures. Schedule 2100 may be implemented using any suitable approach (e.g., as a standalone software application, as a website, as a spreadsheet, or any other suitable computer-based application or a paper-based document). An example schedule 2100 may include a list of procedures and list of starting and finishing times associated with a particular procedure. Additionally or alternatively, schedule 2100 may include a data structure configured to represent information related to a schedule of at least one operating room and/or related to a schedule of at least one surgical procedure, such as a scheduled time associated with completion of the ongoing surgical procedure, as well as scheduled times for starting and finishing future surgical procedures.

Accessing may include reading or writing data associated with a schedule stored in a database or other data structure, as described herein. A surgical schedule may include timing information associated with a prospective surgery, such as start time, finish time, expected length, and date of the prospective surgery. A surgical schedule may include location information such as a hospital, facility, floor, ward, specific operating room, or a specific area within an operating room. A surgical schedule may include personnel information such as primary surgeon(s), additional surgeon(s), alternate surgeon(s), anesthesiologists, nurses, surgical technicians, or other healthcare professionals. A surgical schedule may include information relating to a plurality of surgeries which may overlap in time. For example, a surgical schedule may include a first surgery beginning at 8:00 AM in operating room 1, expected to last four hours and a second surgery beginning at 9:00 AM in operating room 2, expected to last five hours. It is to be understood that a surgical schedule may be dynamic or static. Further, a user's experience with and access to the same surgical schedule may vary depending on the user's role. For example, a scheduler may have access to a surgical schedule in progress, while surgical team members only have access to a completed surgical schedule.

Figure 21:
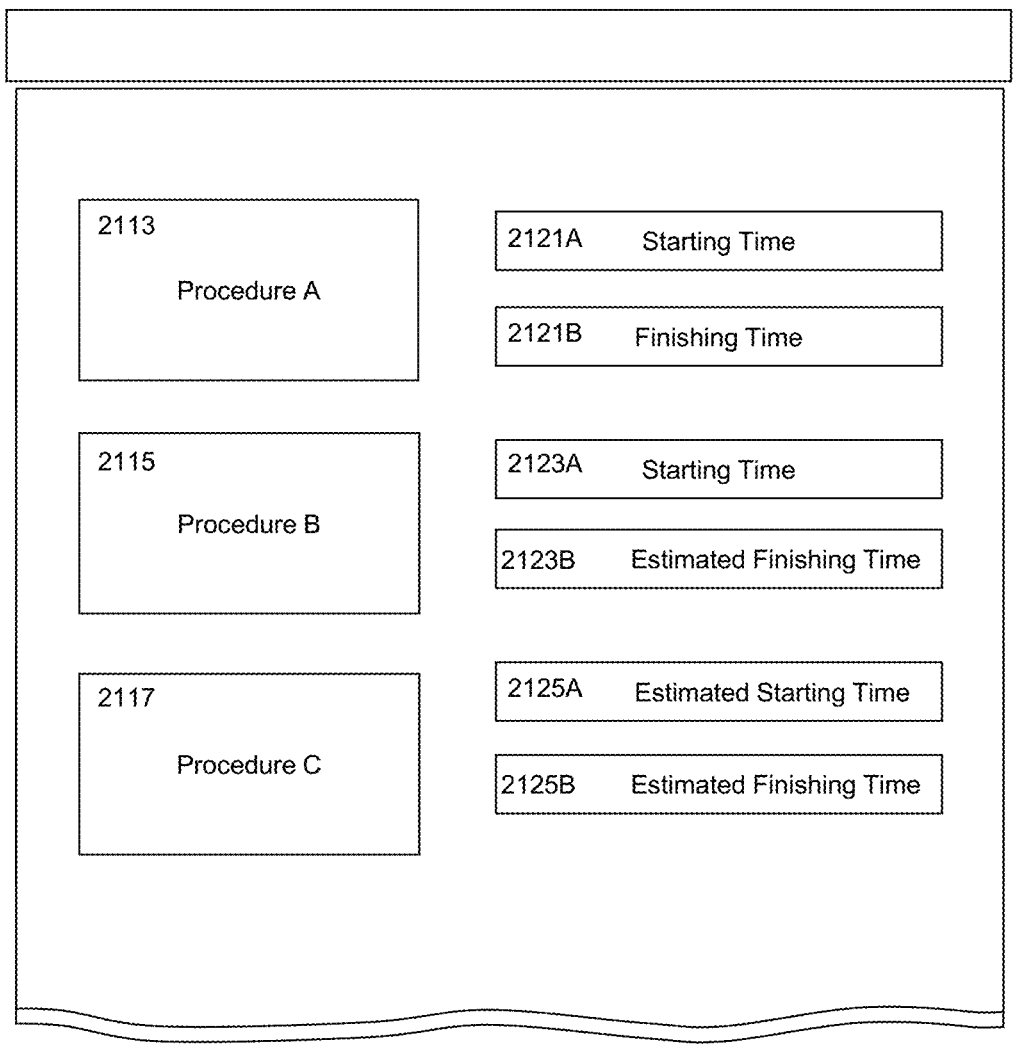
FIG. 21 is an exemplary surgical schedule, consistent with disclosed embodiments.

FIG. 21 shows an example schedule 2100 that may include a listing of procedures such as procedures A-C (e.g., surgical procedures, or any other suitable medical procedures that may be performed in an operating room for which schedule 2100 is used). For each procedure A-C, a corresponding starting and finishing times may be determined. For example, for a past procedure A, a starting time 2121A and a finishing time 2121B may be the actual starting and finishing times. (Since procedure A is completed, the schedule 2100 may be automatically updated to reflect actual times). FIG. 21 shows that for a current procedure B, a starting time 2123A may be actual and a finishing time 2123B may be estimated (and recorded as an estimated time). Additionally, for procedure C, that is scheduled to be performed in the future, a starting time 2125A and a finishing time 2125B may be estimated and recorded. It should be noted that schedule 2100 is not limited to displaying and/or holding listings of procedures and starting/finishing times for the procedures, but may include various other data associated with an example surgical procedure. For example, schedule 2100 may be configured to allow a user of schedule 2100 to interact with various elements of schedule 2100 (for cases when schedule 2100 is represented by a computer based interface such as a webpage, a software application, and/or another interface). For example, a user may be allowed to click over or otherwise select areas 2113, 2115, or 2117 to obtain details for procedures A, B or C respectively. Such details may include patient information (e.g., patient's name, age, medical history, etc.), surgical procedure information (e.g., a type of surgery, type of tools used for the surgery, type of anesthesia used for the surgery, and/or other characteristics of a surgical procedure), and healthcare provider information (e.g., a name of a surgeon, a name of an anesthesiologist, an experience of the surgeon, a success rate of the surgeon, a surgeon rating based on surgical outcomes for the surgeon, and/or other data relating to a surgeon). Some or all of the forgoing information may already appear in areas 2113, 2115, and 2117, without the need for further drill down.

Some embodiments may include obtaining patient characteristics associated with the prospective surgical procedures. As described earlier in connection with patient characteristics of prior surgical procedures, the same or similar characteristics may be obtained in a similar manner for prospective surgical procedures. A prospective surgical procedure is any surgery that has not yet occurred. Such information may be obtained in response to an input via an interface associated in some way with a surgical schedule represented by a computer-based interface such as a webpage, a software application, and/or another interface. As discussed previously, the patient characteristics may include identifying information (e.g., patient's name, age, medical history, etc.), surgical procedure information (e.g., a type of surgery, type of tools used for the surgery, type of anesthesia used for the surgery, and/or other characteristics of a surgical procedure), and/or healthcare provider information (e.g., a name of a surgeon, a name of an anesthesiologist, an experience of the surgeon, a success rate of the surgeon, a surgeon rating based on surgical outcomes for the surgeon, a surgeon skill level, and/or other data relating to a surgeon). Patient characteristics may be obtained by accessing a database storing patient characteristics using a network connection. For example, FIG. 4 is a network diagram that may include a computer system 410, a network 418, and a database 411 storing patient characteristics. Computer system 410 may access database 411 via network 418 in order to obtain patient characteristics to be included in or used to produce schedule 430. In another example, patient characteristics may be obtained from an Electronic Medical Record software.

Figure 20:
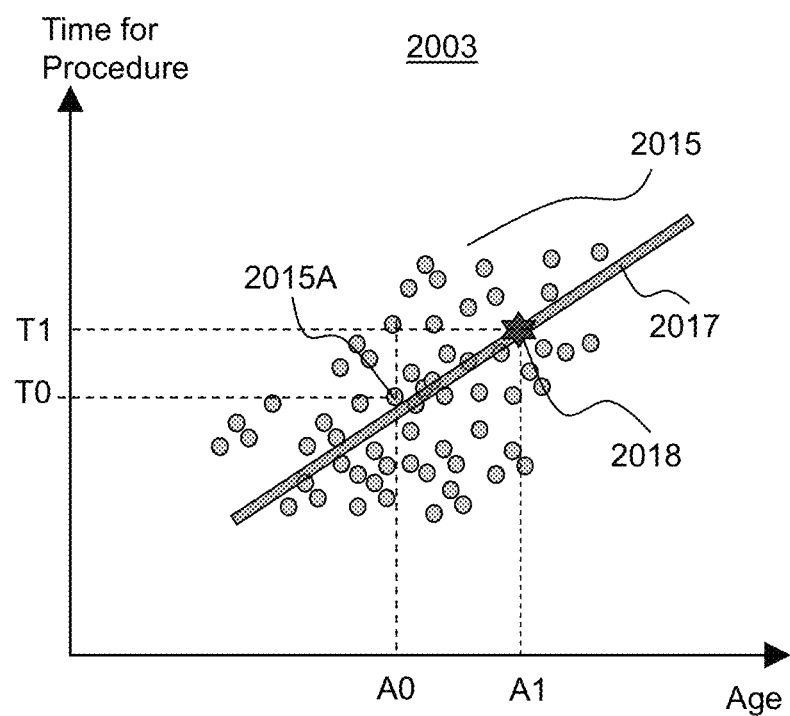
FIG. 20 shows an exemplary plot of data of historic completion times consistent with disclosed embodiments.

Some aspects of this disclosure may include analyzing a plurality of video frames of prior surgical procedures to ascertain an expected amount of time for a particular surgeon to perform at least one particular prospective surgical procedure from among a plurality of prospective surgical procedures. The analysis of the plurality of video frames of prior surgical procedures may involve any suitable statistical data analysis, such as determining an expected completion time value based on a probability distribution function, using Bayesian interference, to determine how the probability distribution function is affected by various patient/surgeon characteristics (e.g., an age of the patient), linear regression, and/or other methods of quantifying statistical relationships. The analysis of the plurality of video frames of prior surgical may determine, calculate, or estimate an expected amount of time for a particular surgeon to perform a particular prospective surgery using one or more artificial neural networks, as discussed herein. For example, an expected amount of time may be based on the analysis of the plurality of video frames of prior surgical procedures and historical data describing prior surgical procedures including the amount of time it took a particular surgeon to perform a particular surgery. For instance, FIG. 20 shows an example graph 2003 of points 2015 representing a distribution of completion time of a particular surgical procedure (e.g., a bypass surgery) for patients of different ages. For example, a point 2015A shows that in a particular case, for a patient of age A0, it took time T0 to complete the surgical procedure. Data for points 2015 may be used to construct a linear regression model 2017, and regression model 2017 may be used to determine expected completion time T1 for a patient of age A1 according to point 2018 on the linear regression model. While graph 2003 shows the dependence of the completion time on one characteristic parameter of a patient (e.g., age of the patient), completion time may depend on multiple characteristic parameters (e.g., the weight of a patient, characteristics of the healthcare professional conducting a surgical procedure, characteristics of an anesthesiologist, and other data describing a patient or procedure), as previously discussed, and points 2015 may be plotted in a multi-dimensional Cartesian coordinate system, and regression model 2017 may include multivariate regression model. In other examples, regression model 2017 may include a non-linear regression model.

In an example embodiment, determining an expected completion time may be based on one or more stored characteristics associated with a healthcare professional conducting the ongoing surgical procedure. Such characteristics may include age, a name, years of experience, a location, of the healthcare professional, past performances, skill, and/or other information describing a healthcare professional, for example, as described above. The characteristics may be stored using any suitable data structure using any suitable electronic (or in some cases, paper) storage. In an example embodiment, the characteristics may be stored in a database (e.g., database 411, as shown in FIG. 4). For instance, based on an analysis of a historical data for a given healthcare professional for a given type of surgery, an expected completion time may be estimated (e.g., the expected completion time may be an average completion time determined from the historical data for a given healthcare professional for a given type of surgery). Furthermore, using historic data for a given healthcare professional for a given type of surgery other statistics may be determined (e.g., standard deviation from the expected completion time, correlation of the expected completion time with other characteristics of a surgical procedure, such as an age of a patient or a time of the day the surgery is performed, and/or other statistic generated from historic completion times).

Some embodiments include analyzing at least some of the plurality of video frames to determine an intraoperative event therein. Analyzing the received video frames to determine an intraoperative event therein may involve any form of electronic analysis using a computing device (i.e., computer image analysis). The analysis may involve artificial intelligence applied to the video frames, such as through the use of an artificial neural network, as described herein. In analyzing intraoperative events, an expected amount of time for a prospective surgical procedure may be ascertained based on an aggregation of estimates associated with an amount of time to perform various intraoperative events.

Some embodiments may involve determining requirements for the at least one particular prospective surgical procedure, the requirements including a required skill level of a participating surgeon based on the patient characteristics associated with the at least one particular prospective surgical procedure and an expected amount of time to perform the at least one particular prospective surgical procedure. A required skill level of a participating surgeon may refer to a minimal skill level required to perform an element of a prospective surgical procedure, such as an intraoperative event. A minimal skill level may be based on patient characteristics, an expected amount of time to perform the prospective surgical procedure, the complexity of the prospective surgical procedure, a predicted probability of an intraoperative event or a patient complication, a surgical technique corresponding to the prospective surgical procedure, a surgical task correspond to the prospective surgical procedure, or any other factor or data available. Where the required skill level varies dependent on multiple factors, the minimal skill level may correspond to the highest skill level required such that a surgeon will not be assigned to a surgery beyond his or her skill level (unless adequately supervised or assisted by an additional surgeon). This determination may be made using artificial intelligence applied to video frames, as discussed herein.

Some embodiments may involve determining whether the particular surgeon meets the requirements of the at least one particular prospective surgical procedure based on the skill level of the particular surgeon and the expected amount of time for the particular surgeon to perform the at least one particular prospective surgical procedure. For example, the level of skill of a particular surgeon may be compared with the level of skill required for a particular prospective surgical procedure to ensure that the particular surgeon possess the minimal skill level to perform all of the elements of the prospective surgical procedure within the expected amount of time. The system may also determine these requirements independently. For example, the system may determine that a particular surgeon possesses the minimal skill level to perform the elements of the prospective surgical procedure but is unlikely to complete the surgical procedure within the allotted time. This determination may be made using artificial intelligence applied to video frames, as discussed herein.

Some aspects of this disclosure may include outputting an indicator that the particular surgeon meets the requirements of the at least one particular prospective surgical procedure. An indicator may include any visual or audible signal that demonstrates or shows that a particular surgeon meets the minimal requirements to perform a particular prospective surgical procedure. Outputting an indicator may include outputting code from at least one processor, wherein the code may be configured to cause the indicator to be presented. For example, a surgeon's name (or other text representing an individual surgeon or surgical team) may be presented using an alternative font, color, or appearance when displayed on a graphical user interface used by a user to assign surgeons and surgical team members to a prospective surgical procedure. Additionally or alternatively, an indicator may be output by altering the presentation of names of surgeons which do not meet the requirements or removing their names from the display. Another example of an indicator may be the inclusion of a surgeon's name (or other text representing an individual surgeon or surgical team) in a dropdown list or other representation of individual surgeons or surgical teams available to be assigned to a prospective surgical procedure. Conversely, in this example, omission of a surgeon's name (or other text representing an individual surgeon or surgical team) from a dropdown list or other representation of individual surgeons or surgical teams available to be assigned to a prospective surgical procedure may be an indicator that the surgeon or surgical team does not meet the requirements of the particular prospective surgical procedure. In one example, an indicator may include any electronic signal that provide instructions and/or information to an external system or software, such as a scheduling software, a database, a display device, and so forth.

As another example, outputting may include causing a display of an identity of the particular surgeon in association with the at least one particular prospective surgical procedure. A surgeon may be identified based on his or her name, an identification number (e.g., employee number, medical registration number, etc.) or any other form of identity. The identity may be displayed by presenting a textual of an individual surgeon, such as a name associated with the individual surgeon. Additionally or alternatively, a pictorial or graphical representation may be displayed, such as a picture or an avatar.

Some embodiments may involve assigning a particular surgeon to at least one particular prospective surgical procedure. Assigning may occur automatically as part of an automated process or in response to a user action. Assigning may include selecting, scheduling, notifying, or otherwise associating a particular surgical team or individual member of a surgical team with a particular prospective surgical procedure. Additionally or alternatively, assigning may also involve changing, updating, canceling, adding, or otherwise altering a previous assignment. For example, a scheduler (e.g., a software module or a portion of code) may automatically assign a particular surgeon to a particular prospective surgical procedure. Alternatively, an interface may provide a sub-set of appropriate surgeons for a procedure, enabling presentation of a focused pick-list, such as through a graphical user interface. If after an assignment of a surgeon to a particular surgical procedure the assigned surgeon better fits another surgical procedure scheduled for the same time (or the system undertakes an optimization to maximize surgeon-procedure fit) an adjustment may be made to the schedule and the system may change the assignment of a particular surgeon. For example, the particular surgeon may have a skill needed in another overlapping surgical procedure. In such instances, the system may reassign the particular surgeon to the other procedure. In the process of doing so, the system may run scenarios on all surgeons in a surgical schedule to ensure that surgical assignments are optimized. The assignments may be reflected or displayed in a schedule including a prospective surgical procedure and the assigned surgeon. In response to the assignment, the particular surgeon's availability may be updated.

In some embodiments, the assigning of the particular surgeon may be based on a training quota. A training quota may refer to a minimum number of surgical procedures of a particular type or intraoperative events of a particular category that a surgeon or trainee surgeon must perform or observe in order to advance in schooling, obtain a certification, or be deemed proficient and able to perform the surgical procedure or intraoperative event without supervision. As an example, a medical student or resident may be required to perform an appendectomy under supervision at least five times before being deemed proficient to perform an appendectomy without supervision. Surgeon characteristics, as disclosed herein, may include historical data associated with an individual surgeon such as prior surgical procedures performed and a number of times the individual surgeon performed each surgical procedure. A training quota may be associated with a particular surgical procedure or intraoperative event such that when a surgeon needs to be assigned to a particular prospective surgical procedure, a surgeon who has not yet reached a training quota may be assigned to the particular prospective surgical procedure in order to meet or fulfill a training quota. Additionally or alternatively, an indication of a training quota, an indication of an individual surgeon's progress towards a training quota, or an indication of whether an individual surgeon has met a training quota associated with a particular prospective surgical procedure may be displayed for a scheduler when assigning a surgical team to a particular prospective surgical procedure. According to desired functionality, some embodiments may prioritize assigning surgical teams based on a training quota. In situations where there is a reassignment or a change in a surgical schedule, one of the factors that the system may take into account is a training quota. That is, before reassigning a surgeon, the system may confirm in advance that the associated training quota is satisfied.

In some embodiments, the assigning of the particular surgeon may be based on an anticipated intraoperative event in the at least one particular prospective surgical procedure. A particular surgeon may be assigned to a particular prospective surgical procedure based on an anticipated intraoperative event such as an action, a planned event, an anatomical structure, or a medical instrument or device. For example, based on historical data of similar surgical procedures, an artificial neural network may analyze prior surgical footage to ascertain intraoperative events likely to be encountered in a prospective surgery. Similar computational analyses may be performed on surgical footage of surgeons available for assignment to a prospective surgery and their skill levels ascertained through this computational analysis may be compared to the skill level required to perform the surgical procedure. The assignment may be based on an expected amount of time for a particular surgeon to perform the anticipated surgical procedure, the determined skill level of the particular surgeon, and/or patient characteristics associated with the anticipated surgical procedure. For example, if a particular prospective surgical procedure is expected to be of minor complexity based on past video frame analysis of similar surgical procedures, a surgeon with a lower skill level may be selected by the system.

In some embodiments, the assigning of the particular surgeon may be based on an expected complexity level of the at least one particular prospective surgical procedure. Complexity level may be indicative of or associated with the complexity of a surgical procedure or a portion thereof. Complexity level may be based on patient characteristics, surgical procedure characteristics, anticipated intraoperative events, additional surgical procedure characteristics, a comparison of a surgeon's skill level and a required skill level for a surgical procedure, an expected amount of time for a surgical procedure, and any other condition or event that correlates to surgical complexity. For example, historical data may include an indication of a statistical relationship between particular patient characteristics and a particular surgical complexity level. The statistical relationship may be any information that may indicate some correlation between the particular surgical complexity level and the patient characteristics. For example, when an overweight male patient over 65 years of age presents with high blood pressure and diabetes, the system may project a higher complexity level based on video analysis of prior procedures performed on similar patients. The patient characteristics may statistically correlate to a surgical complexity level, and the system may therefore set as parameter for the surgical assignment that a surgeon have a particular skill set. A particular surgeon may be determined to have that particular skill set using an artificial neural network applied to surgical footage associated with the particular surgeon. When changing an assignment of a surgeon, the same or similar analysis may be applied as when originally assigning a surgeon to a surgical procedure. In some embodiments, assigning a particular surgeon may be further based on a schedule of the particular surgeon. A particular surgeon's schedule may be manifest within an existing surgical schedule, a surgeon's personal schedule, an overall hospital schedule for the surgeon or any other record of when a surgeon is available or unavailable to perform surgical procedures. These schedules, maintained electronically, may be inputs to the system, and may be accounted for in assigning a particular surgeon to a particular surgery. Additionally, a schedule of a particular surgeon may account for personal preferences of the particular surgeon, such as a preferred start or end time, a maximum expected amount of time to perform a prospective surgical procedure, or a minimum amount of time between surgical procedures.

In some embodiments, the assigning of a particular surgeon may be based on requirements of additional surgeries in the plurality of prospective surgical procedures. For example, requirements of other surgeries in the schedule may have an impact on each surgery in the schedule, because resources (e.g., surgeons with particular skills, staff, space, and equipment) are often in limited supply. The system may take some or all of these variables into account when assigning a particular surgeon to a surgery. For example, a particular surgeon may be assigned to an earlier prospective surgical procedure having a shorter duration in order to allow the particular surgeon to have room in her schedule to handle a succeeding surgical procedure scheduled to begin immediately after the procedure of shorter duration. In another example, a particular surgeon with a first skill level may be assigned to a prospective surgical procedure requiring a first skill level in order to assign another surgeon with a second skill level to a different prospective surgical procedure occurring at the same time.

Disclosed embodiments may further involve determining an expected finish time of the at least one particular prospective surgical procedure based on the assigning of the particular surgeon. A schedule may include a start time and an expected finish time for a particular prospective surgical procedure. Based on analysis performed on surgical video or based on surgical time records associated with prior procedures, the system may predict for a particular surgeon the amount of time it will take to complete the surgery. Each surgeon's time may vary based on experience level, patient characteristics, team members, and other factors that may correlate to the expected surgical duration. The system may perform this calculation in advance using artificial intelligence applied to past surgical procedures, and in this way predict an ending time for a prospective surgical procedure. Thus, based on a selection of a particular surgeon, the duration of the surgery, and its ending time may be predicted. The ending time may then be used in scheduling the surgeon and the operating space for succeeding procedures.

In some examples, changing an assignment of a particular surgeon may be based on requirements associated with at least one other prospective surgical procedure of the plurality of prospective surgical procedures. This may allow an automated or manual scheduler to change an assignment in response to new or updated information, such as requirements associated with a prospective surgical procedure. For example, a particular surgeon with a particular skill level may be assigned to a particular prospective surgical procedure, then the assignment may be changed to another prospective surgical procedure with a different required skill level because the particular surgeon is the only surgeon that meets the required skill level. Such a change may occur as the result of analysis in an artificial neural network of video frames captured during prior surgical procedures, as discussed herein.

Some aspects of this disclosure may include suggesting an alternative surgeon to be assigned to the at least one particular prospective surgical procedure. For example, as changes in a schedule cascade, the system may need to reassign one or more surgeons in in order to meet system constraints. In addition or alternatively, pick lists may be provided by the system, and the pick list may be populated by more than one surgeon who meets the criteria for handling a particular surgical procedure. The suggestions of alternative surgeons may occur after performing neural network analysis on video footage of the prior surgeons and determining their suitability as serving as a suitable alternative. In some examples, multiple alternative surgeons may be suggested or recommended for the same particular prospective surgical procedure. The suggestion of an alternative surgeon to be assigned to the at least one particular prospective surgical procedure may be based on at least one of a training requirement, an anticipated intraoperative event in the at least one particular prospective surgical procedure, an expected complexity level of the at least one particular prospective surgical procedure, and requirements of additional surgeries in the plurality of prospective surgical procedures, as disclosed herein. The criteria for selecting an alternative surgeon may vary from procedure to procedure. For some procedures, training quota or skill level may be a higher priority if the expected complexity level of the particular prospective surgical procedure is high. In another example, the alternative surgeon may be suggested based on a specialty or experience of the alternative surgeon with an anticipated intraoperative event.

Some embodiments may include suggesting an additional surgeon to be assigned to the at least one particular prospective surgical procedure. For example, based on artificial neural network analysis of prior similar surgical procedures, it may be determined that a benefit may be achieved by have more than one surgeon participate in a surgical procedure. In such instances the system may automatically assign or suggest the additional surgeon. In some examples, multiple additional surgeons may be suggested or recommended for the same particular prospective surgical procedure. The suggestion of an additional surgeon may be based on at least one of a training requirement, an anticipated intraoperative event in the at least one particular prospective surgical procedure, an expected complexity level of the at least one particular prospective surgical procedure, and requirements of additional surgeries in the plurality of prospective surgical procedures, as disclosed herein. Suggesting an additional surgeon may decrease the expected time to perform the prospective surgical procedure, provide supervision or training, decrease the complexity, or otherwise increase the compatibility, as disclosed here. The additional surgeon may be suggested or recommended by outputting an indicator. The indicator may be different or the same as an indicator that a particular surgeon meets the requirements of the at least one particular prospective surgical procedure.

Some embodiments may involve updating an expected finish time of the at least one particular prospective surgical procedure based on the suggested additional surgeon. With an additional surgeon added to the team, the surgery may move more quickly, which may have an added benefit of freeing the operating room sooner. Using artificial intelligence or statistical models applied to historical data of prior surgeries performed by each assigned surgeon working alone or the two assigned surgeons working together, the system may predict a new finish time for the surgical procedure. Alternatively, assigning an additional surgeon may increase the expected amount to time, such as when one of the particular surgeon or additional surgeon is assigned to the particular prospective surgical procedure based on a training requirement. The prediction of the new ending time may be determined in a manner similar to the manner described above.

Some embodiments may include, based on the analyzing of the plurality of video frames, determining a compatibility score for the particular surgeon with the at least one particular prospective surgical procedure. Compatibility may relate to whether a particular surgeon may be prepared for, qualified to perform, available to perform, and/or able to successfully complete a particular prospective procedure. A compatibility score may represent a degree of overall compatibility of a particular surgeon with a particular prospective surgical procedure based on the skill level of the particular surgeon, patient characteristics, patient preference, the expected amount of time for the particular surgeon to perform the particular prospective surgical procedure, the requirements for the particular prospective surgical procedure, logistical considerations, and/or any other factor or combination of factors influencing the compatibility between the particular surgeon and the particular prospective surgical procedure. A compatibility score may be expressed in various ways, including on a numerical scale (e.g., 1-10, 1-100, etc.), as a percentage, on a scale of text-based indicators (e.g., "highly compatible," "moderately compatible," "incompatible," etc.) or any other suitable or desired format for expressing the compatibility of a particular surgeon and a particular prospective surgical procedure. The compatibility score may be determined using artificial intelligence as applied to video frames of prior surgical procedures performed by an associated surgeon. As described herein, machine vision may assess various factors in the video in order to arrive at the surgeon's compatibility with a particular surgical procedure. While a compatibility score is described herein as the compatibility score of a surgeon, in some embodiments the compatibility score may be associated with another healthcare professional, such as a surgical technician, a nurse, a physician's assistant, an anesthesiologist, a doctor, or any other healthcare professional participating in a procedure.

As alluded to above, in some embodiments, compatibility may be determined based on computer image analysis of the plurality of video frames of prior surgical procedures. Computer image analysis may include using an artificial neural network model trained using example video frames including previously identified surgical events to thereby identify a similar surgical event in a set of frames, as described herein. The computer image analysis may identify the skill level of the particular surgeon, patient characteristics, the amount of time required to perform the previous surgical event, the requirements for the previous surgical event, and any logistical considerations and determine a compatibility between a particular surgeon and one or more prospective surgical procedures by recognizing correlations or other statistical relationships between previously identified surgical events and the prospective surgical procedure. The computer image analysis may output a compatibility indicator, such as a compatibility score, representing the overall compatibility of a particular surgeon and a particular prospective surgical procedure. In one example, at least one convolution of at least a portion of the plurality of video frames of prior surgical procedures may be calculated, and the compatibility may be determined based on the calculated at least one convolution.

Some embodiments may involve analyzing video of additional surgeons, generating compatibility scores for the plurality of additional surgeons, and assigning the particular surgeon to the at least one particular prospective surgical procedure based on a comparison of the compatibility score of the particular surgeon with the plurality of compatibility scores of the additional surgeons. Video associated with multiple surgeons may be analyzed, as described herein. The analysis may generate a compatibility score to represent an overall compatibility of each surgeon and a particular prospective surgical procedure. The compatibility scores of the multiple surgeons for a particular prospective surgical procedure may be displayed or otherwise indicated. In some embodiments, the compatibility scores of the multiple surgeons for a particular prospective surgical procedure may be ranked. Based on a comparison of all the compatibility scores of the multiple surgeons for the particular prospective surgical procedure, a particular surgeon may be assigned to the particular prospective surgical procedure. For example, the particular surgeon with the highest degree of compatibility may be assigned to the particular prospective surgical procedure. This may be done automatically through the application of an algorithm that receives each compatibility score of each available surgeon and selects the highest ranked available surgeon for a specific surgical procedure. The process may seek to optimize compatibility across multiple surgical procedures.

In some embodiments, assigning may be based on an analysis of compatibility of a particular surgeon with a plurality of prospective surgical procedures. The analysis may generate a compatibility score to represent an overall compatibility of each prospective surgical procedure and the particular surgeon. The compatibility scores of the multiple prospective surgical procedures for a particular surgeon may be displayed or otherwise indicated. In some embodiments, the compatibility scores of the multiple prospective surgical procedures for a particular surgeon may be ranked. Based on a comparison of all the compatibility scores of the multiple prospective surgical procedures for the particular surgeon, the particular surgeon may be assigned to a particular prospective surgical procedure. For example, the surgeon may be assigned to the prospective surgical procedure with the highest degree of compatibility. In one example, a compatibility function may calculate a compatibility score of the particular surgeon and a particular prospective surgical procedure based on information related to the particular surgeon and information related to the particular prospective surgical procedure. For example, the compatibility function may be learned by training a machine learning regression algorithm using training examples. An example of such training example may include information related to a first surgeon and information related to a first surgical procedure, together with a label indicating a desired compatibility score for the first surgeon and the first surgical procedure.

Some embodiments may involve providing to the particular surgeon visual preparation material for the at least one particular prospective surgical procedure. Visual preparation material may include a plurality of video frames associated with the particular prospective surgical procedure. For example, the system may select video clips from prior similar surgical procedures, thereby providing the surgeon with a preview of what might be expected in the impeding surgery. These clips may include images from varying angles, images of varying techniques, and images of differing associated complications. The visual preparation material may be provided to the particular surgeon via an output to a display device, such as a screen (e.g., an OLED, QLED LCD, plasma, CRT, DLPT, electronic paper, or similar display technology), a light projector (e.g., a movie projector, a slide projector), a 3D display, screen of a mobile device, electronic glasses, or any other form of visual and/or audio presentation. In other embodiments, outputting the video for display may include storing the video in a location that is accessible by one or more other computing devices. Such storage locations may include a local storage (such as a hard drive of flash memory), a network location (such as a server or database), a cloud computing platform, or any other accessible storage location. The video may be accessed from a separate computing device for display on the separate computing device. In some embodiments, outputting the video may include transmitting the video to an external device. For example, outputting the video for display may include transmitting the video through a network to a user device for playback on the user device.

Visual preparation material (such as images, video clips, etc.) may be generated or determined by calculating at least one convolution, as disclosed herein, of at least part of the plurality of video frames associated with the particular prospective surgical procedure. The convolution may be used to generate or determine visual preparation material associated with a particular prospective surgical procedure. In one example, a Generative Adversarial Network (GAN) may be trained using training examples to generate visual material (such as images, video clips, etc.), and the trained GAN may generate the visual preparation material based on information related to the at least one particular prospective surgical procedure. An example of such training example may include information related to a first particular prospective surgical procedure, together with a desired visual training material.

Figure 23:
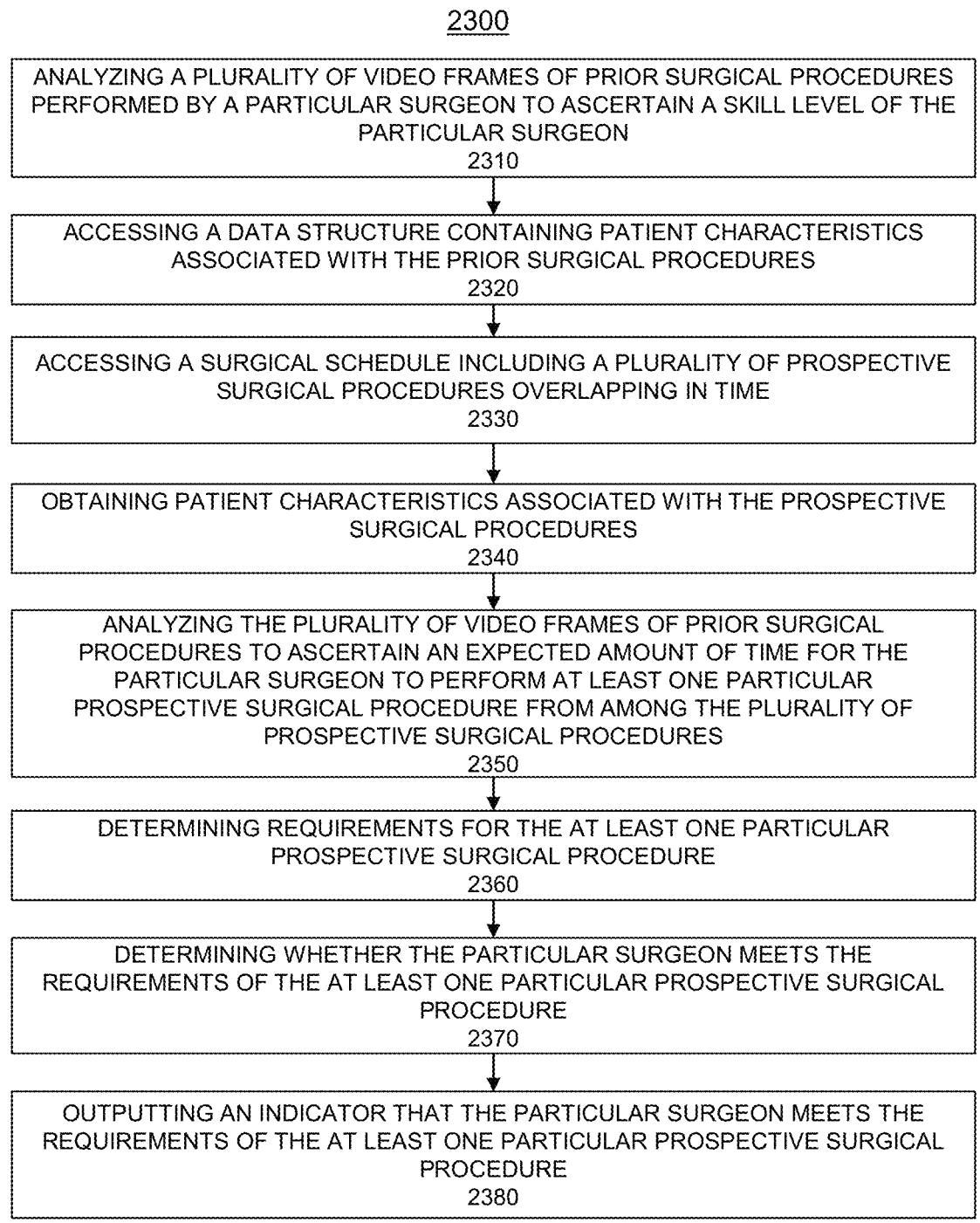
FIG. 23 is a block diagram illustrating an exemplary process for assigning surgical teams to prospective surgical procedures, consistent with disclosed embodiments.

FIG. 23 is a block diagram illustrating an example process 2300 for assigning surgical teams to prospective surgeries. Process 2300 may be performed by one or more processors that implement artificial intelligence functionality. In some embodiments, a non-transitory computer readable medium may contain instructions that when executed by a processor cause the processor to perform process 2300. Process 2300 is not necessarily limited to the steps shown in FIG. 23 and any steps or processes of the various embodiments described throughout the present disclosure may be included in process 2300.

At step 2310, process 2300 may include analyzing a plurality of video frames of prior surgical procedures performed by a particular surgeon to ascertain a skill level of the particular surgeon. Video frames may refer to any video, group of video frames, or video footage including representations of prior surgical procedures associated with the particular surgeon. Analyzing may involve artificial intelligence applied to the video frames, such as through the use of an artificial neural network, as described herein. A skill level of the particular surgeon may indicate or measure the individual surgeon's relative abilities.

At step 2320, process 2300 may include accessing a data structure containing patient characteristics associated with the prior surgical procedures. Accessing a data structure may include reading and/or writing patient characteristics, such as age, gender, and medical considerations to the data structure. At step 2330, process 2300 may include accessing a surgical schedule including a plurality of prospective surgical procedures overlapping in time. A surgical schedule may include timing information, location information, personnel information, or any other details associated with a prospective surgery. At step 2340, process 2300 may include obtaining patient characteristics associated with the prospective surgical procedures, for example as described above.

At step 2350, process 2300 may include analyzing the plurality of video frames of prior surgical procedures to ascertain an expected amount of time for the particular surgeon to perform at least one particular prospective surgical procedure from among the plurality of prospective surgical procedures. Analyzing the plurality of video frames of prior surgical procedures may involve any suitable statistical data analysis, as disclosed herein.

At step 2360, process 2300 may include determining requirements for the at least one particular prospective surgical procedure. The requirements may include at least a required skill level of a participating surgeon based on the patient characteristics associated with the at least one particular prospective surgical procedure and/or an expected amount of time to perform the at least one particular prospective surgical procedure.

At step 2370, process 2300 may include determining whether the particular surgeon meets the requirements of the at least one particular prospective surgical procedure. The determination may be based on the skill level of the particular surgeon and the expected amount of time for the particular surgeon to perform the at least one particular prospective surgical procedure.

At step 2380, process 2300 may include outputting an indicator that the particular surgeon meets the requirements of the at least one particular prospective surgical procedure. An indicator may include any visual or audible signal that demonstrates or shows a user that a particular surgeon meets the minimal requirements to perform a particular prospective surgical procedure.

Disclosed embodiments may include any one of the following bullet-pointed features alone or in combination with one or more other bullet-pointed features, whether implemented as a method, by at least one processor, and/or stored as executable instructions on non-transitory computer-readable media:

receiving a plurality of video frames from a plurality of surgical videos of a plurality of surgical procedures performed by a specific medical professional wherein each surgical video is associated with a differing patient accessing a set of surgical event-related categories wherein each surgical event-related category is denoted by a differing category indicator analyzing the received plurality of video frames of each surgical video to identify a plurality of surgical events in each of the plurality of surgical videos wherein each of the identified plurality of surgical events in each of the plurality of surgical videos is defined by a differing subgroup of frames assigning each differing subgroup of frames to one of the surgical event-related categories to thereby interrelate subgroups of frames from differing surgical procedures under an associated common surgical event-related category evaluating each subgroup of frames associated with each surgical event-related category to derive at least one statistic associated with each subgroup of frames aggregating each statistic within each category of surgical events displaying the surgical event-related categories for selection together with the aggregated statistic for each surgical event-related category receiving a selection of a particular surgical event-related category presenting at least part of the frames assigned to the particular surgical event-related category wherein presenting at least part of the frames assigned to the particular surgical event-related category includes grouping video frames from different surgical videos wherein presenting includes a video playback of a particular subgroup of frames associated with the selection, wherein the particular subgroup of frames corresponds to at least one associated surgical event wherein the video playback of a particular subgroup of frames includes frames from a plurality of differing surgical procedures receiving a plurality of additional surgical videos from a plurality of surgical procedures performed by other medical professionals deriving from frames of the plurality of additional surgical videos statistical data for the other medical professionals presenting a statistical comparison of the specific medical professional with the other medical professionals wherein the grouping of video frames includes sequential sets of video frames of surgical procedures on differing patients wherein presenting includes a video playback of sequential excerpts from the surgical procedures on differing patients presenting in a common view patient-related data for a particular patient, and a video player configured to playback frames of surgical video associated with the particular patient.

wherein as frames associated with differing patients are presented sequentially, the patient-related data in the common view changes wherein the category indicators denote intraoperative surgical events wherein the category indicators denote at least one of operative milestones or intraoperative decisions displaying graphic characterizing aspects within a category, enabling selection of a particular aspect, and upon selection of a particular aspect, identifying video frames associated with the selected aspect for playback displaying in a juxtaposed manner, statistics of the specific medical professional and statistics of at least one of the other medical professionals providing an interface for permitting comparison of video frames captured from the specific medical professional and the at least one other medical professional analyzing the plurality of video frames to determine an average skill of a category of physicians presenting an interface enabling the specific physician to self-compare with the average skill receiving a selection via a user interface of a category of physicians for comparison wherein the user interface is configured to permit selection from a group consisting of at least two of a division, a department, a hospital, a demographic, and literature receiving patient-related personal information including at least two of age, gender, ethnicity, socioeconomic status, marital status, geographic location, or preexisting medical conditions; and during a time when the grouping of video frames is presented, simultaneously display the patient-related personal information receiving a plurality of video frames from a surgical video feed analyzing at least some of the plurality of video frames to identify a surgical instrument therein evaluating the plurality of video frames with the identified surgical instrument therein to ascertain an interface area corresponding to a location of an interaction between the identified surgical instrument and tissue accessing stored data characterizing a surgical plane corresponding to the location of the interaction using the stored data to determine whether the interface area is outside of the surgical plane outputting an out-of-surgical plane signal indicating a deviation from the surgical plane by the surgical instrument wherein the surgical plane is between two organs.

wherein the surgical plane is characterized by a curved area.

wherein the plurality of video frames of the video feed is obtained from pre-stored video footage of the surgical procedure.

wherein the video feed is a real time broadcast of the surgical procedure.

wherein the operations are continuously repeated to continuously monitor deviations from the surgical plane wherein the operations are continuously repeated to ascertain during the surgical procedure when the surgical instrument is projected to deviate from the surgical plane wherein the operations further include outputting a warning signal before the surgical instrument deviates from the surgical plane wherein ascertaining includes tracking movement in the plurality of surgical frames of the surgical instrument to define a projected path of the surgical instrument wherein outputting the warning signal occurs when the surgical instrument is within a predetermined distance from the surgical plane wherein the warning signal includes instructions on how to avoid deviation from the surgical plane determining from the plurality of video frames a current step of the surgical procedure using the determined current step to identify the stored data characterizing a surgical plane wherein the stored data characterizing a surgical plane is derived from at least one prior surgical procedure wherein the stored data characterizing a surgical plane is derived from a plurality of prior surgical procedures wherein using the stored data to determine whether the interface area is outside of the surgical plane includes applying artificial intelligence to video frames of prior surgical procedures and extrapolating the surgical plane therefrom wherein the stored data characterizing the surgical plane includes an indication of expected tissue colors corresponding to the surgical plane wherein the determination of whether the interface area is outside of the surgical plane is based on the expected tissue colors corresponding to the surgical plane and on color data of one or more pixels corresponding to the interface area in at least one of the plurality of video frames wherein the determination of whether the interface area is outside of the surgical plane is based on at least one convolution of a plurality of pixels corresponding to the interface area in at least one of the plurality of video frames receiving a plurality of video frames from a surgical video feed of an ongoing surgical procedure accessing stored data based on prior surgical procedures predicting, based on the plurality of video frames and the stored data based on the prior surgical procedures, at least one expected future event in the ongoing surgical procedure generating for intra-surgical presentation, at least one option to review at least one surgical video clip associated with the expected future event in the surgical procedure accessing a data structure containing the at least one surgical video clip outputting for intra-surgical presentation, the at least one surgical video clip associated with the expected future event wherein the surgical video clip includes selected portions of the surgical video feed of the ongoing surgical procedure captured before the generation of the at least one option wherein the operations further comprise selecting the portions of the surgical video feed based on the predicted at least one expected future event in the ongoing surgical procedure wherein the operations further comprise determining at least one prerequisite of the predicted at least one expected future event in the ongoing surgical procedure wherein the selected portions of the surgical video feed of the ongoing surgical procedure are configured to enable a surgeon to verify the at least one prerequisite wherein the at least one prerequisite is a plurality of prerequisites enabling the surgeon to select a prerequisite of the plurality of prerequisites causing a presentation of a portion of the surgical video feed of the ongoing surgical procedure captured before the generation of the at least one option and corresponding to the selected prerequisite wherein a first part of the selected portions of the surgical video feed of the ongoing surgical procedure corresponds to a first prerequisite of the predicted at least one expected future event in the ongoing surgical procedure, a second part of the selected portions of the surgical video feed of the ongoing surgical procedure corresponds to a second prerequisite of the predicted at least one expected future event in the ongoing surgical procedure causing a presentation of an indication of the first prerequisite in conjunction with the intra-surgical presentation of the first part of the selected portions causing a presentation of an indication of the second prerequisite in conjunction with the intra-surgical presentation of the second part of the selected portions receiving a signal indicative of an entering of a surgeon to the ongoing surgical procedure outputting for intra-surgical presentation at least part of the surgical video feed of the ongoing surgical procedure in response to the signal wherein the at least part of the surgical video feed of the ongoing surgical procedure is a visual summary of the ongoing surgical procedure before the entering of the surgeon receiving an indication of a user desire to review past occurrences of the ongoing surgical procedure outputting for intra-surgical presentation at least part of the surgical video feed of the ongoing surgical procedure in response to the received indication wherein the at least part of the surgical video feed of the ongoing surgical procedure is a visual summary of the ongoing surgical procedure before the entering of the user wherein the at least one future expected event is a complication, and wherein outputting the at least one video clip includes presenting at least one complication-avoiding video clip demonstrating a surgical technique to avoid the complication wherein the at least one complication-avoiding video clip includes a plurality of complication-avoiding video clips demonstrating alternative surgical techniques to avoid the complication wherein the at least one future expected event is a complication, and wherein the at least one surgical video clip includes at least one misstep clip demonstrating at least one action giving rise to the complication wherein the operations further comprise triggering an intra-surgical warning of a risk in an upcoming portion of the ongoing surgical procedure, describing the risk, and presenting an intra-surgical picklist of risk-reducing video clips for review wherein outputting for intra-surgical presentation includes generating a composite video presentation including clips from a plurality of prior surgical procedures wherein the operations further comprise accessing information characterizing a current patient undergoing the surgical procedure and wherein the at least one surgical video clip is selected to reflect video of at least one prior patient sharing characteristics with the current patient wherein the at least one future expected event is a wound closure, and the at least one surgical video clip is configured to enable a pre-closure surgical review causing to be presented on a display additional options to review additional surgical video related to the at least one surgical video clip outputted for presentation following outputting for intra-surgical presentation receiving a plurality of video frames associated with at least one surgical procedure accessing stored data based on prior surgical procedures processing, using the stored data, the plurality of video frames to assess at least one of tissue handling, economy of motion, depth perception and surgical procedure flow in the plurality of video frames based on the assessment of at least one of tissue handling, economy of motion, depth perception and surgical procedure flow, generating a competency-related score for a subject selecting, from the plurality of video frames, at least one video clip from which the competency score was derived outputting at least one score presenting in association with the at least one score, a link to the at least one video clip wherein presenting the link includes causing a display of a window for playback of the at least one video clip wherein presenting the link includes causing a display of controls enabling selective playback of the at least one video clip wherein presenting the link includes presenting an activatable icon in a graphical user interface wherein the stored data based on prior surgical events includes a machine learning model trained using a data set based on prior surgical events wherein the operations further comprise receiving audio signals associated with the surgical procedure and to determine a level of subject autonomy based at least in part on the audio signals wherein the operations further comprise determining, at least in part from the plurality of video frames, an identity of the subject wherein operations further comprise determining the identity of the subject is based on at least one of user input, an associated medical record, facial recognition, voice recognition and an output of a personnel tracking system wherein the at least one score includes a plurality of scores, each of the plurality of scores being associated with a differing skill wherein the at least one video clip includes a plurality of video clips, and where each video clip is associated with a differing score wherein the at least one score includes a composite score assessing a plurality of scores wherein the at least one surgical procedure includes a plurality of surgical procedures wherein the at least one video clip includes a plurality of video clips wherein during presenting the instructions are configured to present at least one video clip capture date in association with each of the plurality of video clips wherein the operations further comprise updating a personnel record of the subject with the at least one competency score classifying a surgical procedure type associated with the at least one video clip presenting a control enabling a viewer to access other video clips in which the subject is presented, sharing the surgical procedure type selecting a surgical team member for a prospective surgery based on the competency-related score providing a suggestion for additional training of the subject in response to a first competency-related score forgoing providing a suggestion for additional training of the subject in response to a second competency-related score causing the at least one competency score to populate an evaluation form of the subject calculating at least one convolution of at least part of at least one of the plurality of video frames using the stored data to analyze the calculated at least one convolution using the analysis of the calculated at least one convolution to assess the at least one of tissue handling, economy of motion, depth perception and surgical procedure flow in the plurality of video frames receiving an ID of a piece of equipment in a medical facility receiving location information for the piece of equipment in the medical facility receiving medical information captured by the piece of equipment during a medical procedure ascertaining a time of information capture by the piece of equipment accessing at least one data record that associates scheduled medical procedures with locations of medical procedures and patient information performing a look-up in the data record to determine an identity of a particular patient assigned to a location associated with the location information using at least the location information and the ascertained time accessing a medical record data structure performing a lookup in the medical record data structure to identify a medical record of the particular patient using the identity of the particular patient establishing an association between the medical information captured by the piece of equipment and at least some information in the medical record of the particular patient to thereby enable access to the medical information captured by the piece of equipment through access to the medical record of the particular patient wherein the piece of equipment includes at least one image sensor, wherein the location information includes image data captured by the image sensor processing the image data to determine an identity of a space corresponding to the location wherein the piece of equipment includes at least one transmitter configured to transmit location signals to at least one receiver associated with the location wherein the location information received is based on the signals detected by the at least one receiver wherein the medical information captured by the piece of equipment during the medical procedure includes image data of a procedure performed on the particular patient wherein establishing an association includes linking the image data with the medical record of the particular patient wherein the image data is video footage of the medical procedure wherein the piece of equipment is configured to capture at least one vital sign wherein the captured medical information includes at least one vital sign of the particular patient wherein establishing an association includes linking the captured at least one vital sign of the particular patient with the medical record of the particular patient wherein the piece of medical equipment is movable between spaces in the medical facility wherein accessing at least one data record that associates scheduled medical procedures with locations of medical procedures and patient information includes accessing medical facility scheduling software assigning patients to spaces at particular times wherein the identity of the particular patient includes an anonymized patient ID wherein performing a lookup in the medical record data structure to identify a medical record of the particular patient includes using the anonymized ID to locate the medical record of the particular patient wherein establishing an association between the medical information captured by the piece of medical equipment and at least some information in the medical record of the particular patient includes embedding a link in the medical record to connect to the medical information from another data source
wherein establishing an association between the medical information captured by the piece of medical equipment and at least some information in the medical record of the particular patient includes storing at least part of the image data in the medical record
wherein establishing an association between the medical information captured by the piece of medical equipment and at least some information in the medical record includes storing the video footage in a video footage repository and embedding in the medical record a link to the stored video footage
outputting data based on the association
transmitting patient-specific alerts based on information in the medical record
wherein the ID of the piece of equipment includes at least one of a unique identifier, an identifier of equipment type and an identifier of a version
wherein the piece of equipment includes at least one of a blood pressure monitor, a ventilator, an anesthesia delivery machine, an oxygen concentrator, a sleep apnea machine, a kidney dialysis machine, an infusion pump, an insulin pump, a blood analyzer, a respiratory monitoring machine, and a fluid management system
wherein the medical information captured by the piece of equipment during the medical procedure includes image data of a procedure performed on the particular patient
calculating at least one convolution of the image data
determining information based on the calculated at least one convolution
linking the determined information with the medical record of the particular patient to establish the association
retrieving information from the medical record of the particular patient
using the retrieved information to analyze the medical information captured by the piece of equipment
providing information based on the analysis of the medical information captured by the piece of equipment
analyzing a plurality of video frames of prior surgical procedures performed by a particular surgeon to ascertain a skill level of the particular surgeon
accessing a data structure containing patient characteristics associated with the prior surgical procedures
accessing a surgical schedule including a plurality of prospective surgical procedures overlapping in time
obtaining patient characteristics associated with the prospective surgical procedures
analyzing the plurality of video frames of prior surgical procedures to ascertain an expected amount of time for the particular surgeon to perform at least one particular prospective surgical procedure from among the plurality of prospective surgical procedures
determining requirements for the at least one particular prospective surgical procedure, the requirements including a required skill level of a participating surgeon based on the patient characteristics associated with the at least one particular prospective surgical procedure and an expected amount of time to perform the at least one particular prospective surgical procedure
determining whether the particular surgeon meets the requirements of the at least one particular prospective surgical procedure based on the skill level of the particular surgeon and the expected amount of time for the particular surgeon to perform the at least one particular prospective surgical procedure
outputting an indicator that the particular surgeon meets the requirements of the at least one particular prospective surgical procedure
assigning the particular surgeon to the at least one particular prospective surgical procedure
wherein the assigning of the particular surgeon is further based on at least one of a training quota, an anticipated intraoperative event in the at least one particular prospective surgical procedure, an expected complexity level of the at least one particular prospective surgical procedure, and requirements of additional surgeries in the plurality of prospective surgical procedures
changing the assignment of the particular surgeon based on requirements associated with at least one other prospective surgical procedure of the plurality of prospective surgical procedures
wherein the change in assignment is based on at least one of a training quota, an anticipated intraoperative event in at least one of the plurality of prospective surgical procedures, an expected complexity level of the at least one particular prospective surgical procedure, and requirements of additional surgeries in the plurality of prospective surgical procedures
suggesting an alternative surgeon to be assigned to the at least one particular prospective surgical procedure
wherein the suggestion of an alternative surgeon to be assigned to the at least one particular prospective surgical procedure is based on at least one of a training requirement, an anticipated intraoperative event in the at least one particular prospective surgical procedure, an expected complexity level of the at least one particular prospective surgical procedure, and requirements of additional surgeries in the plurality of prospective surgical procedures
suggesting an additional surgeon to be assigned to the at least one particular prospective surgical procedure
wherein the suggestion of an additional surgeon is based on at least one of a training requirement, an anticipated intraoperative event in the at least one particular prospective surgical procedure, an expected complexity level of the at least one particular prospective surgical procedure, and requirements of additional surgeries in the plurality of prospective surgical procedures
assigning the particular surgeon to the at least one particular prospective surgical procedure and determining an expected finish time of the at least one particular prospective surgical procedure based on the assigning of the particular surgeon
updating an expected finish time of the at least one particular prospective surgical procedure based on the suggested additional surgeon
determining a compatibility score for the particular surgeon with the at least one particular prospective surgical procedure based on the analyzing of the plurality of video frames
analyzing video of additional surgeons, generating compatibility scores for the plurality of additional surgeons, and assigning the particular surgeon to the at least one particular prospective surgical procedure based on a comparison of the compatibility score of the particular surgeon with the plurality of compatibility scores of the additional surgeons
wherein assigning of the particular surgeon is further based on a schedule of the particular surgeon providing to the particular surgeon visual preparation material for the at least one particular prospective surgical procedure wherein outputting includes causing a display of an identity of the particular surgeon in association with the at least one particular prospective surgical procedure assigning the particular surgeon to the at least one particular prospective surgical procedure, and wherein the assigning is based on an analysis of compatibility of the particular surgeon with the plurality of prospective surgical procedures wherein the compatibility is determined based on computer image analysis of the plurality of video frames of prior surgical procedures Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A non-transitory computer readable medium including instructions that, when executed by at least one processor, cause the at least one processor to perform statistical analysis operations across surgical videos, the operations comprising:
   receiving a plurality of video frames from a plurality of surgical videos of a plurality of surgical procedures performed by a specific medical professional, wherein each surgical video is associated with a differing patient;
   accessing a set of surgical event-related categories, wherein each surgical event-related category is denoted by a differing category indicator;
   analyzing the received plurality of video frames of each surgical video to identify a plurality of surgical events in each of the plurality of surgical videos, and wherein each of the identified plurality of surgical events in each of the plurality of surgical videos is defined by a differing subgroup of frames;
   assigning each differing subgroup of frames to one of the surgical event-related categories to thereby interrelate subgroups of frames from differing surgical procedures under an associated common surgical event-related category;
   evaluating each subgroup of frames associated with each surgical event-related category to derive at least one statistic associated with each subgroup of frames;
   aggregating each statistic within each category of surgical events, the aggregating including compiling the at least one statistic associated with each subgroup of frames into a composite statistic;
   displaying the surgical event-related categories for selection together with the aggregated statistic for each surgical event-related category;
   receiving a selection of a particular surgical event-related category; and
   upon receipt of the selection, presenting at least part of the frames assigned to the particular surgical event-related category.

2. The non-transitory computer readable medium of claim 1, wherein presenting at least part of the frames assigned to the particular surgical event-related category includes grouping video frames from different surgical videos.

3. The non-transitory computer readable medium of claim 1, wherein presenting includes a video playback of a particular subgroup of frames associated with the selection, wherein the particular subgroup of frames corresponds to at least one associated surgical event.

4. The non-transitory computer readable medium of claim 3, wherein the video playback of a particular subgroup of frames includes frames from a plurality of differing surgical procedures.

5. The non-transitory computer readable medium of claim 1, wherein the operations further comprise receiving a plurality of additional surgical videos from a plurality of surgical procedures performed by other medical professionals, deriving from frames of the plurality of additional surgical videos statistical data for the other medical professionals, and presenting a statistical comparison of the specific medical professional with the other medical professionals.

6. The non-transitory computer readable medium of claim 2, wherein the grouping of video frames includes sequential sets of video frames of surgical procedures on differing patients, and wherein presenting includes a video playback of sequential excerpts from the surgical procedures on differing patients.

7. The non-transitory computer readable medium of claim 1, wherein the operations further comprise presenting in a common view patient-related data for a particular patient, and a video player configured to playback frames of surgical video associated with the particular patient.

8. The non-transitory computer readable medium of claim 7, wherein as frames associated with differing patients are presented sequentially, the patient-related data in the common view changes.

9. The non-transitory computer readable medium of claim 1, wherein the category indicators denote intraoperative surgical events.

10. The non-transitory computer readable medium of claim 1, wherein the category indicators denote at least one of operative milestones or intraoperative decisions.

11. The non-transitory computer readable medium of claim 1, wherein the operations further comprise displaying graphic characterizing aspects within a category, enabling selection of a particular aspect, and upon selection of a particular aspect, identifying video frames associated with the selected aspect for playback.

12. The non-transitory computer readable medium of claim 1, wherein the operations further comprise displaying in a juxtaposed manner, statistics of the specific medical professional and statistics of at least one of the other medical professionals and providing an interface for permitting comparison of video frames captured from the specific medical professional and the at least one other medical professional.

13. The non-transitory computer readable medium of claim 1, wherein the operations further comprise analyzing the plurality of video frames to determine an average skill of a category of physicians, and presenting an interface enabling the specific physician to self-compare with the average skill.

14. The non-transitory computer readable medium of claim 13, wherein the operations further include receiving a selection via a user interface of a category of physicians for comparison.

15. The non-transitory computer readable medium of claim 14, wherein the user interface is configured to permit selection from a group consisting of at least two of a division, a department, a hospital, a demographic, and literature.

16. The non-transitory computer readable medium of claim 2, wherein the operations further comprise:
receiving patient-related personal information including at least two of age, gender, ethnicity, socioeconomic status, marital status, geographic location, or preexisting medical conditions; and
during a time when the grouping of video frames is presented, simultaneously display the patient-related personal information.

17. A system for performing statistical analysis operations across surgical videos, the system comprising:
at least one processor configured to:
receive a plurality of video frames from a plurality of surgical videos of a plurality of surgical procedures performed by a specific medical professional, wherein each surgical video is associated with a differing patient;
access a set of surgical event-related categories, wherein each surgical event-related category is denoted by a differing category indicator;
analyze the received plurality of video frames of each surgical video to identify a plurality of surgical events in each of the plurality of surgical videos, and wherein each of the identified plurality of surgical events in each of the plurality of surgical videos is defined by a differing subgroup of frames;
assign each differing subgroup of frames to one of the surgical event-related categories to thereby interrelate subgroups of frames from differing surgical procedures under an associated common surgical event-related category;
evaluate each subgroup of frames associated with each surgical event-related category to derive at least one statistic associated with each subgroup of frames;
aggregate each statistic within each category of surgical events, the aggregating including compiling the at least one statistic associated with each subgroup of frames into a composite statistic;
display the surgical event-related category selection together with the aggregated statistic for each surgical event-related category;
receive a selection of a particular surgical event-related category; and
upon receipt of the selection, present at least part of the frames assigned to the particular surgical event-related category.

18. The system of claim 17, wherein the at least one processor is further configured to present a video playback of a particular subgroup of frames associated with the selection, wherein the particular subgroup of frames corresponds to at least one associated surgical event.

19. A method of performing statistical analysis across surgical videos, the method comprising:
receiving a plurality of video frames from a plurality of surgical videos of a plurality of surgical procedures performed by a specific medical professional, wherein each surgical video is associated with a differing patient;
accessing a set of surgical event-related categories, wherein each surgical event-related category is denoted by a differing category indicator;
analyzing the received plurality of video frames of each surgical video to identify a plurality of surgical events in each of the plurality of surgical videos, and wherein each of the identified plurality of surgical events in each of the plurality of surgical videos is defined by a differing subgroup of frames;
assigning each differing subgroup of frames to one of the surgical event-related categories to thereby interrelate subgroups of frames from differing surgical procedures under an associated common surgical event-related category;
evaluating each subgroup of frames associated with each surgical event-related category to derive at least one statistic associated with each subgroup of frames;
aggregating each statistic within each category of surgical events, the aggregating including compiling the at least one statistic associated with each subgroup of frames into a composite statistic;
displaying the surgical event-related categories indicators for selection together with the aggregated statistic for each surgical-event related category;
receiving a selection of a particular surgical event-related category; and
upon receipt of the selection, presenting at least part of the frames assigned to the particular surgical event-related category.

20. The method of claim 19, further comprising presenting a video playback of a particular subgroup of frames associated with the selection, wherein the particular subgroup of frames corresponds to at least one associated surgical event.

* * * * *